US011763424B2

(12) United States Patent
Xu et al.

(10) Patent No.: US 11,763,424 B2
(45) Date of Patent: Sep. 19, 2023

(54) DEVICES, SYSTEMS, AND METHODS FOR IMAGE STITCHING

(71) Applicant: SHANGHAI UNITED IMAGING HEALTHCARE CO., LTD., Shanghai (CN)

(72) Inventors: Liang Xu, Shanghai (CN); Shurui Zhao, Shanghai (CN); Yang Hu, Shanghai (CN); Yecheng Han, Shanghai (CN); Wanli Teng, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 361 days.

(21) Appl. No.: 17/111,536

(22) Filed: Dec. 4, 2020

(65) Prior Publication Data
US 2021/0113174 A1 Apr. 22, 2021

Related U.S. Application Data

(63) Continuation of application No. PCT/CN2019/090025, filed on Jun. 4, 2019.

(30) Foreign Application Priority Data

Jun. 4, 2018 (CN) .......................... 201810562311.5
Aug. 1, 2018 (CN) .......................... 201810864201.4
(Continued)

(51) Int. Cl.
*G06T 7/70* (2017.01)
*G06T 3/40* (2006.01)
(Continued)

(52) U.S. Cl.
CPC .......... *G06T 3/4038* (2013.01); *A61B 6/5241* (2013.01); *A61B 6/54* (2013.01);
(Continued)

(58) Field of Classification Search
CPC ....... G06T 7/33; G06T 3/4038; G06T 3/0068; G06T 2200/32; G06T 7/337;
(Continued)

(56) References Cited

U.S. PATENT DOCUMENTS 6,898,269 B2    5/2005   Halsmer et al.
7,773,829 B1    8/2010   Brandt
(Continued)

FOREIGN PATENT DOCUMENTS

AU    2017100064 A4 *   3/2017   ........... G06K 9/0063
CN    201260672 Y        6/2009
(Continued)

OTHER PUBLICATIONS

International Search Report in PCT/CN2019/090025 dated Aug. 28, 2019, 6 pages.
(Continued)

Primary Examiner — Don K Wong
(74) Attorney, Agent, or Firm — METIS IP LLC

(57) ABSTRACT

A method for image stitching is provided. The method may include obtaining a reference image of a first portion of a subject and a target image of a second portion of the subject, and determining at least one pair of feature points based on a preliminary registration accuracy. The first and second portions may at least partially overlap with each other. Each pair may include a reference feature point in the reference image and a target feature point in the target image that matches the reference feature point. For each pair, the method may further include determining an updated pair of feature points based on a superior registration accuracy
(Continued)

higher than the preliminary registration accuracy and a neighboring region of the target feature point of the pair. The method may further include generating a stitched image based on the at least one updated pair.

19 Claims, 29 Drawing Sheets

(30) Foreign Application Priority Data

Aug. 1, 2018 (CN) .......................... 201810865608.9
Dec. 7, 2018 (CN) .......................... 201811493215.6

(51) Int. Cl.
  *G06T 7/73* (2017.01)
  *G06T 7/33* (2017.01)
  *A61B 6/00* (2006.01)
  *G06T 3/60* (2006.01)

(52) U.S. Cl.
  CPC ............... *G06T 3/60* (2013.01); *G06T 7/337* (2017.01); *G06T 7/73* (2017.01); *G06T 2207/10116* (2013.01); *G06T 2207/20212* (2013.01)

(58) Field of Classification Search
  CPC ....... G06T 2207/32; G06T 2207/20221; G06T 2207/10081; G06T 7/38; G06T 2207/10116; G06T 2210/41; G06T 7/11; G06T 7/30
  See application file for complete search history.

(56) References Cited

U.S. PATENT DOCUMENTS

| | | | |
|---|---|---|---|
| 2007/0019853 | A1 | 1/2007 | Luo |
| 2009/0316990 | A1 | 12/2009 | Nakamura et al. |
| 2011/0175947 | A1 | 7/2011 | Lin et al. |
| 2014/0105357 | A1 | 4/2014 | Shin et al. |
| 2014/0177968 | A1 | 6/2014 | Lee et al. |
| 2017/0140199 | A1 | 5/2017 | Hougen et al. |
| 2018/0060682 | A1 | 3/2018 | Cho et al. |
| 2020/0383650 | A1 | 12/2020 | Liu |

FOREIGN PATENT DOCUMENTS

| | | | |
|---|---|---|---|
| CN | 101915573 | A | 12/2010 |
| CN | 102005047 | A | 4/2011 |
| CN | 102494733 | A | 6/2012 |
| CN | 102855510 | A | 1/2013 |
| CN | 104112128 | A | 10/2014 |
| CN | 104173068 | A | 12/2014 |
| CN | 104392238 | A | 3/2015 |
| CN | 104574421 | A | 4/2015 |
| CN | 164677219 | A | 6/2015 |
| CN | 105141843 | A | 12/2015 |
| CN | 105205784 | A | 12/2015 |
| CN | 105405101 | A | 3/2016 |
| CN | 105868750 | A | 8/2016 |
| CN | 106447664 | A | 2/2017 |
| CN | 104287756 | B | 3/2017 |
| CN | 106852697 | A | 6/2017 |
| CN | 107170001 | A | 9/2017 |
| CN | 107424151 | A | 12/2017 |
| CN | 107644411 | A | 1/2018 |
| CN | 107665486 | A | 2/2018 |
| CN | 106120403 | A | 6/2018 |
| CN | 108765277 | A | 11/2018 |
| CN | 108985296 | A | 12/2018 |
| CN | 109063770 | A | 12/2018 |
| CN | 109480878 | A | 3/2019 |
| EP | 2865335 | A2 | 4/2015 |
| EP | 3254626 | A1 | 12/2017 |
| WO | 2007002134 | A2 | 1/2007 |
| WO | 2008020372 | A2 | 2/2008 |
| WO | 2014132361 | A1 | 9/2014 |

OTHER PUBLICATIONS

Written Opinion in PCT/CN2019/090025 dated Aug. 28, 2019, 6 pages.
Lan, Huayong et al., Research on Application of the Scale Extraction of Water—Level Ruler Based on Image Recognition Technology, Yellow River, 37(3): 28-30, 2015.
Ran, Xin et al., Ship draft mark recognition based on image processing, Journal of Shanghai Maritime University, 33 (2): 6-9, 2012.
Liu, Wencai, Key Technology of Vision Measurement and Its Application in the Monitoring of Switch Rail Expansion Displacement, China Excellent Master's Thesis Full-text Database Information Technology Series, 2017, 68 pages.
D.A. Konovalov et al., Ruler Detection for Automatic Scaling of Fish Images, ICAIP 2017: Proceedings of the International Conference on Advances in Image Processing, 2017, 6 pages.
Zhang, Juan, Research of Similarity Measure in Medical Image Registration, China Doctoral Dissertation Full-text Database, 2014, 119 pages.
Don, Lancaster, A Review of Some Image Pixel Interpolation Algorithms, Web page <https://www.docin.com/p-427993169.html>, 2012, 11 pages.
Heung-Yeung Shum et al., Construction and Refinement of Panoramic Mosaics with Global and Local Alignment, Sixth International Conference on Computer Vision, 1998, 6 pages.
Qi, Tian et al., Algorithms for Subpixel Registration, Computer Vision, Graphics, and image Processing, 35(2): 220-233, 1986.
Partial Supplementary European Search Report in European Application No. 19614598.9 dated May 3, 2021, 15 pages.

* cited by examiner

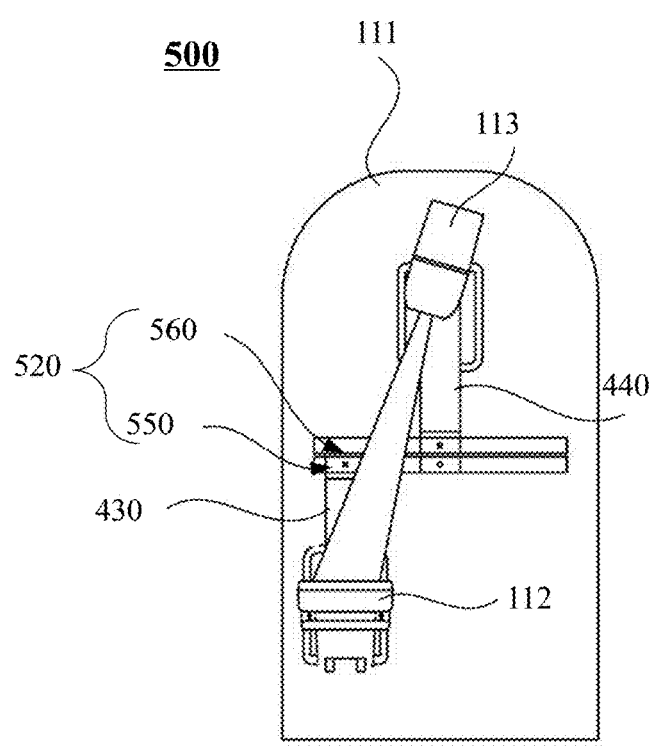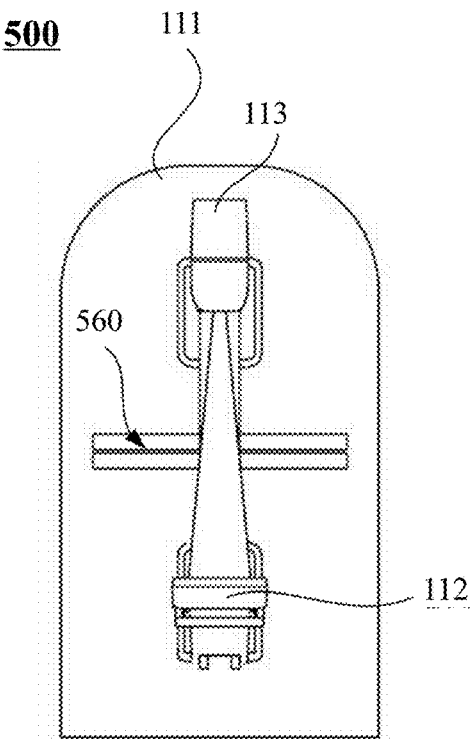
FIG. 5E  FIG. 5F
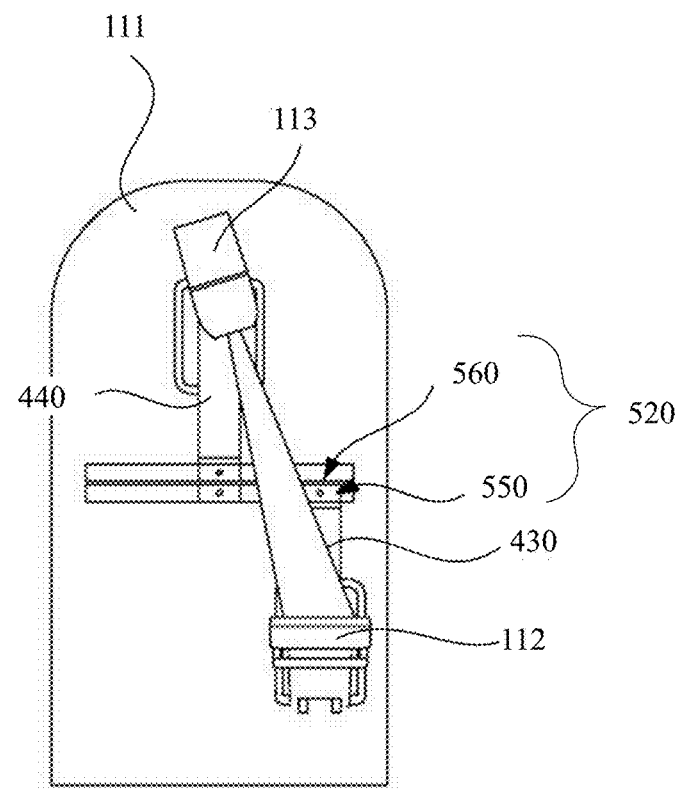
FIG. 5G

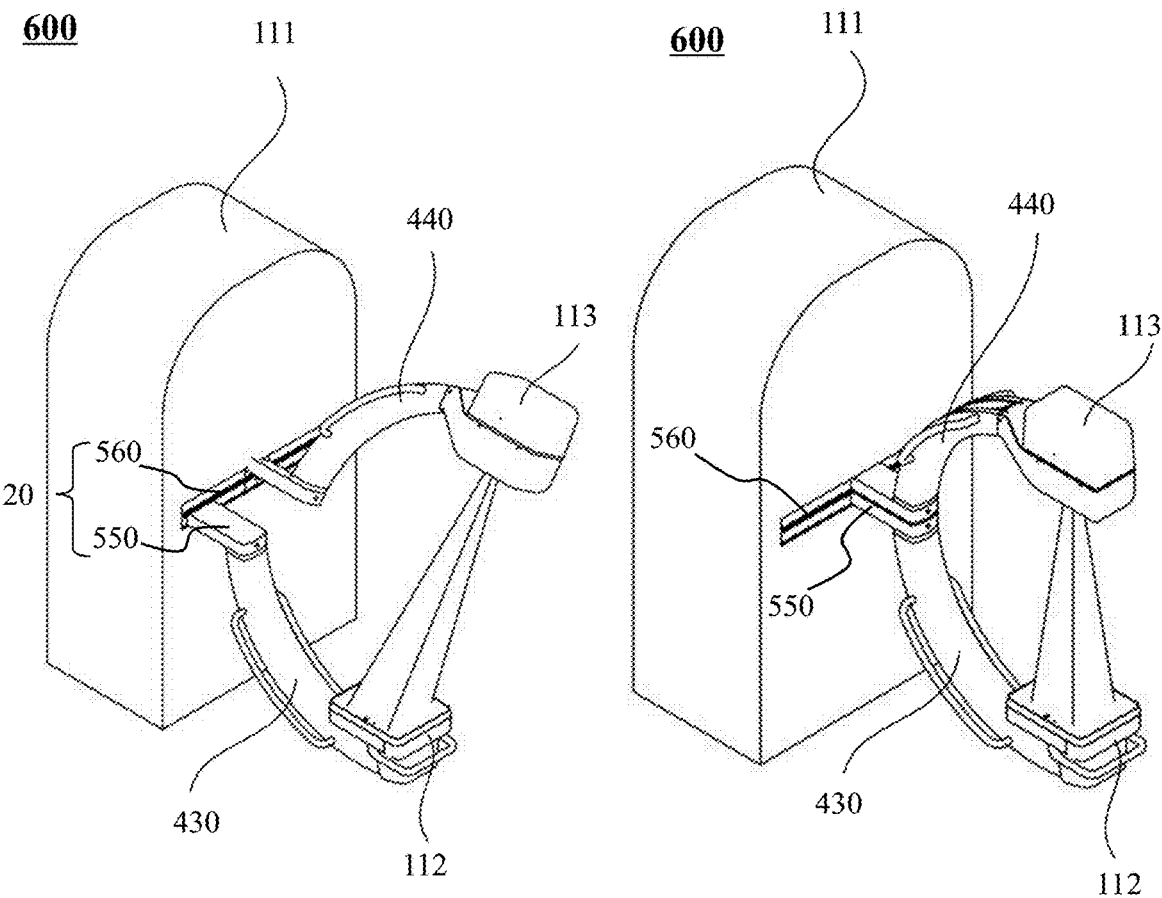
FIG. 6A
FIG. 6B
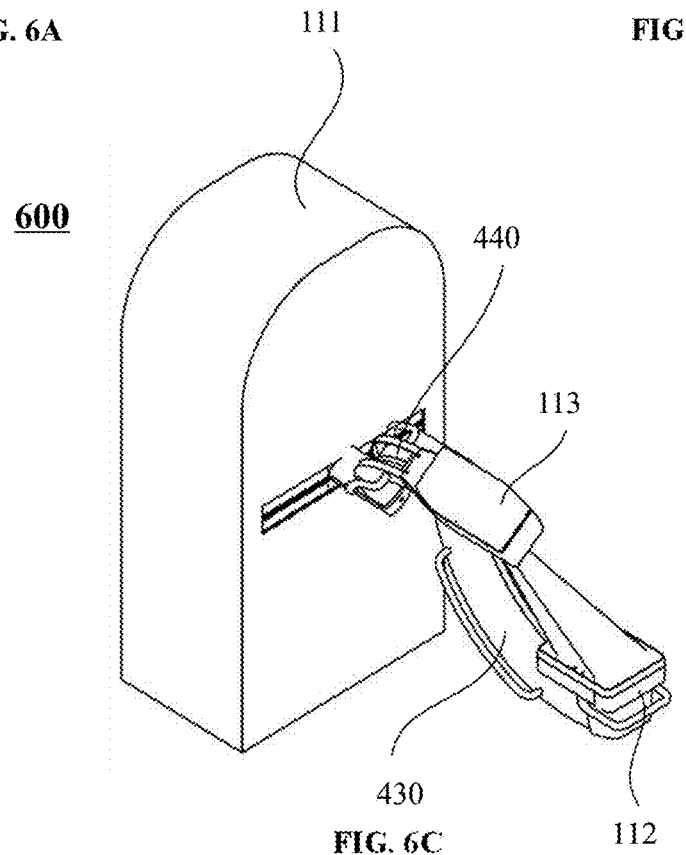
FIG. 6C

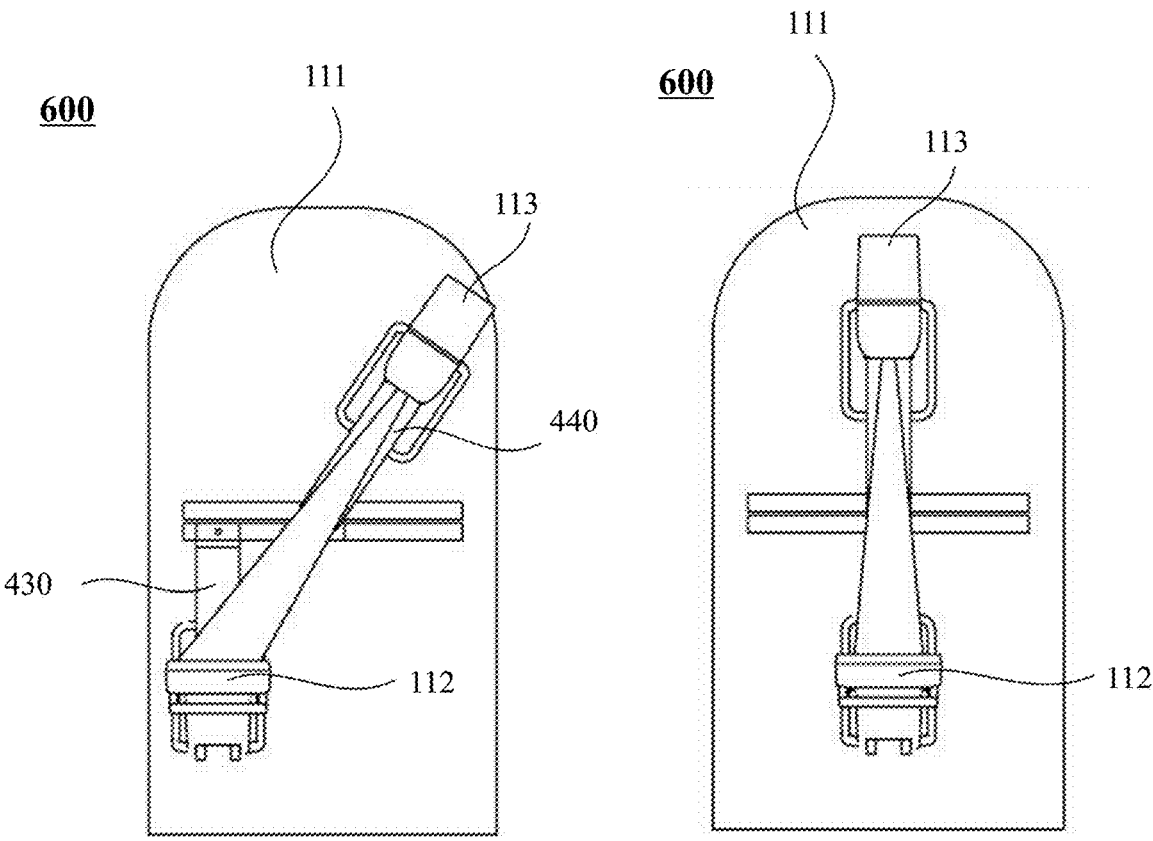
FIG. 6D
FIG. 6E
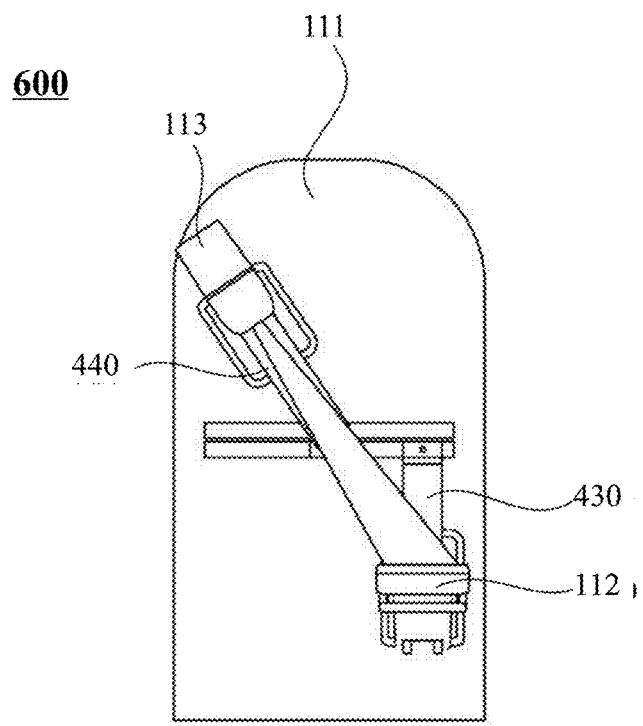
FIG. 6F

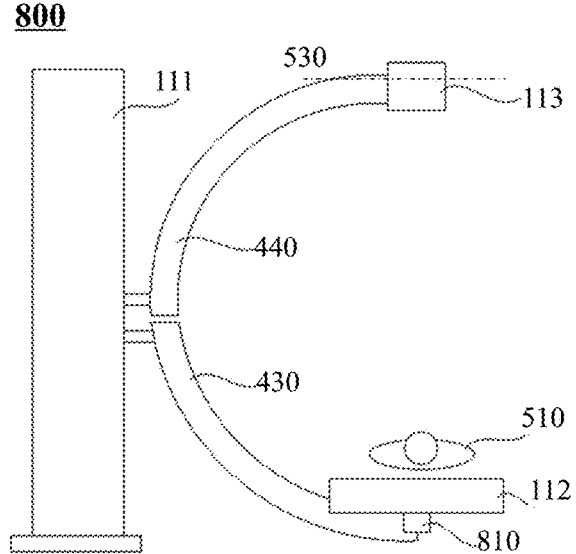
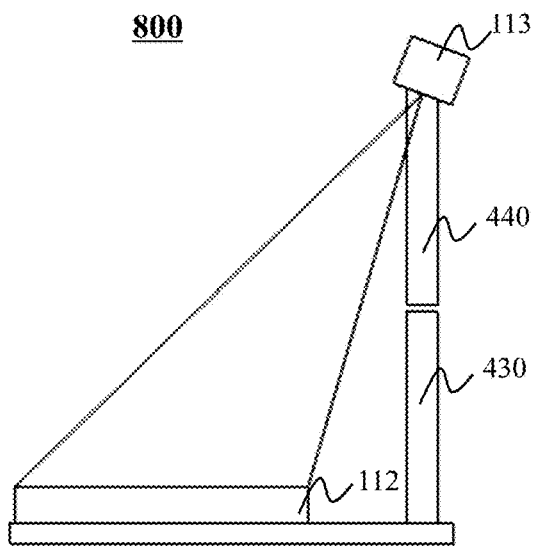
FIG. 8A
FIG. 8B
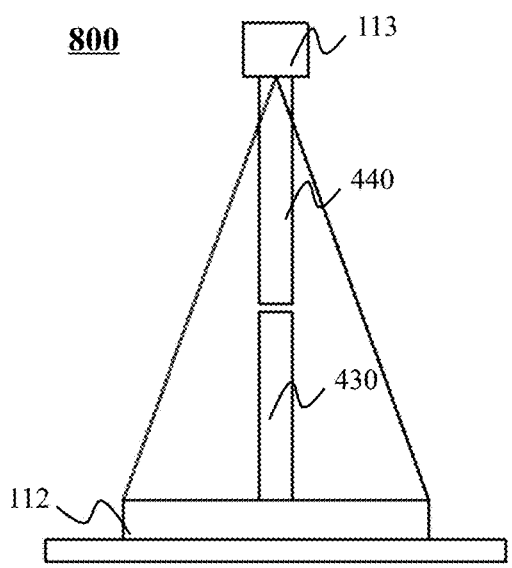
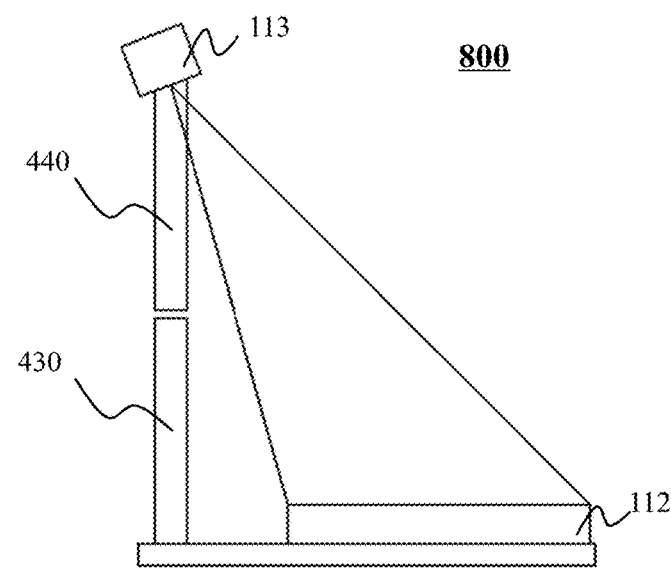
FIG. 8C
FIG. 8D

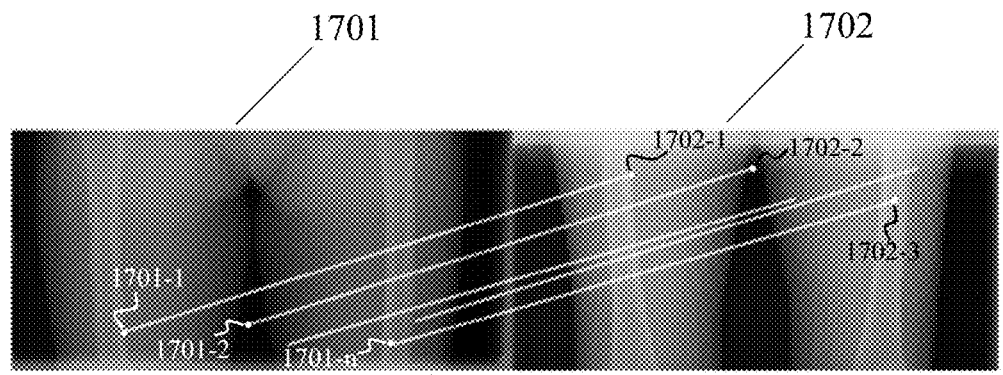
FIG. 17
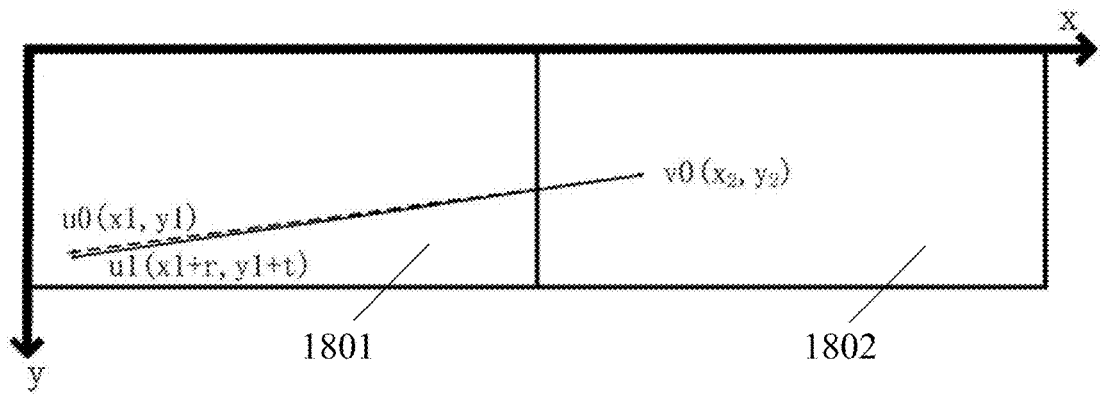
FIG. 18
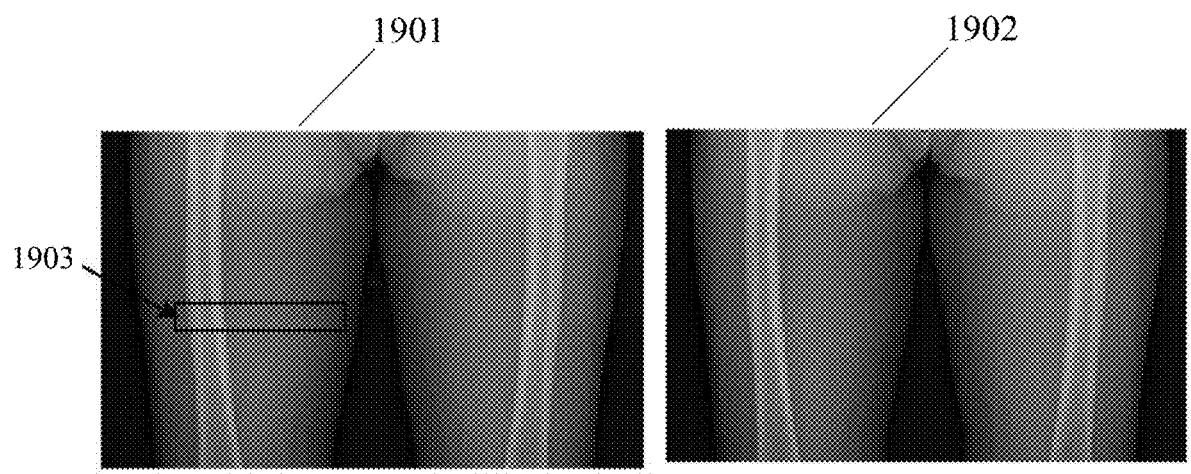
FIG. 19A  FIG. 19B

2000

2010

2500C

DEVICES, SYSTEMS, AND METHODS FOR IMAGE STITCHING

CROSS-REFERENCE TO RELATED APPLICATIONS

This application is a Continuation of International Application No. PCT/CN2019/090025, filed on Jun. 4, 2019, which claims priority to Chinese Patent Application No. 201810562311.5, filed on Jun. 4, 2018, Chinese Patent Application No. 201811493215.6, filed on Dec. 7, 2018, Chinese Patent Application No. 201810864201.4, filed on Aug. 1, 2018, and Chinese Patent Application No. 201810865608.9, filed on Aug. 1, 2018, the contents of each of which are incorporated herein by reference.

TECHNICAL FIELD

The present disclosure generally relates to image processing, and more particularly, systems and methods for image stitching.

BACKGROUND

Medical imaging techniques, such as an X-ray imaging technique, a magnetic resonance imaging (MRI) technique, a computed tomography (CT) imaging technique, or the like, are widely used for disease diagnosis. In some occasions, during a scan or a treatment using a medical imaging technique, a plurality of images of different portions of a region of interest (ROI) may be acquired, and the images may need to be stitched to generate a stitched image including the whole ROI. Therefore, it is desired to provide effective devices, systems, and methods for image stitching, thereby improving the quality of the stitched image.

SUMMARY

According to an aspect of the present disclosure, a system for image stitching is provided. The system may include at least one storage device including a set of instructions and at least one processor configured to communicate with the at least one storage device. When executing the set of instructions, the at least one processor may be configured to direct the system to perform the following operations. The system may obtain a reference image of a first portion of a subject and a target image of a second portion of the subject. The first portion and the second portion may at least partially overlap with each other. The system may determine at least one pair of feature points based on a preliminary registration accuracy. Each pair of the feature points may include a reference feature point in the reference image and a target feature point in the target image that matches the reference feature point. The system may also determine an updated pair of feature points for each of the at least one pair based on a superior registration accuracy and a neighboring region of the target feature point of the pair. The updated pair may include the reference feature point of the pair and an updated target feature point in the target image. The superior registration accuracy may be higher than the preliminary registration accuracy. The system may further generate a stitched image of the reference image and the target image based on the at least one updated pair.

In some embodiments, the preliminary registration accuracy may be a pixel-level accuracy, and the superior registration accuracy may be a subpixel-level accuracy.

In some embodiments, the system may perform one or more iterations to determine an updated pair of feature points for a pair of feature points. Each current iteration of the one or more iterations may include determining a plurality of interpolation points in a neighboring region of the target feature point in the current iteration, and determining a similarity degree between the interpolation point and the reference feature point of the pair for each of the plurality of interpolation points. Each current iteration may further include selecting an interpolation point that has the highest similarity degree with the reference feature point among the plurality of interpolation points, and determining whether the selected interpolation point satisfies a termination condition corresponding to the current iteration. Each current iteration may also include designating the selected interpolation point as the updated target feature point in response to a determination that the selected interpolation point satisfies the termination condition in the current iteration. In some embodiments, the termination condition may include that the selected interpolation point achieves the superior registration accuracy corresponding to the current iteration and/or that a similarity degree between the selected interpolation point and the reference feature point is within a similarity range corresponding to the current iteration.

In some embodiments, in response to a determination that the selected interpolation point does not satisfy the termination condition corresponding to the current iteration, each current iteration may also include designating the selected interpolation point as a target feature point in a next iteration, updating the termination condition, and designating the updated termination condition as a termination condition corresponding to the next iteration. The updated termination condition may include an updated superior registration accuracy higher than the superior registration accuracy corresponding to the current iteration.

In some embodiments, each current iteration may further include determining the neighboring region of the target feature point in the current iteration based on the superior registration accuracy corresponding to the current iteration.

In some embodiments, to generate a stitched image of the reference image and target image, the system may generate a preliminary stitched image by combining the target image and the reference image based on the at least one updated pair. The preliminary stitched image may include a seam. The system may also generate the stitched image by removing the seam from the preliminary stitched image.

In some embodiments, the system may be further directed to obtain a preliminary reference image of the first portion of the subject and a preliminary target image of the second portion of the subject. Each of the preliminary reference image and the preliminary target image may include at least a portion of a ruler. The system may process the image by removing the ruler from the image for each image of the preliminary reference image and the preliminary target image. The system may also designate the processed preliminary reference image as the reference image, and designate the processed preliminary target image as the target image.

In some embodiments, for each image of the preliminary reference image and the preliminary target image, the system may perform the following operations to process the image by removing the ruler from the image. The system obtain at least one feature value of at least one feature of the ruler. The at least one feature may include at least an identification feature. The system may further identify the ruler in the image based on the feature value of the identification feature, and process the image by removing the identified ruler from the image.

In some embodiments, the identification feature may include a positioning feature and a matching feature. To identify the ruler from the image, the system may determine a preliminary region representing the ruler in the image based on the feature value of the positioning feature, and identify the ruler from the image based on the preliminary region and the feature value of the matching feature.

In some embodiments, the ruler may have a scale axis. The positioning feature may include a ruler width of the ruler and a feature relating to the scale axis. To determine a preliminary region representing the ruler in the image, the system may determine a position of the scale axis in the image based on the feature value of the feature relating to the scale axis, and determine the preliminary region representing the ruler in the image based on the position of the scale axis and the feature value of the ruler width.

In some embodiments, to determine a position of the scale axis in the image, the system may transform the image into a binary image, identify one or more straight lines in the binary image, and determine the position of the scale axis in the image based on the one or more straight lines and the feature value of the feature relating to the scale axis.

In some embodiments, the ruler may include one or more numbers. The matching feature may include a feature relating to the one or more numbers. To identify the ruler from the image based on the preliminary region and the feature value of the matching feature, the system may identify at least one number of the one or more numbers in the preliminary region, and identify the ruler from the image based on the at least one number and the feature value of the feature relating to the one or more numbers.

In some embodiments, the at least one feature may further include a validation feature different from the identification feature. To process the image by removing the identified ruler from the image, the system may determine whether the identification of the ruler is valid based on the identified ruler and the feature value of the validation feature. The system may also remove the identified ruler in response to a determination that the identification of the ruler is valid.

In some embodiments, the ruler may include one or more scale lines. The validation feature may include a feature relating to the one or more scale lines. To determine whether the identification of the ruler is valid, the system may identify at least one scale line from the image, and determine whether the identification of the ruler is valid based on the identified at least one scale line and the feature value of the feature relating to the one or more scale lines.

In some embodiments, to obtain at least one feature value of at least one feature of the ruler, the system may obtain a template image of the ruler, and generate a binary template image of the template image by transforming the template image. The system may further generate a projection image of the binary template image by projecting the binary template image in a predetermined direction, and determine the at least one feature value of the at least one feature of the ruler based on the projection image.

In some embodiments, to generate a projection image of the binary template image in a predetermined direction, the system may generate a plurality of rotated binary template images. Each rotated binary template image may be generated by rotating the binary template image by a degree. For each of the plurality of rotated binary template images, the system may further generate a candidate projection image of the rotated binary template image by projecting the rotated binary template image in the predetermined direction, and select the projection image from the candidate projection images.

According to another aspect of the present disclosure, an X-ray imaging system is provided. The X-ray imaging system may include an X-ray imaging device, at least one storage device including a set of instructions, and at least one processor configured to communicate with the at least one storage device. The X-ray imaging device may include an X-ray source, a detector, and a control device configured to control a movement of the X-ray source and the detector. When executing the set of instructions, the at least one processor may be configured to direct the system to perform the following operations. The system may acquire a first image of a first portion of a subject using the X-ray imaging device. The X-ray source may be located at a first position and the detector may be located at a second position during the acquisition of the first image. The system may actuate the control device to control the movement of the X-ray source and the detector such that the X-ray source moves from the first position to a third position and the detector moves from the second position to a fourth position. The system may acquire a second image of a second portion of the subject using the X-ray imaging device. The X-ray source may be located at a third position and the detector may be located at the fourth position during the acquisition of the second image. The first portion and the second portion may have an overlapping portion. The at least one processor may direct the system to generate a stitched image based on the first image and the second image. During the acquisition of the first image, a first set of X-rays emitted by the X-ray source may pass through the overlapped portion. The first set may have a first range of incidence angles with respect to the detector. During the acquisition of the second image, a second set of X-rays emitted by the X-ray source may pass through the overlapping portion. The second set may have a second range of incidence angles with respect to the detector. The first range and the second range may at least partially overlap with each other.

In some embodiments, the X-ray imaging device may further include a gantry, a first arm, and a second arm. The first arm may have a first end mechanically connected to the gantry and a second end mechanically connected to the detector. The second arm may have a third end mechanically connected to the gantry and a fourth end mechanically connected to the X-ray source.

In some embodiments, the X-ray imaging device may further include one or more motion control devices. The control device may be configured to control the movement of the X-ray source and the detector via the one or more motion control devices. The one or more motion control devices may include at least one of a first motion control device, a second motion control device, a third motion control device, a fourth motion control device, or a fifth motion control device. The first motion control device may be mounted between the first end and the first arm configured to control a first movement of the first arm with respect to the gantry. The second motion control device may be mounted between the second end and the detector configured to control a second movement of the detector with respect to the first arm. The third motion control device may be mounted between the first arm and the second arm configured to control a third movement of the first arm with respect to the second arm. The fourth motion control device may be mounted between the fourth end and the X-ray source configured to control a fourth movement of the X-ray source with respect to the second arm. The fifth motion control device may be mounted between the third end and the second arm configured to control a fifth movement of the second arm with respect to the gantry.

In some embodiments, the first arm and the second arm may constitute an integral arm.

In some embodiments, the X-ray imaging device may further include a status control mechanism configured to control a status of the X-ray imaging device. The X-ray imaging device may have a first status under which the first arm is immovably connected to the second arm and a second status under which the first arm is movably connected to the second arm.

In some embodiments, to generate a stitched image based on the first image and the second image, the system may designate the first image as a reference image, and designate the second image as a target image. The system may determine at least one pair of feature points based on a preliminary registration accuracy. Each pair may include a reference feature point in the reference image and a target feature point in the target image matching the reference feature point. For each of the at least one pair, the system may determine an updated pair of feature points based on a superior registration accuracy and a neighboring region of the target feature point of the pair. The updated pair may include the reference feature point in the reference image and an updated target feature point in the target image. The superior registration accuracy may be higher than the preliminary registration accuracy. The system may generate the stitched image based on the reference image, the target image, and the at least one updated pair.

In some embodiments, each of the first image and the second image may include at least a portion of a ruler. To generate a stitched image based on the first image and the second image, the system may process the image by removing the ruler from the image for each image of the first image and the second image. The system may generate the stitched image based on the processed first image and the processed second image.

According to yet another aspect of the present disclosure, a method may be provided. The method may be implemented on a computing device having at least one processor and at least one storage device for image stitching. The method may include obtaining a reference image of a first portion of a subject and a target image of a second portion of the subject. The first portion and the second portion may at least partially overlap with each other. The method may also include determining at least one pair of feature points based on a preliminary registration accuracy. Each pair may include a reference feature point in the reference image and a target feature point in the target image that matches the reference feature point. For each of the at least one pair, the method may further include determining an updated pair of feature points based on a superior registration accuracy and a neighboring region of the target feature point of the pair. The updated pair may include the reference feature point of the pair and an updated target feature point in the target image. The superior registration accuracy may be higher than the preliminary registration accuracy. The method may further include generating a stitched image of the reference image and the target image based on the at least one updated pair.

According to yet another example, a method implemented on an X-ray imaging device and a computing device may be provided. The X-ray imaging device may include an X-ray source, a detector, and a control device configured to control a movement of the X-ray source and the detector. The computing device may have at least one processor and at least one storage device. The method may include acquiring a first image of a first portion of a subject using the X-ray imaging device. The X-ray source may be located at a first position and the detector may be located at a second position during the acquisition of the first image. The method may also include actuating the control device to control the movement of the X-ray source and the detector such that the X-ray source moves from the first position to a third position and the detector moves from the second position to a fourth position. The method may further include acquiring a second image of a second portion of the subject using the X-ray imaging device. The X-ray source may be located at the third position and the detector may be located at the fourth position during the acquisition of the second image. The first portion and the second portion may have an overlapping portion. The at least one processor may generate a stitched image based on the first image and the second image. During the acquisition of the first image, a first set of X-rays emitted by the X-ray source may pass through the overlapped portion. The first set may have a first range of incidence angles with respect to the detector. During the acquisition of the second image, a second set of X-rays emitted by the X-ray source may pass through the overlapping portion. The second set may have a second range of incidence angles with respect to the detector. The first range and the second range may at least partially overlap with each other.

According to yet another aspect of the present disclosure, a non-transitory computer readable medium is provided. The non-transitory computer readable medium may include a set of instructions for image stitching. When executed by at least one processor, the set of instructions may direct the at least one processor to effectuate a method. The method may include obtaining a reference image of a first portion of a subject and a target image of a second portion of the subject. The first portion and the second portion may at least partially overlap with each other. The method may also include determining at least one pair of feature points based on a preliminary registration accuracy. Each pair may include a reference feature point in the reference image and a target feature point in the target image that matches the reference feature point. For each of the at least one pair, the method may further include determining an updated pair of feature points based on a superior registration accuracy and a neighboring region of the target feature point of the pair. The updated pair may include the reference feature point of the pair and an updated target feature point in the target image. The superior registration accuracy may be higher than the preliminary registration accuracy. The method may further include generating a stitched image of the reference image and the target image based on the at least one updated pair.

According to yet another aspect of the present disclosure, a system for image stitching is provided. The system may include an obtaining module, a determination module, and a generation module. The obtaining module may be configured to obtain a reference image of a first portion of a subject and a target image of a second portion of the subject. The first portion and the second portion may at least partially overlap with each other. The determination module may be configured to determine at least one pair of feature points based on a preliminary registration accuracy. Each pair may include a reference feature point in the reference image and a target feature point in the target image that matches the reference feature point. For each of the at least one pair, the determination module may be further configured to determine an updated pair of feature points based on a superior registration accuracy and a neighboring region of the target feature point of the pair. The updated pair may include the reference feature point of the pair and an updated target feature point in the target image. The superior registration accuracy may be higher than the preliminary registration accuracy. The generation module may be configured to generate a stitched image of the reference image and the target image based on the at least one updated pair.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIGS. 5A to 5J are schematic diagrams illustrating an exemplary X-ray imaging device according to some embodiments of the present disclosure;

FIGS. 6A to 6I are schematic diagrams illustrating an X-ray imaging device according to some embodiments of the present disclosure;

FIGS. 8A to 8D are schematic diagrams illustrating an exemplary X-ray imaging device according to some embodiments of the present disclosure;

FIG. 17 illustrates an exemplary target image and an exemplary reference image according to some embodiments of the present disclosure;

FIG. 18 illustrates a pair of feature points and an updated pair of feature points in the target image and the reference image of FIG. 17 according to some embodiments of the present disclosure;

FIG. 19A illustrates a preliminary stitched image of the target image and the reference image of FIG. 17 according to some embodiments of the present disclosure;

FIG. 19B illustrates an exemplary stitched image generated by removing a seam from the preliminary stitched image in FIG. 19A according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Figure 2:
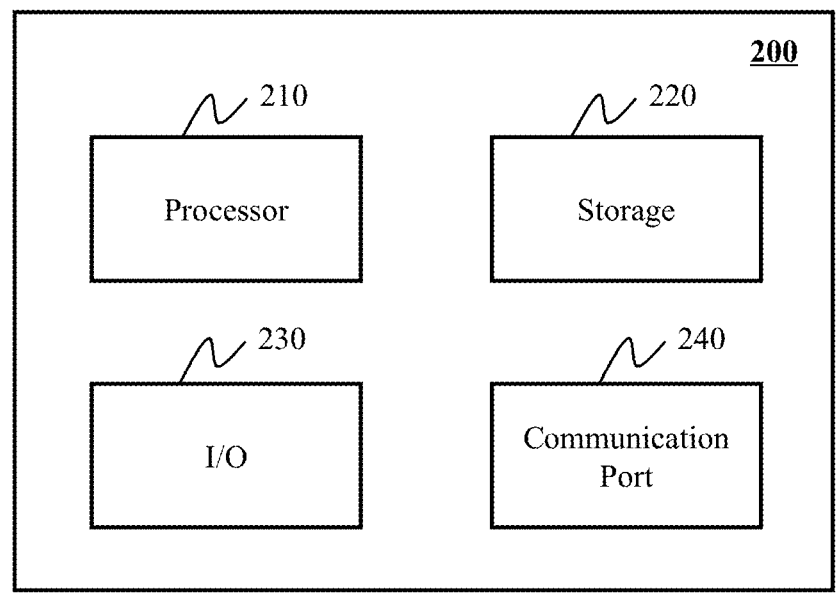
FIG. 2 is a schematic diagram illustrating hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items. The term "image" in the present disclosure is used to collectively refer to image data (e.g., scan data, projection data) and/or images of various forms, including a two-dimensional (2D) image, a three-dimensional (3D) image, a four-dimensional (4D), etc. The term "pixel" and "voxel" in the present disclosure are used interchangeably to refer to an element of an image.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention.

Spatial and functional relationships between elements (for example, between layers) are described using various terms, including "connected," "engaged," "interfaced," and "coupled." Unless explicitly described as being "direct," when a relationship between first and second elements is described in the present disclosure, that relationship includes a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

An aspect of the present disclosure relates to systems and methods for image stitching. The systems may perform the methods to obtain a reference image of a first portion of a subject and a target image of a second portion of the subject. The first portion and the second portion may at least partially overlap with each other. The systems may also perform the methods to determine at least one pair of feature points based on a preliminary registration accuracy. Each pair may include a reference feature point in the reference image and a target feature point in the target image that matches the reference feature point. For each of the at least one pair, the systems may also perform the methods to determine an updated pair of feature points based on a superior registration accuracy and a neighboring region of the target feature point of the pair. The updated pair may include the reference feature point of the pair and an updated target feature point in the target image. The superior registration accuracy may be higher than the preliminary registration accuracy. The systems may further perform the methods to generate a stitched image of the reference image and the target image based on the at least one updated pair. According to some embodiments of the present disclosure, the preliminary registration accuracy may be a pixel-level accuracy, and the superior registration accuracy may be a subpixel-level accuracy. The systems and methods may achieve image stitching under a sub-pixel level, thereby improving the accuracy of image stitching. Moreover, by determining at least one pair of feature points based on a preliminary registration accuracy and subsequently updating the at least one pair of feature points based on a superior registration accuracy may improve the efficiency of the process by reducing, e.g., the processing time, the computational complexity and/or cost, etc.

Figure 1:
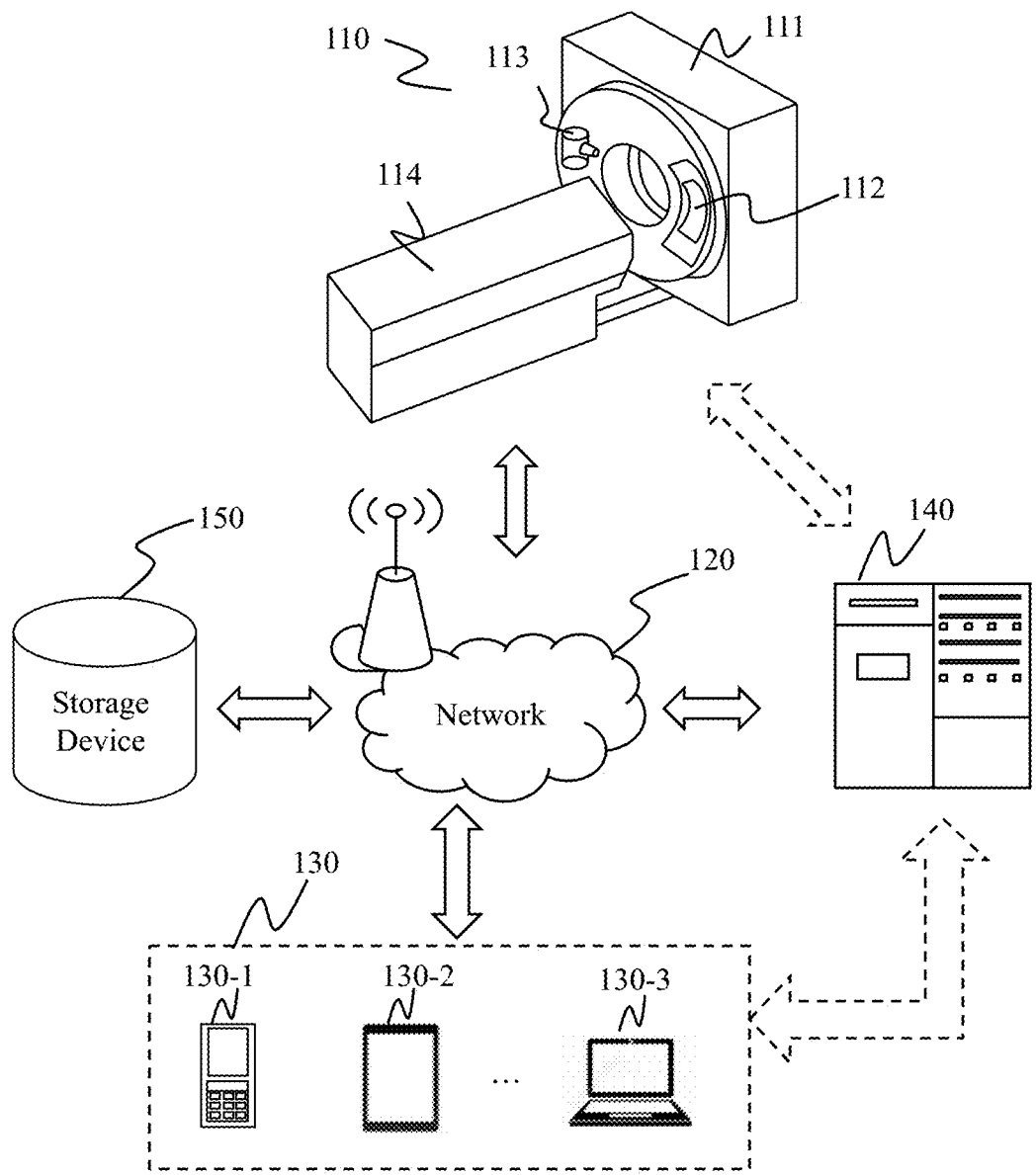
FIG. 1 is a schematic diagram illustrating an exemplary imaging system according to some embodiments of the present disclosure.

FIG. 1 is a schematic diagram illustrating an exemplary imaging system 100 according to some embodiments of the present disclosure. In some embodiments, the imaging system 100 may be include a single modality imaging system and/or a multi-modality imaging system. The single modality imaging system may include, for example, an ultrasound imaging system, an X-ray imaging system, an computed tomography (CT) system, a magnetic resonance imaging (MRI) system, an ultrasonography system, a positron emission tomography (PET) system, an optical coherence tomography (OCT) imaging system, an ultrasound (US) imaging system, an intravascular ultrasound (IVUS) imaging system, a near infrared spectroscopy (NIRS) imaging system, or the like, or any combination thereof. The multi-modality imaging system may include, for example, an X-ray imaging-magnetic resonance imaging (X-ray-MRI) system, a positron emission tomography-X-ray imaging (PET-X-ray) system, a single photon emission computed tomography-magnetic resonance imaging (SPECT-MRI) system, a positron emission tomography-computed tomography (PET-CT) system, a C-arm system, a digital subtraction angiography-magnetic resonance imaging (DSA-MRI) system, etc.

As illustrated in FIG. 1, the imaging system 100 may include an imaging device 110, a network 120, one or more terminals 130, a processing device 140, and a storage device 150. The components in the imaging system 100 may be connected in one or more of various ways. Merely by way of example, the imaging device 110 may be connected to the processing device 140 through the network 120. As another example, the imaging device 110 may be connected to the processing device 140 directly as indicated by the bi-directional arrow in dotted lines linking the imaging device 110 and the processing device 140. As a further example, the storage device 150 may be connected to the processing device 140 directly or through the network 120. As still a further example, the terminal 130 may be connected to the processing device 140 directly (as indicated by the bi-directional arrow in dotted lines linking the terminal 130 and the processing device 140) or through the network 120.

In some embodiments, the imaging device 110 may include a CT scanner, a digital radiography (DR) scanner, an X-ray scanner, a DSA scanner, a dynamic spatial reconstructor (DSR) scanner, a multi-modality scanner, or the like, or a combination thereof. Exemplary multi-modality scanners may include a CT-PET scanner, a CT-MRI scanner, etc.

For illustration purposes, an X-ray imaging device is described as an example. The imaging device 110 may include a gantry 111, a detector 112, an X-ray source 113, and a scanning table 114. The detector 112 and the X-ray source 113 may be oppositely mounted on the gantry 111. A subject may be placed on the scanning table 114 and moved into a detection tunnel (e.g., a space between the detector 112 and the X-ray source 113) of the imaging device 110. The subject may be biological or non-biological. Merely by way of example, the subject may include a patient, a man-made subject, etc. As another example, the subject may include a specific portion, organ, and/or tissue of the patient. For example, the subject may include head, brain, neck, body, shoulder, arm, thorax, cardiac, stomach, blood vessel, soft tissue, knee, feet, or the like, or any combination thereof. In the present disclosure, "subject" and "object" are used interchangeably.

The X-ray source 113 may emit radiation rays to scan the subject that is placed on the scanning table 114. The radiation rays may include X-rays, y-rays, a-rays, ultraviolet, laser, neutron, proton, or the like, or a combination thereof. The detector 112 may receive the radiation rays passed through the subject. In some embodiments, the detector 112 may include a plurality of detector units, which may be arranged in a channel direction and a row direction. The detector 112 may include a scintillation detector (e.g., a cesium iodide detector) or a gas detector.

The network 120 may facilitate exchange of information and/or data. In some embodiments, one or more components of the imaging system 100 (e.g., the imaging device 110, the terminal 130, the processing device 140, or the storage device 150) may send information and/or data to another component(s) of the imaging system 100 via the network 120. For example, the processing device 140 may obtain, via the network 120, an image from the storage device 150. In some embodiments, the network 120 may be any type of wired or wireless network, or combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, an optical fiber network, a telecommunications network, an intranet, an Internet, a local area network (LAN), a wide area network (WAN), a wireless local area network (WLAN), a metropolitan area network (MAN), a wide area network (WAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired or wireless network access points such as base stations and/or internet exchange points through which one or more components of the imaging system 100 may be connected to the network 120 to exchange data and/or information.

The terminal 130 include a mobile device 130-1, a tablet computer 130-2, a laptop computer 130-3, or the like, or any combination thereof. In some embodiments, the mobile device 130-1 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footgear, eyeglasses, a helmet, a watch, clothing, a backpack, an accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass, an Oculus Rift, a HoloLens, a Gear VR, etc. In some embodiments, the terminal 130 may remotely operate the imaging device 110. In some embodiments, the terminal 130 may operate the imaging device 110 via a wireless connection. In some embodiments, the terminal 130 may receive information and/or instructions inputted by a user, and send the received information and/or instructions to the imaging device 110 or to the processing device 140 via the network 120. In some embodiments, the terminal 130 may receive data and/or information from the processing device 140. In some embodiments, the terminal 130 may be omitted or be part of the processing device 140.

In some embodiments, the processing device 140 may process data obtained from the imaging device 110, the terminal 130, or the storage device 150. For example, the processing device 140 may process a plurality of images (e.g., a reference image, a target image, etc.) obtained from the imaging device 110 and/or the storage device 150 to stitch the images. The processing device 140 may be a central processing unit (CPU), a digital signal processor (DSP), a system on a chip (SoC), a microcontroller unit (MCU), or the like, or any combination thereof.

In some embodiments, the processing device 140 may be a single server or a server group. The server group may be centralized or distributed. In some embodiments, the processing device 140 may be local or remote. For example, the processing device 140 may access information and/or data stored in the imaging device 110, the terminal 130, and/or the storage device 150 via the network 120. As another example, the processing device 140 may be directly connected to the imaging device 110, the terminal 130, and/or the storage device 150, to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 200 having one or more components illustrated in FIG. 2 in the present disclosure.

The storage device 150 may store data and/or instructions. In some embodiments, the storage device 150 may store data obtained from the terminal 130 and/or the processing device 140. For example, the storage device 150 may store one or more images obtained from the processing device 140 and/or the imaging device 110. In some embodiments, the storage device 150 may store data and/or instructions that the processing device 140 may execute or use to perform exemplary methods described in the present disclosure. For example, the storage device 150 may store data and/or instructions that the processing device 140 may execute or use to generate a stitched image. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components of the imaging system 100 (e.g., the terminal 130, the processing device 140). One or more components of the imaging system 100 may access the data or instructions stored in the storage device 150 via the network 120. In some embodiments, the storage device 150 may be directly connected to or communicate with one or more components of the imaging system 100 (e.g., the terminal 130, the processing device 140). In some embodiments, the storage device 150 may be part of the processing device 140.

It should be noted that the above description of the imaging system 100 is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the imaging system 100 may include one or more additional components. Additionally or alternatively, one or more components of the imaging system 100 described above may be omitted. As another example, two or more components of the imaging system 100 may be integrated into a single component. In some embodiments, the imaging system 100 may include a control device configured to control the imaging device 110. The control device may be an independent device, or be part of the imaging device 110 or the processing device 140.

FIG. 2 is a schematic diagram illustrating hardware and/or software components of an exemplary computing device 200 according to some embodiments of the present disclosure. The computing device 200 may be used to implement any component of the imaging system 100 as described herein. For example, the processing device 140 and/or the terminal 130 may be implemented on the computing device 200, respectively, via its hardware, software program, firmware, or a combination thereof. Although only one such computing device is shown, for convenience, the computer functions relating to the imaging system 100 as described herein may be implemented in a distributed fashion on a number of similar platforms, to distribute the processing load.

As illustrated in FIG. 2, the computing device 200 may include a processor 210, a storage 220, an input/output (I/O) 230, and a communication port 240. The processor 210 may execute computer instructions (program code) and, when executing the instructions, cause the processing device 140 to perform functions of the processing device 140 in accordance with techniques described herein. The computer instructions may include, for example, routines, programs, objects, components, signals, data structures, procedures, modules, and functions, which perform particular functions described herein. In some embodiments, the processor 210 may process data and/or images obtained from the imaging device 110, the terminal 130, the storage device 150, and/or any other component of the imaging system 100. For example, the processor 210 may obtain a plurality of images from the storage device 150, and stitch the images to generate a stitched image. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both process A and process B, it should be understood that process A and process B may also be performed by two or more different processors jointly or separately in the computing device 200 (e.g., a first processor executes process A and a second processor executes process B, or the first and second processors jointly execute processes A and B).

The storage 220 may store data/information obtained from the imaging device 110, the terminal 130, the storage device 150, or any other component of the imaging system 100. In some embodiments, the storage 220 may include a mass storage device, a removable storage device, a volatile read-and-write memory, a read-only memory (ROM), or the like, or any combination thereof. In some embodiments, the storage 220 may store one or more programs and/or instructions to perform exemplary methods described in the present disclosure. For example, the storage 220 may store a program (e.g., in the form of computer-executable instructions) for the processing device 140 to control a movement of the X-ray source 113 and/or the detector 112. As another example, the storage 220 may store a program (e.g., in the form of computer-executable instructions) for the processing device 140 to generate a stitched image.

The I/O 230 may input or output signals, data, and/or information. In some embodiments, the I/O 230 may enable user interaction with the processing device 140. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected to a network (e.g., the network 120) to facilitate data communications. The communication port 240 may establish connections between the processing device 140 and the imaging device 110, the terminal 130, or the storage device 150. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMAX, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
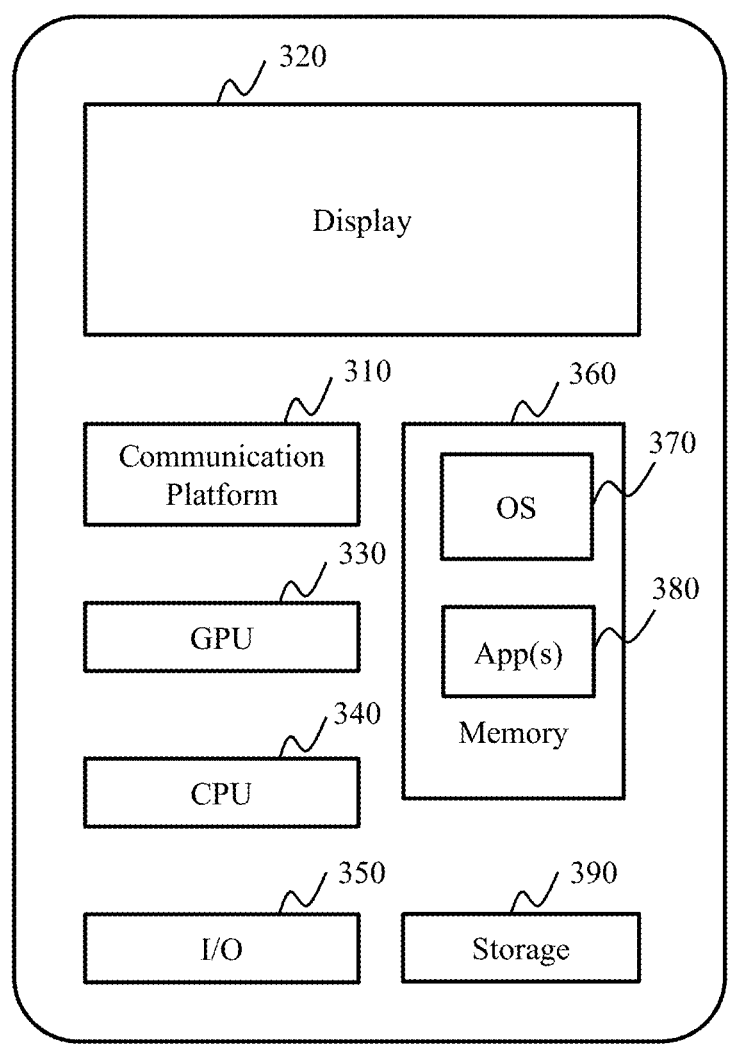
FIG. 3 is a schematic diagram illustrating hardware and/or software components of an exemplary mobile device according to some embodiments of the present disclosure.

FIG. 3 is a schematic diagram illustrating hardware and/or software components of a mobile device 300 according to some embodiments of the present disclosure. In some embodiments, the processing device 140 and/or the terminal 130 may be implemented on the mobile device 300. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to the imaging system 100 from the processing device 140. User interactions with the information stream may be achieved via the I/O 350 and provided to the processing device 140 and/or other components of the imaging system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate a high-quality image of a subject as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4:
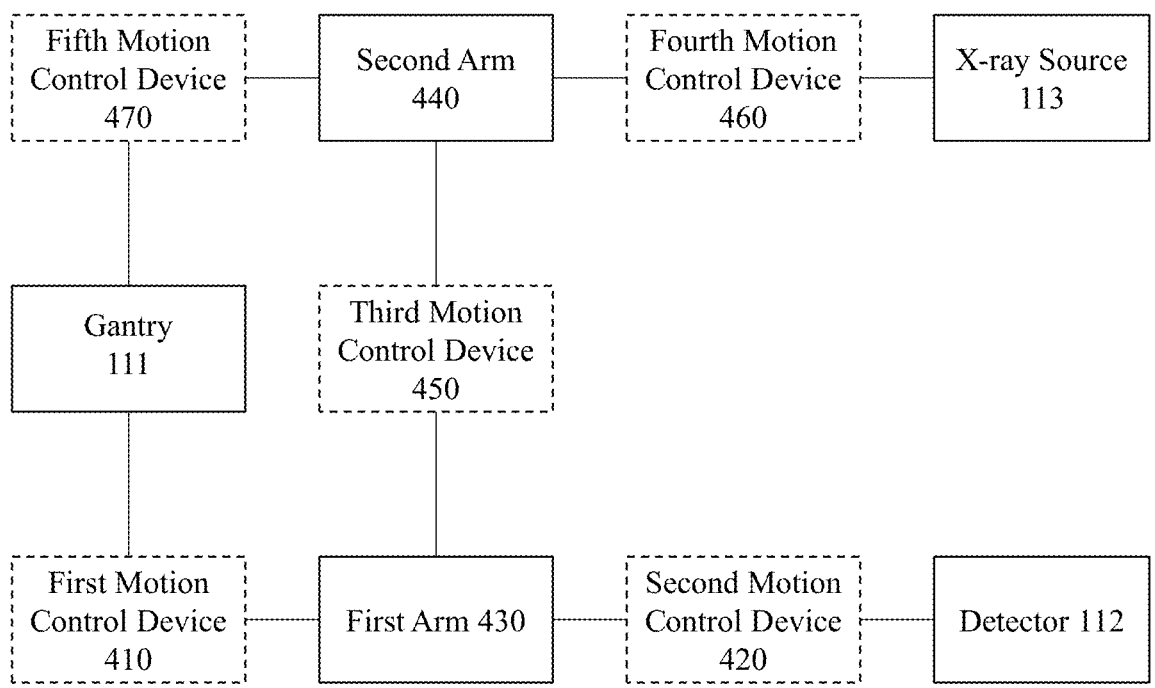
FIG. 4 is a schematic diagram illustrating an exemplary X-ray imaging device according to some embodiments of the present disclosure.

FIG. 4 is a schematic diagram illustrating an exemplary X-ray imaging device 400 according to some embodiments of the present disclosure. The X-ray imaging device 400 may be an exemplary embodiment of the imaging device 110 as described in connection with FIG. 1. The X-ray imaging device 400 may include the gantry 111, the detector 112, the X-ray source 113, a first arm 430, a second arm 440, and a control device (not shown in FIG. 4).

The gantry 111 may be configured to support one or more components of the X-ray imaging device 400. For example, the gantry 111 may be mechanically connected to and support the first arm 430 and the second arm 440. The first arm 430 may be configured to support the detector 112. For example, the first arm 430 may have a first end mechanically connected to the gantry 111 and a second end mechanically connected to the detector 112. The second arm 440 may be configured to support the X-ray source 113. For example, the second arm 440 may have a third end mechanically connected to the gantry 111 and a fourth end mechanically connected to the X-ray source 113. The control device may be configured to control the movement of the X-ray source 113 and/or the detector 112. In some embodiments, the control device may control the movement of the X-ray source 113 and/or the detector 112 via, for example, the first arm 430, the second arm 440, one or more motion control devices (e.g., a first motion control device 410, a second motion control device 420, a third motion control device 450, a fourth motion control device 460, and a fifth motion control device 470 as illustrated in FIG. 4), or any combination thereof.

As used herein, a mechanical connection between two elements may include a direct mechanical connection where no other intervening element is present between the two elements, and also an indirect relationship where one or more intervening elements are present (either spatially or functionally) between the two elements. For example, as shown in FIG. 4, the first motion control device 410 may be mounted between the gantry 111 and the first end of the first arm 430 to establish a mechanical connection between the first arm 430 and the gantry 111. The second motion control device 420 may be mounted between the detector 112 and the second end of the first arm 430 to establish a mechanical connection between the first arm 430 and the detector 112. The third motion control device 450 may be mounted between the first arm 430 and the second arm 440 to establish a mechanical connection between the first arm 430 and the second arm 440. The fourth motion control device 460 may be mounted between the fourth end of the second arm 440 and the X-ray source 113 to establish a mechanical connection between the second arm 440 and the X-ray source 113. The fifth motion control device 470 may be mounted between the gantry 111 and the third end of the second arm 440 to establish a mechanical connection between the gantry 111 and the second arm 440.

It should be noted that the above description regarding the connections between components of the X-ray imaging device 400 is merely provided for the purposes of illustration, and not intended to limit the scope of the present disclosure. One or more of the motion control devices may be omitted. Two components of the X-ray imaging device 400 connected to each via a motion control device may be connected to each other directly. For example, the first motion control device 410 may be omitted, and the first arm 430 may be mechanically connected to the gantry 111 directly. As another example, the fourth motion control device 460 may be omitted, and the second arm 440 may be mechanically connected to the X-ray source 113 directly. As yet another example, the third motion control device 450 may be omitted, and the first arm 430 and the second arm 440 may constitute an integral arm, such as a G-shape arm, a C-shape arm, or the like.

In some embodiments, a pair of connected components of the X-ray imaging device 400 may be relatively fixed and immovably connected to each other. Alternatively, a pair of connected components of the X-ray imaging device 400 may be movably connected to each other. Merely by way of example, the first arm 430 may be immovably or movably connected to the second arm 440. In some embodiments, the connection between a pair of connected components of the X-ray imaging device 400 may be variable. For example, the X-ray imaging device 400 may further include a status control mechanism configured to control the status of the X-ray imaging device 400 by, for example, controlling the connection between a pair of connected components of the X-ray imaging device 400. In some embodiments the X-ray imaging device 400 may have a first status under which the first arm 430 is immovably connected to the second arm 440, and a second status under which the first arm 430 is movably connected to the second arm 440. The status control mechanism may change a movable connection between the first arm 430 and the second arm 440 to an immovable connection, or vice versa, so as to control the status of the X-ray imaging device 400. In some embodiments, the status control mechanism may include a clutch, a screw, a slot, a nail, or the like, or any combination thereof.

In some embodiments, a movable connection between two components of the X-ray imaging device 400 may be achieved by a motion control device, such as any one of the first, second, third, fourth, and fifth motion control devices. For example, the first motion control device 410 may be configured to control a first movement of the first arm 430 with respect to the gantry 111. The second motion control device 420 may be configured to control a second movement of the detector 112 with respect to the first arm 430. The third motion control device 450 may be configured to control a third movement of the first arm 430 with respect to the second arm 440. The fourth motion control device 460 may be configured to control a fourth movement of the X-ray source 113 with respect to the second arm 440. The fifth motion control device 470 may be configured to control a fifth movement of the second arm 440 with respect to the gantry 111.

In some embodiments, a movement of a component of the X-ray imaging device 400 may include a translation movement, a rotation movement, or the like, or any combination thereof. Merely by way of example, the first movement of the first arm 430 may include a translation movement of the first arm 430 along a certain direction (e.g., a direction parallel with a table (not shown) of the X-ray imaging device 400), a rotation movement of the first arm 430 around a certain axis (e.g., an axis perpendicular to the table of the X-ray imaging device 400), or the like, or any combination thereof. In some embodiments, a movement of a certain component of the X-ray imaging device 400 may cause a movement of another component mechanically connected to the certain component. For instance, the first movement of the first arm 430 may cause a movement of the detector 112 and a movement of the second motion control device 420 (if any). As another example, the fifth movement of the second arm 440 may cause a movement of the X-ray source 113 and a movement of the fourth motion control device 460 (if any).

In some embodiments, a motion control device (e.g., any one of the first, second, third, fourth, and fifth motion control devices) may include any mechanism or combination of mechanisms to implement the functions thereof. For example, the motion control device may include a motor, a movement transmission mechanism, a decelerating mechanism, etc. In some embodiments, a motion control device (e.g., the first motion control device 410, the second motion control device 420, and/or the fifth motion control device 470) may include a sliding mechanism (e.g., a sliding rail) configured to drive a translation movement of a certain component connected to the motion control device. More descriptions regarding the sliding mechanism may be found elsewhere in the present disclosure. See, e.g., FIGS. 5A to 5J, and relevant descriptions thereof. In some embodiments, a motion control device (e.g., the first motion control device 410 and/or the fourth motion control device 460) may include a rotation mechanism (e.g., a rotation motor, a rotation shaft) configured to drive a rotation movement of a certain component connected to the motion control device. More descriptions regarding the rotation mechanism may be found elsewhere in the present disclosure. See, e.g., FIGS. 6A to 6I and relevant descriptions thereof.

In some embodiments, the control device may be communicatively connected to a motion control device and transmit a control signal to the motion control device, wherein the control signal may direct the motion control device to control the movement of a certain component connected to the motion control device. For example, the control device may transmit a first control signal to the first motion control device 410 and/or the second motion control device 420 so as to control a movement (e.g., a translation) of the detector 112. As another example, the control device may transmit a second control signal to the fourth motion control device 460 and/or the fifth motion control device 470 so as to control a movement (e.g., a rotation, a translation) of the X-ray source 113.

In some embodiments, the control device may include one or more control units, each of which may be configured to control one or more components of the X-ray imaging device 400. For example, the control device may include five control units, each of which corresponds to and controls one of the first, second, third, fourth, and fifth motion control devices independently. As another example, the control device may include a first control unit that controls the movement of the detector 112 and a second control unit that controls the movement of the X-ray source 113. Optionally, the control device may further include a third control unit that controls the first control unit and the second control unit so that the first and second control units operate in a coordinated manner. Exemplary control units and control signals may be found in Chinese Patent Application No. CN104287756B and its divisional application Chinese Patent Application No. CN106852697A, both titled "Methods and Devices for X-ray image Acquisition" and filed on Sep. 28, 2014. The entire contents of the above-referenced applications are hereby incorporated by reference. In some embodiments, the X-ray imaging device 400 may be used to acquire a plurality of images of different portions of a subject. For example, The X-ray imaging device 400 may be used to acquire a first image of a first portion of the subject, during which the X-ray source 113 and the detector 112 are located at a first position and a second position, respectively. The control device may control one or more of the first arm 430, the second arm 440, the third, fourth, and fifth motion control devices to move (e.g., rotate and/or translate) the X-ray source 113 from the first position to a third position. The control device may control one or more of the first arm 430, the second arm 440, the first, second, and third motion control device to move (e.g., translate) the detector 112 from the second position to a fourth position. The X-ray imaging device 400 may be caused to acquire a second image of a second portion of the subject, during which the X-ray source 113 and the detector 112 are located at the third position and the fourth position, respectively. In some embodiments, the first portion and the second portion may have an overlapping portion. A stitched image including both the first and second portions of the subject may be generated based on the first image and the second image. More descriptions regarding the first and second images may be found elsewhere in the present disclosure. See, e.g., FIG. 15 and relevant descriptions thereof.

Figure 5A:
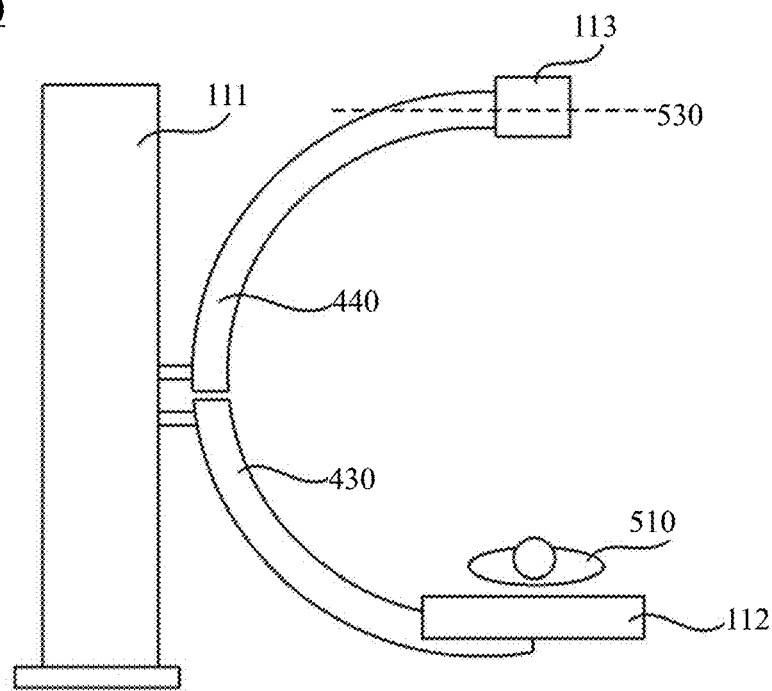
Figure 5B:
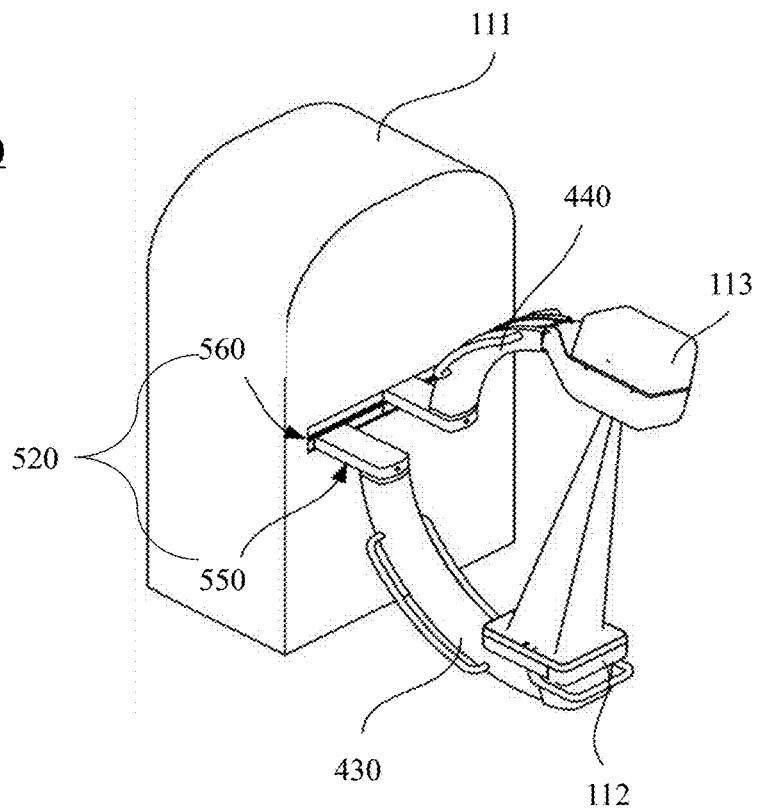
Figure 5C:
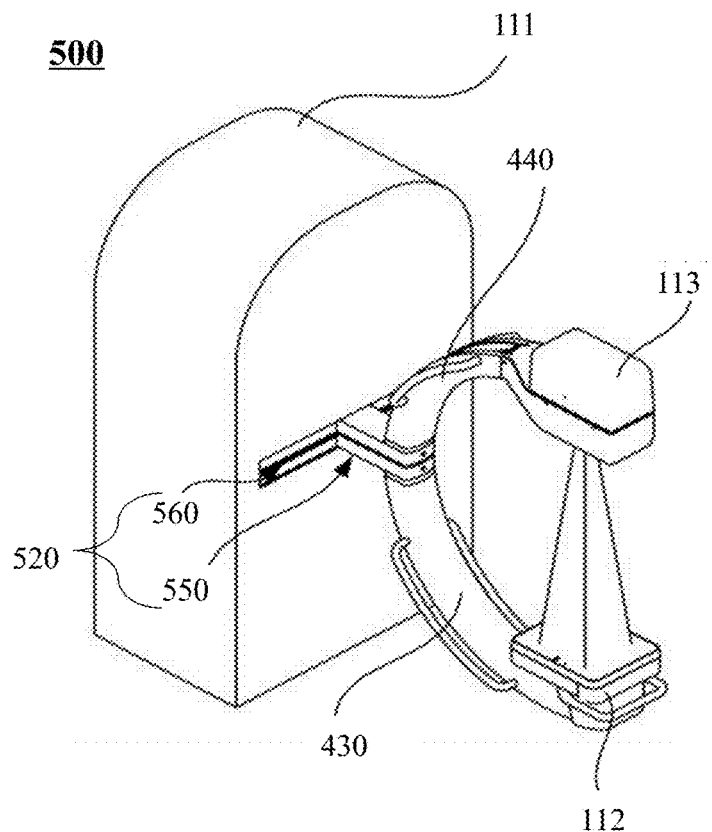
Figure 5D:
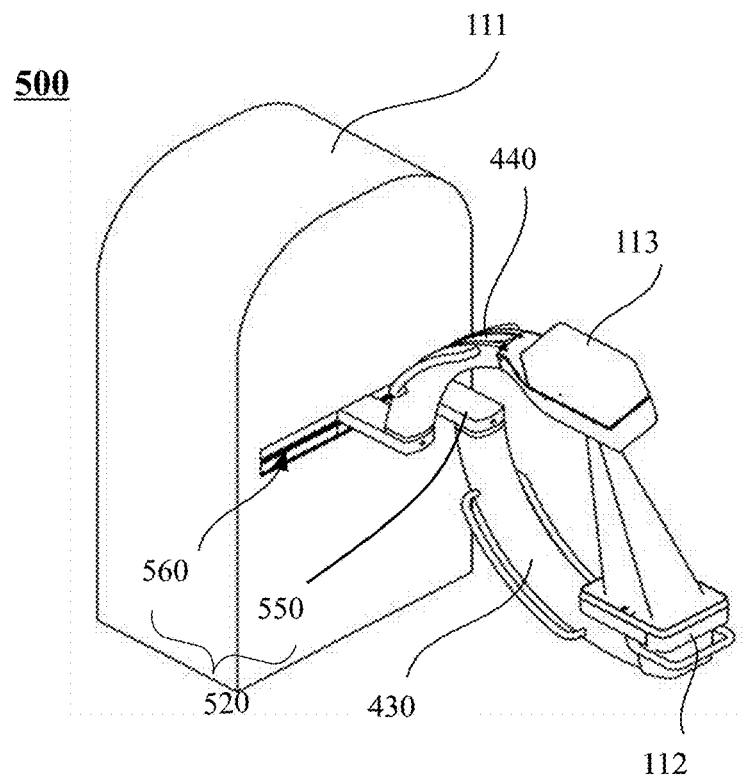
Figure 5H:
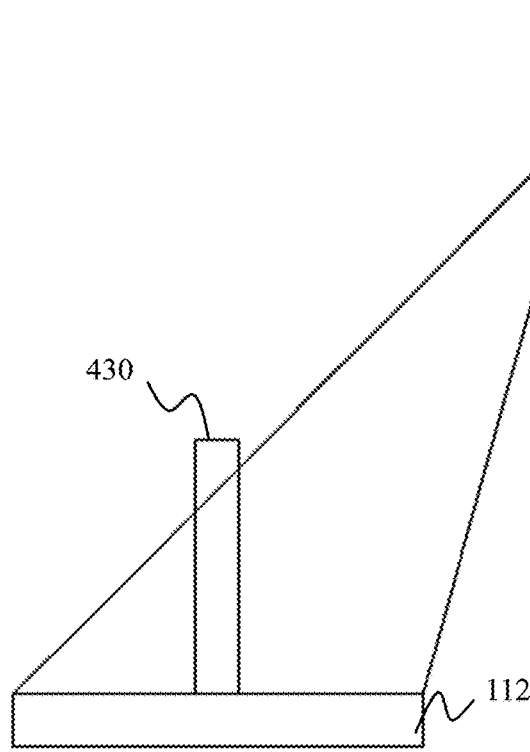
Figure 5I:
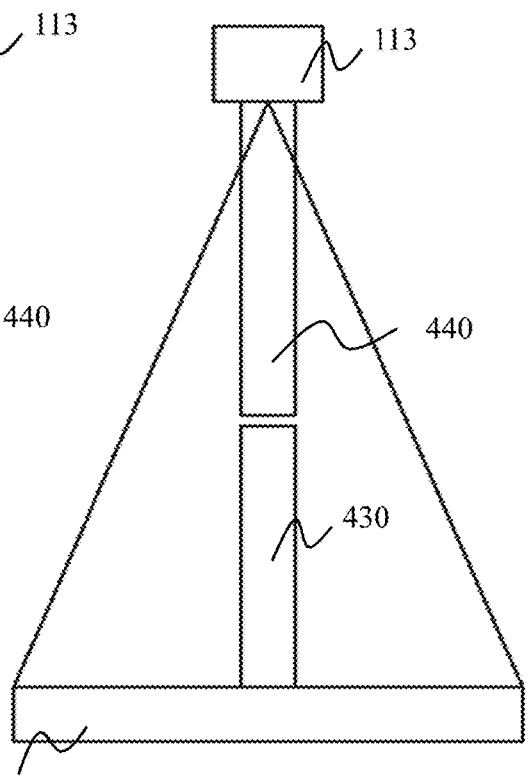
Figure 5J:
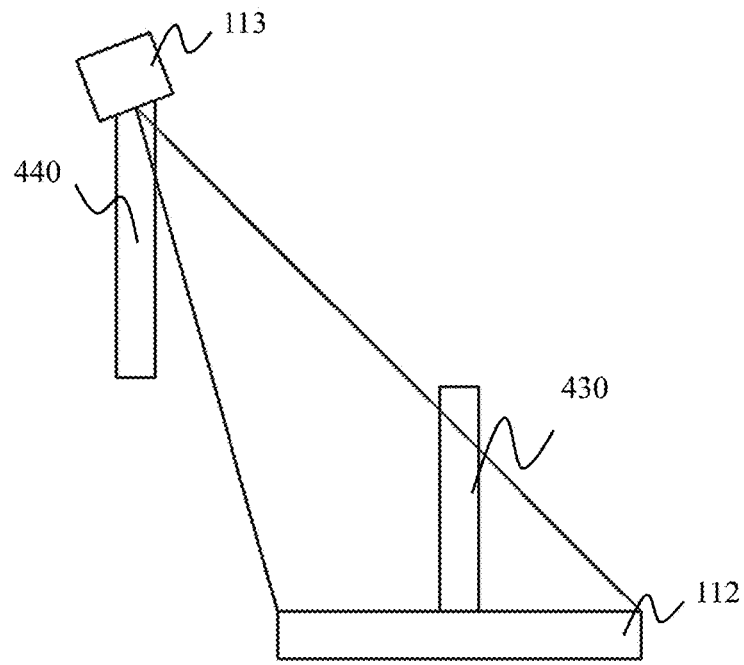

FIGS. 5A to 5J are schematic diagrams illustrating an exemplary X-ray imaging device 500 according to some embodiments of the present disclosure. The X-ray imaging device 500 is an exemplary embodiment of the X-ray imaging device 400 as described in connection with FIG. 4. The X-ray imaging device 500 may include the gantry 111, the X-ray source 113, the detector 112, the first arm 430, the second arm 440, and a first motion control device 520. FIG. 5A illustrates a side view of the X-ray imaging device 500. FIGS. 5B to 5D illustrate a perspective view of the X-ray imaging device 500. FIG. 5E to 5G illustrate a front view of the X-ray imaging device 500. FIGS. 5H to 5J illustrate exemplary movements of the detector 112 and the X-ray source 113 of the X-ray imaging device 500.

As shown in FIG. 5A, a subject 510 may be placed on a scanning table (e.g., the scanning table 114 not shown in FIG. 5A) during a process of imaging. The X-ray source 113 may emit radiation rays toward the subject 510. The detector 112 may receive radiation rays that pass through the subject 510.

In some embodiments, the X-ray source 113 may move to different positions to irradiate different portions of the subject as shown in FIGS. 5B to 5J. For example, the X-ray source 113 may rotate with respect to the second arm 440 around an axis 530 that is parallel with (or substantially parallel with) the detector 112 as shown in FIG. 5A. In some embodiments, the X-ray imaging device 500 may include a fourth motion control device (not shown in FIGS. 5A to 5J) (e.g., the fourth motion control device 460 as discussed in FIG. 4) that can drive the rotation of the X-ray source 113. In some embodiments, the fourth motion control device may include any mechanism that can drive the rotation of the X-ray source 113. For example, the fourth motion control device may induce a rotation shaft, a rotation motor, etc.

As shown in FIGS. 5B to 5J, during the rotation of the X-ray source 113, the detector 112 may translate to different positions to receive radiation rays. The translation of the detector 112 may be along a direction that is parallel with (or substantially parallel with) an extension direction of the subject from the head to the feet of the subject 510. In some embodiments, the translation of the detector 112 may be driven by the first motion control device 520, which is an exemplary embodiment of the first motion control device 410 as described in connection with FIG. 4. The first motion control device 520 may be configured to drive a translation of the first arm 430 respective to the gantry 111, wherein the translation of the first arm 430 may further drive the translation of the detector 112. The first motion control device 520 may include a first sliding rail 560, a first base 550, and a first driving device (not shown). The first sliding rail 560 may be mounted on the gantry 111 and configured to guide the translation of the first arm 430. For example, the extension direction of the first sliding rail 560 may be parallel with the extension direction of the subject 510, such that the first arm 430 and the detector 112 may translate along a direction that is parallel with the extension direction of the subject 510. The first sliding rail 560 may be configured as, for example, a rod, a groove, or any other suitable mechanism. Optionally, the first sliding rail 560 may be retractable or foldable. The first base 550 may match with the first sliding rail 560 and mechanically connected to the second arm 440 and the first sliding rail 560. The first driving device may be configured to drive the first base 550 to slide along the first sliding rail 560, so as to drive the movement of the first arm 430 and the detector 112. In some embodiments, the first driving device may include a stepping motor, a linear motor, an air cylinder, or the like. In some embodiments, the first driving device may be coupled to and controlled by a control device of the X-ray imaging device 500. For example, the control device may transmit a control signal to direct the first driving device to translate the first arm 430 in a specific direction for a specific distance.

Figure 6G:
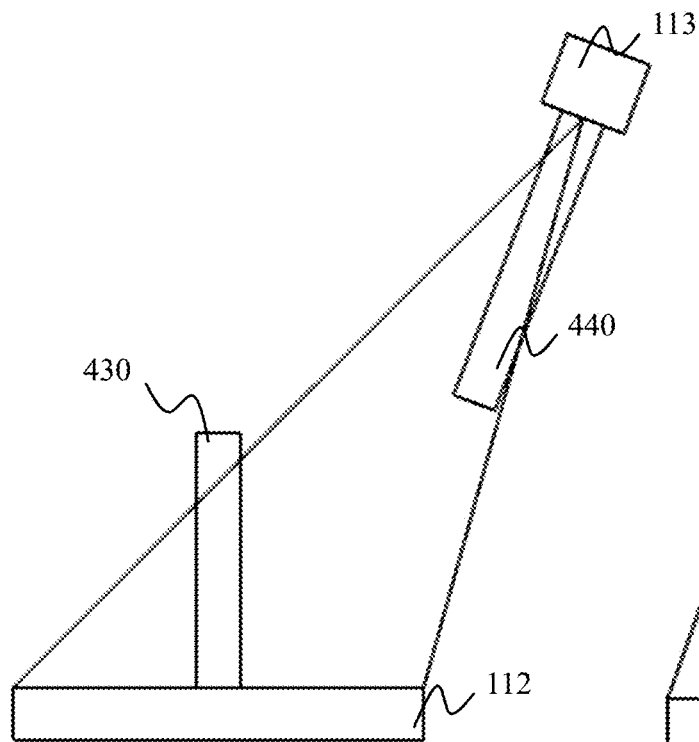
Figure 6H:
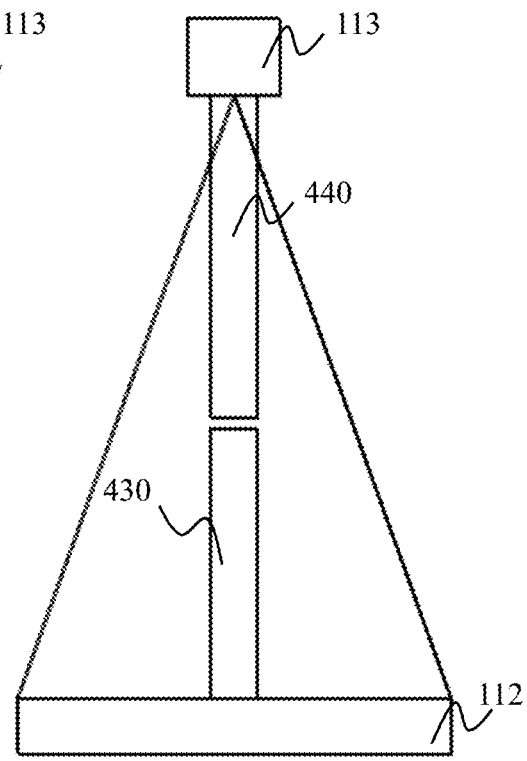
Figure 6I:
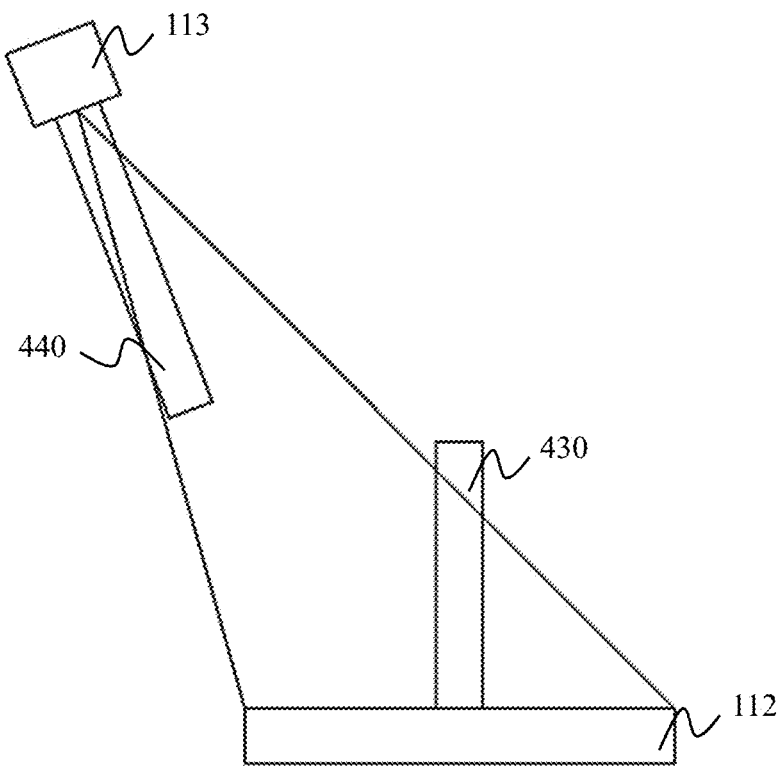

FIGS. 6A to 6I illustrate an X-ray imaging device 600 according to some embodiments of the present disclosure. The X-ray imaging device 600 may be an exemplary embodiment of the X-ray imaging device 400 as described in connection with FIG. 4. The X-ray imaging device 600 may include the gantry 111, the first arm 430, the second arm 440, the detector 112, the X-ray source 113, and the first motion control device 520. FIGS. 6A to 6C illustrate a perspective view of the X-ray imaging device 600. FIGS. 6D to 6F illustrate a front view of the X-ray imaging device 600. FIGS. 6G to 6I illustrate exemplary movements of the detector 112 and the X-ray source 113 of the X-ray imaging device 600.

The X-ray imaging device 600 may be similar to the X-ray imaging device 500 as described in FIGS. 5A to 5J, except for certain components or features. Similar to the X-ray imaging device 500, the detector 112 of the X-ray imaging device 600 may be translated to different positions during a scan via the first motion control device 520. Different from the X-ray imaging device 500, the movement of the X-ray source 113 may be driven by a movement of the second arm 440. As shown in FIGS. 6A to 6I, the second arm 440 may rotate respective to the gantry 111 around a specific axis (e.g., an axis parallel with or substantially parallel with the axis 530 as illustrated in FIG. 5A). The rotation of the second arm 440 may drive the X-ray source 113 to rotate.

In some embodiments, the rotation of the second arm 440 may be driven by a fifth motion control device (e.g., the fifth motion control device 470 as discussed in FIG. 4). The fifth motion control device may include any rotation mechanism that can drive the rotation of the second arm 440. For example, the fifth motion control device may include a rotation motor and a rotation shaft. The rotation motor may be mounted on the gantry 111. An end of the rotation shaft may be mechanically connected to an output interface of the rotation motor, and another end of the rotation shaft may be connected to the second arm 440. The rotation motor may drive the rotation shaft to rotate, and the rotation of the rotation shaft may further drive the second arm 440 to rotate. In some embodiments, during the rotation of the second arm 440, radiation rays emitted from the X-ray source 113 may irradiate different portions of a subject to be scanned. The detector 112 may be translated to different positions to receive radiation rays passing through the subject.

Figure 7A:
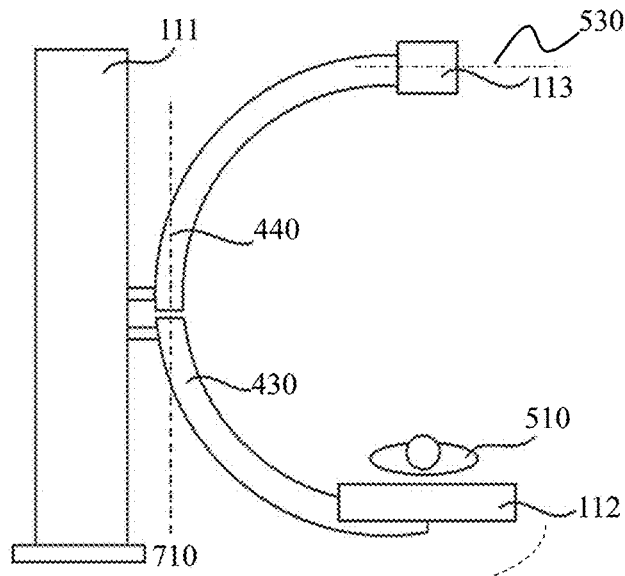
FIGS. 7A to 7D are schematic diagrams illustrating an exemplary X-ray imaging device according to some embodiments of the present disclosure.
Figure 7B:
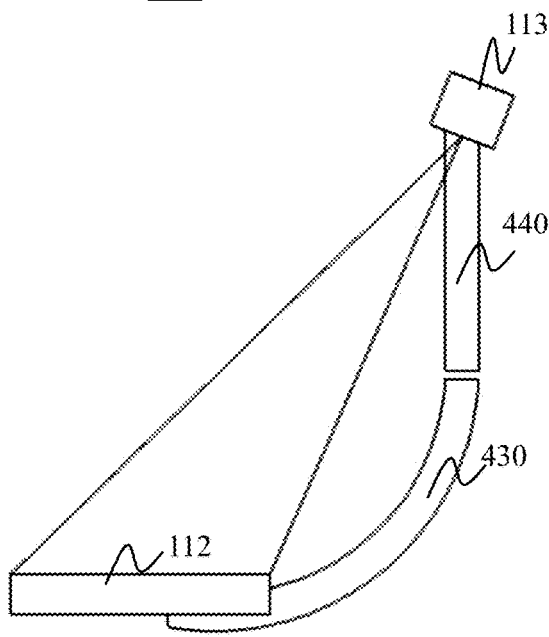
Figure 7C:
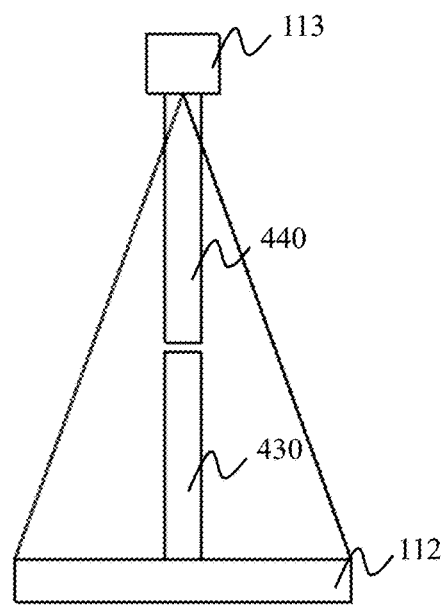
Figure 7D:
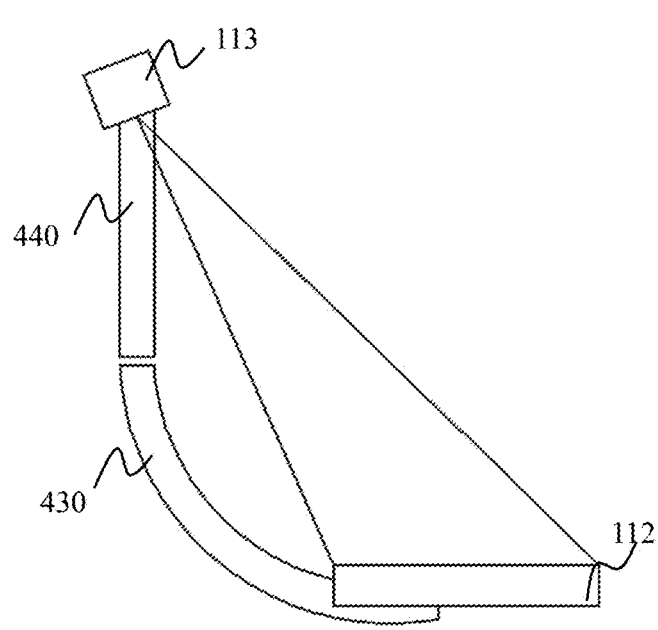

FIGS. 7A to 7D are schematic diagrams illustrating an exemplary X-ray imaging device 700 according to some embodiments of the present disclosure. The X-ray imaging device 700 may be an exemplary embodiment of the X-ray imaging device 400 as described in connection with FIG. 4. The X-ray imaging device 700 may include the gantry 111, the X-ray source 113, the detector 112, the first arm 430, and the second arm 440. FIG. 7A illustrates a side view of the X-ray imaging device 700. FIGS. 7B to 7D illustrate exemplary movements of the detector 112 and the X-ray source 113 of the X-ray imaging device 700.

The X-ray imaging device 700 may be similar to the X-ray imaging device 500 as described in FIGS. 5A to 5J, except for certain components or features. Similar to the X-ray imaging device 500, the X-ray source 113 of the X-ray imaging device 700 may rotate with respect to the second arm 440 around the axis 530. Different from the X-ray imaging device 500, the movement of the detector 112 may be driven by a movement of the first arm 430. As shown in FIGS. 7A to 7D, the first arm 430 may rotate around an axis 710. The rotation of the first arm 430 may drive a translation of the detector 112. The axis 710 may be perpendicular (or substantially perpendicular) to the detector 112 and/or a table (not shown in figures) on which the subject 510 lies.

In some embodiments, the X-ray imaging device 700 may include a first motion control device (not shown in FIGS. 7A to 7C) (e.g., the first motion control device 410 as described in FIG. 4) that can drive the first arm 430 to rotate with respect to the gantry 111, so as to drive a translation of the detector 112. Additionally or alternatively, the X-ray imaging device 700 may include a third motion control device (not shown in FIGS. 7A to 7C) (e.g., the third motion control device 450 as described in FIG. 4) that can drive a rotation of the first arm 430 respective to the second arm 440, so as to drive a translation of the detector 112. In some embodiments, the first motion control device and/or the third motion control device may include any rotation mechanism as described elsewhere in this disclosure (e.g., FIGS. 6A to 6I and the relevant descriptions).

In some embodiments, a translation of the detector 112 drove by the rotation of the first arm 430 may be along an arc path (e.g., an arc patch as shown by a dotted curve in FIG. 7A). The detector 112 may receive limited radiation rays passing through the subject 510 if the detector 112 moves for a long distance (e.g., a distance longer than a threshold distance) along the arc path, which may affect imaging quality. The moving distance of the detector 112 may need to be smaller than the threshold distance to avoid this problem. In some embodiments, the X-ray imaging device 700 may be applied to scan of a subject with a limited length (e.g., a length shorter than a threshold length).

FIGS. 8A to 8D are schematic diagrams illustrating an exemplary X-ray imaging device 800 according to some embodiments of the present disclosure. The X-ray imaging device 800 may be an exemplary embodiment of the X-ray imaging device 400 as described in connection with FIG. 4. The X-ray imaging device 800 may include the gantry 111, the X-ray source 113, the detector 112, the first arm 430, the second arm 440, and a second motion control device 810. FIG. 8A illustrates a side view of the X-ray imaging device 800. FIGS. 8B to 8D illustrate exemplary movements of the detector 112 and the X-ray source 113 of the X-ray imaging device 800.

The X-ray imaging device 800 may be similar to the X-ray imaging device 500 as described in connection with FIG. 5, except for certain components or features. Similar to the X-ray imaging device 500, the X-ray source 113 of the X-ray imaging device 800 may rotate with respect to the second arm 440 around the axis 530. Different from the X-ray imaging device 500, the movement of the detector 112 may be driven by the second motion control device 810. The second motion control device 810 may be an exemplary embodiment of the second motion control device 420 as described in FIG. 4. The second motion control device 810 may be mounted between the first arm 430 and the detector 112 configured to drive a translation of the detector 112.

In some embodiments, the second motion control device 810 may have similar components as the first motion control device 520 as shown in FIG. 5B. For example, the second motion control device 810 may include a second sliding rail, a second base, and a second driving device (not shown in FIGS. 8A to 8D). The second sliding rail may be mounted on the first arm 430 and configured to guide the translation of the detector 112. The second base may match with the second sliding rail, and may be mechanically connected to the detector 112 and the first arm 430. The second driving device may be configured to drive the second base to slide along the second sliding rail, so as to drive the movement of the detector 112.

It should be noted that the exemplary embodiments illustrated in FIGS. 4 to 8D and above description are merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

In some embodiments, an X-ray imaging device (e.g., any one of the X-ray imaging devices 400, 500, 600, 700, and 800) may further include one or more additional components. For example, the X-ray imaging device 500 may further include a control device. As another example, the X-ray imaging device 500 may include an additional base mechanically connected to the sliding rail 560 and the second arm 440, wherein the additional base may slide along the slide rail 560 to drive a translation of the second arm 440 and the X-ray source 113. Additionally or alternatively, one or more of the components described above may be omitted or replaced by one or more other components that have the same or similar functions. For example, one or more of the first, second, third, fourth, fifth motion control devices of the X-ray imaging device 400 may be omitted. In addition, any component mentioned above may be implemented in two or more separate units or and any two more components may be integrated into a single component.

Figure 9:
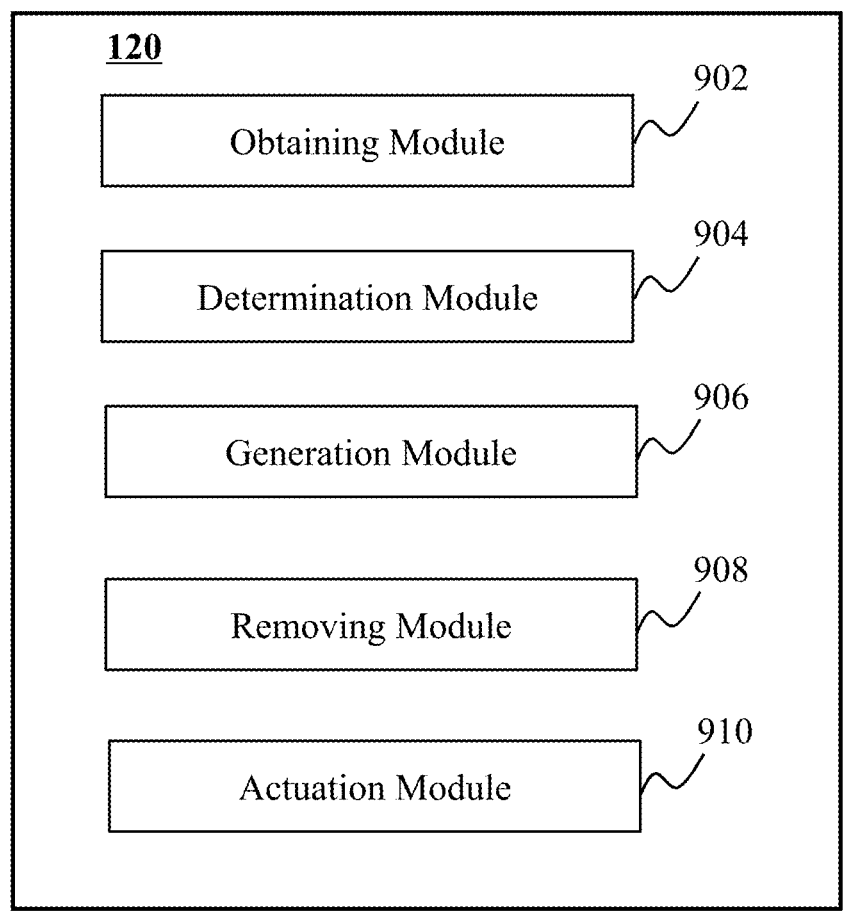
FIG. 9 is a schematic diagram illustrating an exemplary processing device according to some embodiments of the present disclosure.

FIG. 9 is a schematic diagram illustrating an exemplary processing device 140 according to some embodiments of the present disclosure. The processing device 140 may include an obtaining module 902, a determination module 904, a generation module 906, a removing module 908, and an actuation module 910. In some embodiments, at least a portion of the processing device 140 may be implemented on the computing device 400 as illustrated in FIG. 2 or the mobile device 300 as illustrated in FIG. 3.

The obtaining module 902 may be configured to obtain information related to the imaging system 100, such as one or more images of a subject. For example, the obtaining module 902 may obtain a first image (or a reference image) of a first portion of the subject. As another example, the obtaining module 902 may obtain a second image (or a target image) of a second portion of the subject. More descriptions regarding the obtaining of the image(s) may be found elsewhere in the present disclosure. See, e.g., operations 1002, 1502, 1506, and the relevant description thereof.

The determination module 904 may be configured to determine information relating to the imaging system 100. In some embodiments, the determination module 904 may be configured to determine at least one pair of feature points. Each of the pair of the feature points may include a reference feature point in the reference image and a target feature point in the target feature image. Optionally, the determination module 904 may be further configured to determine an updated pair of feature points for each of the at least one pair of feature points. For example, the determination module 904 may determine an updated pair of feature points by performing process 1100 as described in connection with FIG. 11. In some embodiments, the determination module 904 may be configured to determine feature value(s) of one or more features of a ruler, for example, by performing process 1400 as described in connection with FIG. 14.

The generation module 906 may be configured to generate a stitched image by combing a plurality of images. For example, the generation module 906 may generate a stitched image of the reference image and the target image by combining the target image and the reference image. More descriptions regarding the generation of the stitched image may be found elsewhere in the present disclosure. See, e.g., operations 1008 and 1010 and relevant descriptions thereof. As another example, the generation module 906 may perform one or more operations of process 1500 as described in connection with FIG. 15 to generate the stitched image by combining the first image and the second image of the subject.

The removing module 908 may be configured to remove a ruler from an image. For example, the removing module 908 may remove a ruler from a preliminary reference image to generate the reference image, and remove the ruler from the preliminary target image to generate the target image. In some embodiments, the removing module 908 may perform one or more operations of process 1200 as described in connection with FIG. 12 on an image (e.g., the preliminary reference image, the preliminary target image) to remove a ruler from the image.

The actuation module 910 may be configured to actuate a component of the imaging system 100 to perform a certain action. For example, the actuation module 910 may be configured to direct a control device to control movement of an X-ray device and/or a detector of an X-ray imaging device. For example, the actuation module 910 may direct the control device to control the X-ray device to move from a first position to a third position. As another example, the actuation module 910 may direct the control device to control the detector to move from a second position to a fourth position. More descriptions regarding the control device and/or the movement of the X-ray source and the detector may be found elsewhere in the present disclosure. See, e.g., FIGS. 4 to 8D and process 1500, and the relevant description thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the processing device 140 may include one or more additional components (e.g., a storage module for data storing) and/or one or more components described above may be omitted. For example, the removing module 908 and/or the actuation module 910 may be omitted. Additionally or alternatively, a module of the processing device 140 may be divided into two or more separate units or a plurality of modules of the processing device 140 may be integrated into a single module.

Figure 10:
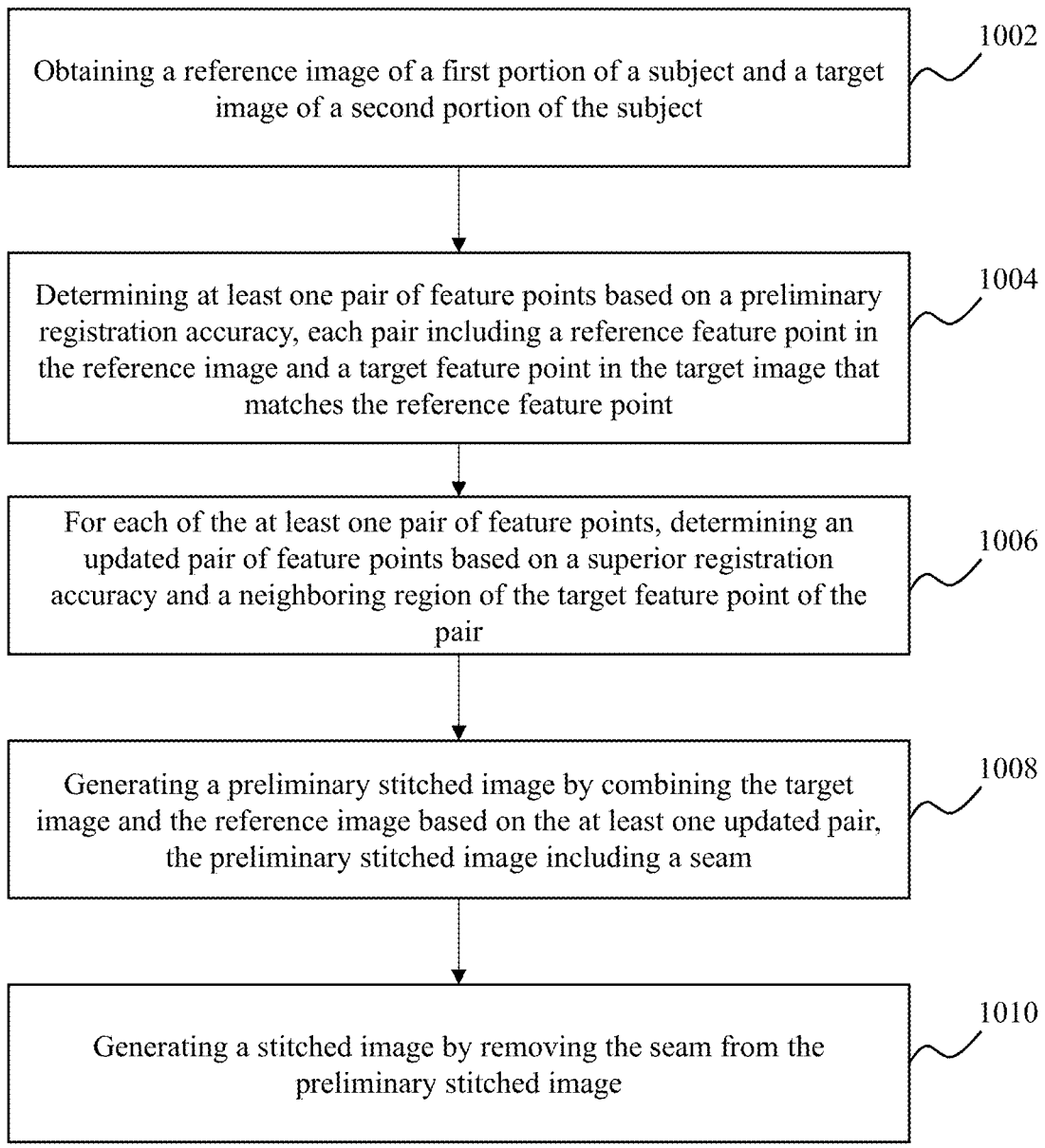
FIG. 10 is a flowchart illustrating an exemplary process for image stitching according to some embodiments of the present disclosure.

FIG. 10 is a flowchart illustrating an exemplary process for image stitching according to some embodiments of the present disclosure. In some embodiments, one or more operations of process 1000 illustrated in FIG. 10 may be implemented in the imaging system 100 illustrated in FIG. 1. For example, the process 1000 may be stored in a storage device (e.g., the storage device 150 and/or the storage 220) of the imaging system 100 in the form of instructions, and invoked and/or executed by the processing device 140 (e.g., the processor 210 of the computing device 400 as illustrated in FIG. 2, the CPU 340 of the mobile device 300 as illustrated in FIG. 3, or one or more modules of the processing device 140 illustrated in FIG. 9).

In 1002, the processing device 140 (e.g., the obtaining module 902) may obtain a reference image of a first portion of a subject and a target image of a second portion of the subject.

The subject may refer to any biological or non-biological subject, such as a patient (or a portion of the patient), a man-made object (e.g., a phantom). The first portion may include any portion of the subject. The second portion may include a portion of the subject that is different from the first portion and at least partially overlap with the first portion. In such cases, the reference image may include a first region overlapping with the target image, and the target image may include a second region overlapping with the reference image, wherein the first region and the second region both correspond to the overlapping portion between the first portion and the second portion of the subject. For example, FIG. 17 illustrates an exemplary target image 1701 and an exemplary reference image 1702 according to some embodiments of the present disclosure. The target image 1701 includes the hips and a first portion of the lower limbs of a human, and the reference image 1702 includes a second portion of the lower limbs of the human. The first portion of the lower limbs in the target image 1701 and the second portion of the lower limbs in the reference image 1702 have an overlapping portion.

In some embodiments, the reference image and/or the target image may be acquired using an imaging device (e.g., the imaging device 110). The processing device 140 may obtain the reference image and/or the target image from the imaging device. Alternatively, the reference image and/or the target image may be previously acquired using the imaging device and stored in a storage device (e.g., the storage device 150, the storage 220, and/or an external source). The processing device 140 may obtain the reference image and/or the target image from the storage device directly or via the network 120. In some embodiments, the reference image and the target image may be of a same type, such as an X-ray image, a CT image, a PET image, a DR image, a SPECT image, an MRI image, or the like.

In some embodiments, the processing device 140 may generate the reference image and the target image based on a first image of the first portion of the subject and a second image of the second portion of the subject, respectively. The first and second image may be acquired by an imaging device. For example, the first and second images may be acquired using an X-ray imaging device by performing operations 1502 to 1506 as described in connection with FIG. 15. In some embodiments, the processing device 140 may designate the first image as the reference image, and designate the second image as the target image. Alternatively, the processing device 140 may process the first image and the second image. A processing of an image may include an image denoising, an image filtering, an image correction, or the like, or any combination thereof. For example, each of the first image and the second image may include at least a portion of a ruler. The first image including at least a portion of the ruler may be referred to as a preliminary reference image, and the second image including at least a portion of the ruler may be referred to as a preliminary target image. The processing device 140 may remove the ruler from the preliminary reference image to generate the reference image, and remove the ruler from the preliminary target image to generate the target image. In some embodiments, the processing device 140 may perform one or more operations of process 1200 as described in connection with FIG. 12 on an image (e.g., the preliminary reference image, the preliminary target image) to remove a ruler from the image.

In 1004, the processing device 140 (e.g., the determination module 904) may determine at least one pair of feature points based on a preliminary registration accuracy. Each pair of the feature points may include a reference feature point in the reference image and a target feature point in the target image that matches the reference feature point.

A reference feature point may include any point in the first region of the reference image (i.e., an overlapping region with the target image). A target feature point may include any point in the second region of the target image (i.e., an overlapping region with the reference image). In some embodiments, a reference feature point and a target feature point that correspond (or substantially correspond) to a same physical point of the subject may match each other and form a pair of feature points. For example, as shown in FIG. 17, a plurality of pairs of feature points may be determined for the target image 1701 and the reference image 1702. Each pair may include a reference feature point in the reference image 1702 and a target feature point in the target image 1701 matching the reference feature point. The pairs includes a first pair including a target feature point 1701-1 and a target feature point 1702-1, a second pair including a target feature point 1701-2 and a target feature point 1702-2, . . . , and an nth pair including a target feature point 1701-$n$ and a target feature point 1702-$n$.

In some embodiments, a preliminary registration accuracy may refer to a pixel-level accuracy. In this situation, each determined feature point may be a pixel point. In some embodiments, the processing device 140 may determine a pair of feature points based on a feature point detection algorithm. Exemplary feature point detection algorithms may include a corner detection algorithm, a Laplacian of the Gaussian (LoG) algorithm, a Speeded Up Robust Features (SURF), a Features from accelerated segment test (FAST), a Binary Robust Invariant Scalable Keypoints (BRISK) algorithm, a Fast Retina KeyPoint (FREAK) algorithm, a Scale Invariant Feature Transform (SIFT) algorithm, a Harris algorithm, a small univalue segment assimilating nucleus (SUSAN) algorithm, a good Feature To Track (GFTT) algorithm, or the like, or any combination thereof.

In 1006, for each of the at least one pair, the processing device 140 (e.g., the determination module 904) may determine an updated pair of feature points based on a superior registration accuracy and a neighboring region of the target feature point of the pair, wherein the updated pair may include the reference feature point of the pair in the reference image and an updated target feature point in the target image.

In some embodiments, the superior registration accuracy may be higher than the preliminary registration accuracy. For example, the superior registration accuracy may refer to a subpixel-level accuracy. Optionally, the superior registration accuracy may specify a desired pixel size of an updated target feature point, such as ½ pixels, ¼ pixels, or the like. In this situation, each updated target feature point may need to be a subpixel whose pixel size is equal to or smaller than the desired pixel size. For example, FIG. 18 illustrates a pair of feature points and an updated pair of feature points in the target image 1701 and the reference image 1702 according to some embodiments of the present disclosure. As shown in FIG. 18, the target image 1701 and the reference image 1702 may be represented by a region 1801 and a region 1802, respectively, in a coordinate system. A pair of feature points may include a reference feature point denoted as v0(x2, y2) and a target feature point denoted as u0(x1, y1). The processing device 140 may determine an updated target feature point denoted as u1 (x1+r, y1+t) in the target image 1701, which may form the updated pair with the reference feature point v0 (x2, y2). The updated target feature point u1(x1+r, y1+t) may be a subpixel.

A neighboring region of a target feature point may refer to a region enclosing the target feature point. The neighboring region may have any shape and size. For example, the region may have the shape of a square, a rectangle, a triangle, a polygon, a circle, an ellipse, an irregular shape, or the like. Taking a neighboring region having the shape of a circle as an instance, the size of the neighboring region may be a circle with a default radius, such as 1 pixel, 2 pixels, 3 pixels, or the like. In some embodiments, the superior registration accuracy and/or the configuration of a neighboring region may be a default setting of the imaging system 100 or be set manually by a user of the imaging system 100. Alternatively, the superior registration accuracy and/or the configuration of a neighboring region may be adjustable and determined based on actual needs. In some embodiments, a neighboring region of a target feature point may be determined based on the superior registration accuracy. For example, the superior registration accuracy may specify that the pixel size of an updated target feature point needs to be equal to or smaller than ½ pixels. The neighboring region of the target feature point may be a circle whose center is the target feature point and having a predetermined radius. The predetermined radius may have any value greater than ½ pixels, such as 1 pixel, 1.5 pixels, 2 pixels, or the like.

In some embodiments, for a pair of feature points, the processing device 140 may determine a plurality of interpolation points within the neighboring region of the target feature point of the pair. The processing device 140 may select an interpolation point according to a selection rule (e.g., a rule specifies that an interpolation point having the highest similarity degree to the reference feature point of the pair is selected) from the plurality of points. The selected interpolation point may be directly designated as an updated target feature point of an updated pair of feature points corresponding to the pair. Alternatively, the processing device 140 may further determine whether the selected interpolation point satisfies a specific condition. In response to a determination that the selected interpolation point satisfies the specific condition, the selected interpolation point may be designated as the updated target feature point. In response to a determination that the selected interpolation point does not satisfy the specific condition, the processing device 140 may perform one or more additional operations to determine a new interpolation point. In some embodiments, the processing device 140 may perform one or more iterations as described in connection with FIG. 11 to determine an updated pair of feature points for a pair of feature points.

In 1008, the processing device 140 (e.g., the generation module 906) may generate a preliminary stitched image by combining the target image and the reference image based on the at least one updated pair of feature points.

In some embodiments, before stitching the target image and the reference image, the processing device 140 may pre-process the reference image and the target image. The pre-processing may include image transformation, image denoising, image filtering, image enhancement, or the like, or any combination thereof. The image transformation may include a translation, a rotation, a scaling, or the like, or any combination thereof.

In some embodiments, the processing device 140 may generate the preliminary stitched image using an image stitching algorithm, such as an optimal seam-line algorithm, a pyramid-based algorithm, a gradient-based algorithm, a feathering-based algorithm, or the like, or any combination thereof. In some embodiments, the reference image may be represented by a first matrix including a plurality of first elements, each of which corresponds to a pixel of the reference image. The target image may be represented by a second matrix including a plurality of second elements, each of which corresponds to a pixel or an updated sub-pixel (e.g., an updated target feature point) of the target image. The processing device 140 may transform the second matrix to generate a transformed second matrix that matches the first matrix based on the at least one updated pair of feature points. A transformation of the second matrix may include a matrix translation, a matrix rotation, a matrix scaling, or the like, or any combination thereof. For example, it is assumed that a reference feature point and a corresponding updated target feature point are represented by an element X in the first matrix and an element Y in the second matrix, respectively. During the transformation of the second matrix, the element Y may be translated to an updated position in the transformed second matrix, wherein the updated position may be the same as or similar to the position of the element X in the first matrix. As another example, the processing device 140 may determine a positional relationship between the updated position and the original position of the element Y (e.g., a distance between the updated position and the original position, a direction from the original position to the updated position). For another element which does not correspond to an updated target feature point in the second matrix, the processing device 140 may transform the element according to the positional relationship. In some embodiments, the first matrix and/or the second matrix may be two-dimensional (2D). As used herein, the position of an element in a two-dimensional matrix may be described using the row number and the column number of the element. In some embodiments, at least one updated target feature point, which is a sub-pixel, may be determined in operation 1006. The processing device 140 may interpolate the reference image and the target image. Both of the interpolated reference image and the interpolated target image may have a sub-pixel resolution corresponding to the at least one updated target feature point. The processing device 140 may further generate the preliminary stitched image by combining the interpolated reference image and the interpolated target image based on the at least one updated pair of feature points.

In some embodiments, the preliminary stitched image may include a seam located at a joining part of the reference image (or the interpolated reference image) and the target image (or the interpolated target image). For example, FIG. 19A illustrates a preliminary stitched image 1901 of the target image 1701 and the reference image 1702 according to some embodiments of the present disclosure. The preliminary stitched image 1901 includes a seam (indicated by a box 1903) at a joining part of the target image 1701 and the reference image 1702.

In 1010, the processing device 140 (e.g., the generation module 906) may generate a stitched image by processing the preliminary stitched image.

For example, the preliminary stitched image may include a seam as described above. The processing device 140 may generate the stitched image by removing the seam from the preliminary stitched image, so as to improve the image quality. In some embodiments, the processing device 140 may utilize an image fusion algorithm to remove the seam. Exemplary image fusion algorithms may include a weighted average algorithm, a pyramid-based algorithm, a multi-resolution-based image fusion algorithm, or the like, or any combination thereof. For example, FIG. 19B illustrates an exemplary stitched image 1902 generated by removing the seam 1903 from the preliminary stitched image 1901 according to some embodiments of the present disclosure.

According to some embodiments of the present disclosure, one or more pair of feature points may be determined in the target image and the reference image. For a pair of feature points, an updated target feature point may be determined in a neighboring region of the target feature point in the pair based on the superior registration accuracy. The updated featured point may be a sub-pixel, which may improve stitching accuracy. In addition, in some embodiments, interpolation points in a neighboring region of the target feature point may be determined, and the updated feature point may be determined from the interpolation points. Compared with determining interpolation points in the whole target image, the methods disclosed in the present disclosure are more efficient and time-saving.

It should be noted that the above description regarding the process 1000 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. The operations of the illustrated process 1000 are intended to be illustrative. In some embodiments, the process 1000 may be accomplished with one or more additional operations not described, and/or without one or more of the operations discussed. For example, operation 1010 may be omitted. In 1008, the processing device 140 may directly generate the stitched image by combining the target image and the reference image. As another example, the processing device 140 may transmit the stitched image to a terminal (e.g., a terminal 130 of a doctor) for presentation. Additionally, the order in which the operations of the process 1000 as illustrated in FIG. 10 and described above is not intended to be limiting.

Figure 11:
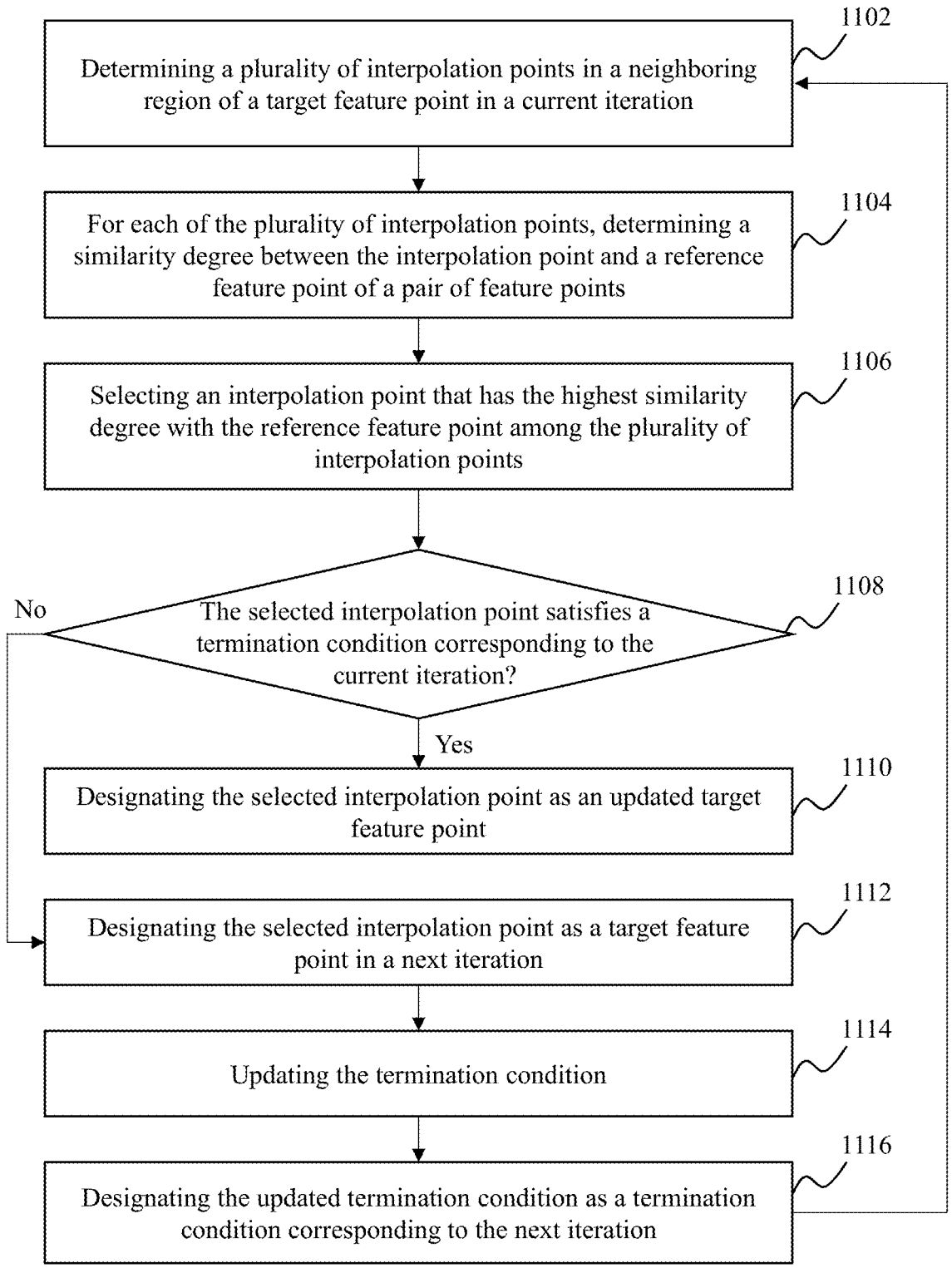
FIG. 11 is a flowchart illustrating an exemplary process for determining an updated target feature point of an updated pair of feature points according to some embodiments of the present disclosure.

FIG. 11 is a flowchart illustrating an exemplary process for determining an updated target feature point of an updated pair of feature points according to some embodiments of the present disclosure. In some embodiments, one or more operations of the process 1100 illustrated in FIG. 11 may be implemented in the imaging system 100 illustrated in FIG. 1. For example, the process 1100 may be stored in a storage device (e.g., the storage device 150, and/or the storage 220) of the imaging system 100 in the form of instructions, and invoked and/or executed by the processing device 140 (e.g., the processor 210 of the computing device 200 as illustrated in FIG. 2, the CPU 340 of the mobile device 300 as illustrated in FIG. 3, or one or more modules of the processing device 140 illustrated in FIG. 9).

In some embodiments, one or more operations of the process 1100 may be performed to achieve at least part of operation 1006 as described in connection with FIG. 10. As described in connection with 1006, for a pair of feature points, the processing device 140 may determine an updated pair of feature points including and updated target feature point in the target image and the reference feature point of the pair. The updated target feature point may be determined based on a neighboring region of the target feature point of the pair and a superior registration accuracy. In some embodiments, the processing device 140 may perform one or more iterations to determine the updated target feature point. During the iteration(s), the target feature point, the neighboring region of the target feature point, and optionally the superior registration accuracy may be updated. For illustration purposes, a current iteration of the iteration(s) is described hereinafter. The current iteration may include one or more of operations 1102 to 1116 as shown in FIG. 11.

In 1102, the processing device 140 (e.g., the determination module 904) may determine a plurality of interpolation points in a neighboring region of a target feature point in the current iteration.

For the convenience of description, the neighboring region of the target feature point in the current iteration may be referred to as a current neighboring region. The current neighboring region may be similar to the neighboring region of the original target feature point as described in connection with operation 1006. In some embodiments, the current neighboring region may be predetermined by the imaging system 100 or be set manually by a user of the imaging system 100. For example, the current neighboring region may be a circle whose center is the target feature point in the current iteration and having a predetermined radius. In some embodiments, the current neighboring region may be determined based on the superior registration accuracy corresponding to the current iteration. For example, the superior registration accuracy corresponding to the current iteration may specify a desired pixel size of the updated target feature point in the current iteration, such as ½ pixels. The current neighboring region may need to cover a region including a plurality of points, wherein a distance between each of the points and the target feature point in the current iteration may need to be greater than ½ pixels.

The interpolation points may be determined by performing an image interpolation in the current neighboring region. In some embodiments, the processing device 140 may determine the interpolation points based on an interpolation algorithm. Exemplary interpolation algorithms may include a nearest neighbor interpolation algorithm, a bilinear interpolation algorithm, a bicubic interpolation algorithm, an edge-directed interpolation algorithm, a spline interpolation algorithm, a sinc interpolation algorithm, a Lanczos interpolation algorithm, or the like, or a combination thereof.

In 1104, the processing device 140 (e.g., the determination module 904) may determine a similarity degree between each interpolation point and the reference feature point of the pair.

In some embodiments, a similarity degree between an interpolation point and the reference feature point may be measured by a similarity degree between a feature vector of the interpolation point and a feature vector of the reference feature point, a similarity degree between grey information of the interpolation point and the reference feature point, a similarity degree based on mutual Information, or the like, or any combination thereof. Merely by way of example, the similarity degree may be measured by a distance (e.g., a Euclidean distance, a Markov distance, a cosine distance) between the feature vectors of the interpolation point and the reference feature point. As another example, the similarity degree may be determined according to a probability measuring algorithm.

In 1106, the processing device 140 (e.g., the determination module 904) may select an interpolation point that has the highest similarity degree with the reference feature point among the plurality of interpolation points. For example, the processing device 140 may rank the interpolation points according to their respective similarity degree with the reference feature point in a descending order. The processing device 140 may further select the interpolation point in the top of the ranking result.

In 1108, the processing device 140 (e.g., the determination module 904) may determine whether the selected interpolation point satisfies a termination condition corresponding to the current iteration.

In some embodiments, the termination condition corresponding to the current iteration may include that the selected interpolation point achieves the superior registration accuracy corresponding to the current iteration. Merely by way of example, the superior registration accuracy corresponding to the current iteration may specify that a desired pixel size (e.g., ¼ pixels) of the updated target feature point in the current iteration. The processing device 140 may determine whether a pixel size of the selected interpolation point is less than the desired pixel size in the current iteration. If the pixel size of the selected interpolation point is less than the desired pixel size in the current iteration, the processing device 140 may determine that the selected interpolation point satisfies the termination condition in the current iteration. If the pixel size of the selected interpolation point is greater than the desired pixel size in the current iteration, the processing device 140 may determine that the selected interpolation point does not satisfy the termination condition in the current iteration.

Additionally or alternatively, the termination condition in the current iteration may include that a similarity degree between the selected interpolation point and the reference feature point is within a similarity range corresponding to the current iteration. The similarity range corresponding to the current iteration may specify a minimum similarity degree and/or a maximum similarity degree between the selected interpolation point and the reference feature point. For example, if the pixel size of the selected interpolation point is less than the desired pixel size in the current iteration and the similarity degree of the selected interpolation point is within the similarity range of the current iteration, the processing device 140 may determine that the selected interpolation point satisfies the termination condition in the current iteration. If the pixel size of the selected interpolation point is greater than the desired pixel size in the current iteration or the similarity degree of the selected interpolation point is out of the similarity range of the current iteration, the processing device 140 may determine that the selected interpolation point does not satisfy the termination condition in the current iteration. In some embodiments, the similarity range corresponding to the current iteration may be a default setting of the imaging system 100 or be set manually by a user of the imaging system 100. Alternatively, the similarity range corresponding to the current iteration may be adjustable and determined based on actual needs.

In response to a determination that the selected interpolation point satisfies the termination condition in the current iteration, the process 1100 may proceed to operation 1110. In 1110, the processing device 140 (e.g., the determination module 904) may designate the selected interpolation point as the updated target feature point. The updated target feature point and the reference feature point may form the updated pair of feature points. Optionally, the processing device 140 may store the updated target feature point and/or the updated pair into a storage device (e.g., the storage device 150) via the network 120.

In response to a determination that the selected interpolation point does not satisfy the termination condition, the process 1100 may proceed to operations 1112 to 1116. In 1112, the processing device 140 (e.g., the determination module 904) may designate the selected interpolation point as a target feature point in a next iteration.

In 1114, the processing device 140 (e.g., the determination module 904) may update the termination condition. In some embodiments, the updated termination condition may include an updated superior registration accuracy higher than the superior registration accuracy in the current iteration. Merely by way of example, the superior registration accuracy in the current iteration may specify that the desired size of the updated target feature point in the current iteration is ⅓ pixels, and the updated superior registration accuracy may specify a desired size smaller than ⅓ pixels. Additionally or alternatively, the updated termination condition may include an updated similarity range higher than the similarity range in the current iteration. Merely by way of example, the updated similarity range may specify an updated minimum similarity degree and/or an updated maximum similarity degree between the selected interpolation point and the reference feature point. The updated minimum similarity degree may be higher than the minimum similarity degree specified by the similarity range corresponding to the current iteration. Additionally or alternatively, the updated maximum similarity degree may be higher than the maximum similarity degree specified by the similarity degree corresponding to the current iteration.

In 1116, the processing device 140 (e.g., the determination module 904) may designate the updated termination condition as a termination condition corresponding to the next iteration. In this way, an updated target feature point having a smaller pixel size (e.g., a smaller subpixel) and/or a higher similarity degree with the reference feature point may be determined in the next iteration, thereby improving image stitching accuracy. After 1114, the processing device 140 may proceed to operation 1102 again to perform the next iteration until the termination condition is satisfied in a certain iteration.

It should be noted that the above description regarding the process 1100 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. The operations of the illustrated process 1100 are intended to be illustrative. In some embodiments, the process 1100 may be accomplished with one or more additional operations not described, and/or without one or more of the operations discussed. For example, operations 1114 and 1116 may be omitted, and a same termination condition may be applied in each iteration. Additionally, the order in which the operations of the process 1100 as illustrated in FIG. 11 and described above is not intended to be limiting.

Figure 12:
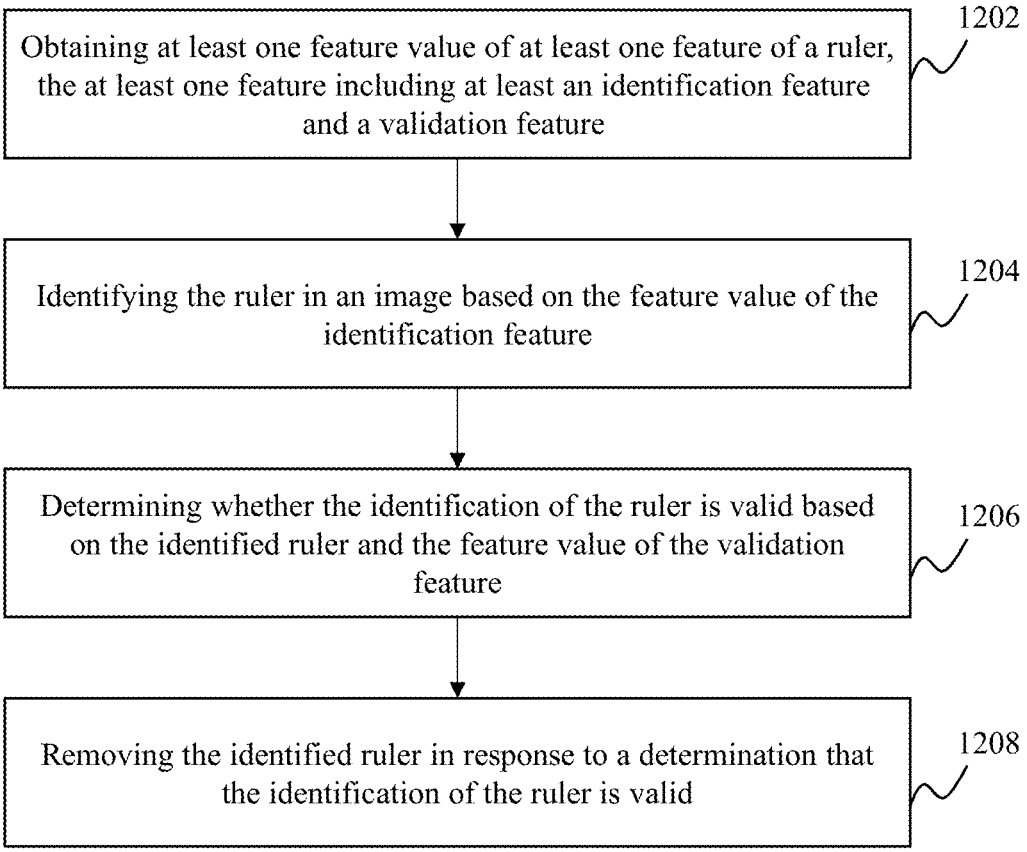
FIG. 12 is a flowchart illustrating an exemplary process for removing a ruler form an image according to some embodiments of the present disclosure.

FIG. 12 is a flowchart illustrating an exemplary process for removing a ruler form an image according to some embodiments of the present disclosure. In some embodiments, one or more operations of process 1200 illustrated in FIG. 12 may be implemented in the imaging system 100 illustrated in FIG. 1. For example, the process 1200 illustrated in FIG. 12 may be stored in a storage device (e.g., the storage device 150, and/or the storage 220) of the imaging system 100 in the form of instructions, and invoked and/or executed by the processing device 140 (e.g., the processor 210 of the computing device 200 as illustrated in FIG. 2, the CPU 340 of the mobile device 300 as illustrated in FIG. 3, or one or more modules of the processing device 140 illustrated in FIG. 9). In some embodiments, one or more operations of the process 1200 may be performed to achieve at least part of operation 1002 as described in connection with FIG. 10.

In 1202, the processing device 140 (e.g., the removing module 908) may obtain at least one feature value of at least one feature of a ruler.

Figure 20A:
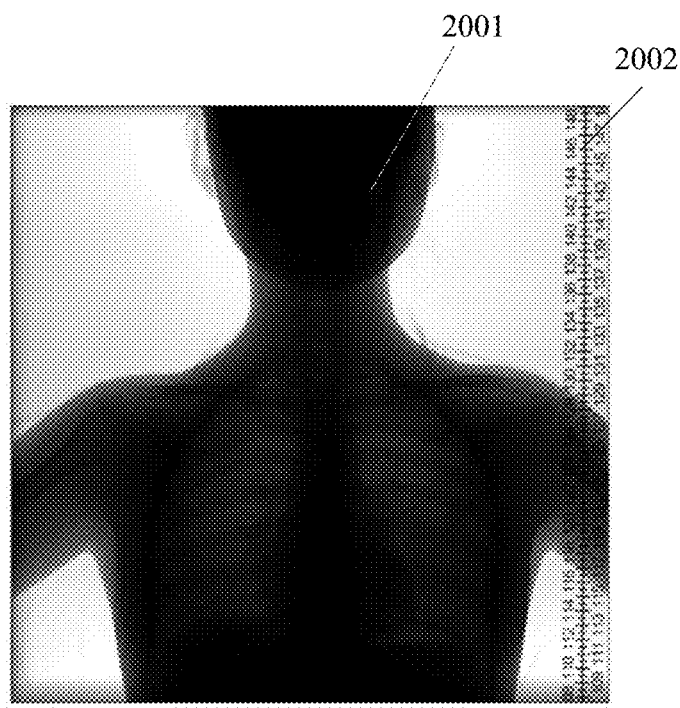
FIG. 20A illustrates an exemplary image including a subject and portion of a ruler according to some embodiments of the present disclosure.

In some embodiments, the image may relate to a subject and be captured by an imaging device (e.g., the imaging device 110, the X-ray imaging device 400, etc.) during a scan of the subject. During the scan, the ruler may be placed beside the subject, and the image may include at least a portion of the subject and at least a portion of the ruler. The ruler in the image may need to be removed before the image is subject to further processing (e.g., image stitching). For illustration purposes, FIG. 20A illustrates an image 2000 including a subject 2001 and portion of a ruler 2002 according to some embodiments of the present disclosure. The ruler 2002 may need to be removed from the image 2000. In some embodiments, the image may be a preliminary reference image or a preliminary target image as described in connection with operation 1002.

Figure 21A:
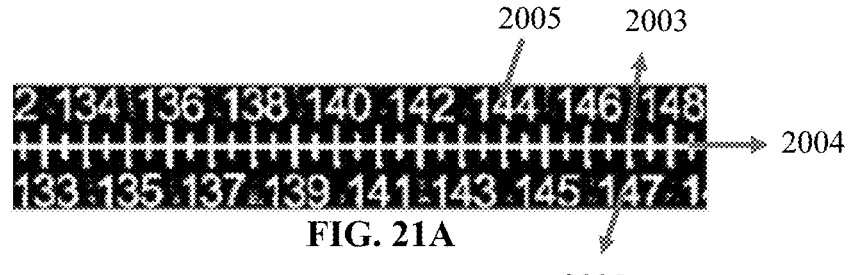
FIGS. 21A to 21C are schematic diagrams illustrating an exemplary process of validating an identification of a ruler according to some embodiments of the present disclosure.

In some embodiments, the ruler may include one or more components, such as a scale axis (e.g., a scale axis 2004 as shown in FIG. 21A), one or more scale lines (e.g., scale lines 2003 as shown in FIG. 21A), one or more numbers (e.g., numbers 2005 as shown in FIG. 21A), or the like, or any combination thereof. The scale axis may refer to a line extending on the ruler along the extension direction of the ruler. The at least one feature of the ruler may include, for example, a feature relating to a ruler width of the ruler, a feature relating to the number(s), a feature relating to the scale axis, a feature relating to the scale line(s), or the like, or any combination thereof. As used herein, a width of a component of the ruler may refer a length of the component in the image along a direction perpendicular to an extension direction of the ruler. A height of a component of the ruler may refer to a length of the component in the image along the extension direction of the ruler. Exemplary features relating to the ruler width may include a width of the ruler or a portion of the ruler (e.g., a portion including the number(s), the scale line(s), and the scale axis), or the like, or any combination thereof. Exemplary features relating to the number(s) of the rule may include a font, a size, a height, a width, a thickness, a tilt angle, or one or more other features of each number, or any combination thereof. Exemplary features relating to the scale axis may include whether the ruler has a scale axis or not, a form, a width, a shape of the scale axis, or the like, or any combination thereof. The form of the scale axis may include a straight line, a curved line, a broken line, or the like.

Exemplary features relating to the scale line(s) may include a shape, a height, a width, and a pitch angle of each scale line, the count of the scale line(s), a distance between adjacent scale lines along the extension direction of the ruler, a unit length of the scale line(s), or the like. A scale line may have a shape of, for example, a straight line, a point, a slash, a step, or the like. In some embodiments, the ruler may include a plurality of scale lines, which includes a set of scale lines appears periodically on the ruler. The unit length may refer to a distance between two adjacent sets of scale lines. In some embodiments, a ruler may include a plurality of scale lines. The scale lines may be of a same type having a same configuration (e.g., shape and size). Alternatively, the scale lines may include different types of scale lines having different configurations. The feature relating to the scale lines may include one or more features of each type of scale lines.

In some embodiments, the at least one feature may include an identification feature and a validation feature different from the identification feature. The identification feature may be used to identify the ruler in the image. The validation feature may be used to verify that the identification of the ruler is valid. In some embodiments, the identification feature may include one or more features of the at least one feature of the ruler. The validation feature may include one or more features other than the identification feature of the at least one feature of the ruler. For example, the identification feature may include the features relating to the ruler width, the scale axis, and/or the number(s) of the ruler. The validation feature may include the feature relating to the scale line(s) of the ruler.

It should be noted that the features of the rule described above are provided for illustration purposes, and not intended to limit the scope of the present disclosure. Different rulers may have different types of features. In some embodiments, different types of features (e.g., different types of identification features and/or different types of validation features) may be utilized to identify and remove rulers in different images.

In some embodiments, a feature value of a feature of the ruler may be input by a user (e.g., a doctor) and/or determined by analyzing a template image of the ruler. For example, the processing device 140 may determine a feature value based on the template image by performing one or more operations in process 1400 as described in FIG. 14. In some embodiments, a feature value of the ruler may be previously determined (e.g., according to the process 1400) and stored in a storage device (e.g., the storage device 150, the storage 220, or an external source). The processing device 140 may obtain the feature value from the storage device via the network 120.

In 1204, the processing device 140 (e.g., the removing module 908) may identify the ruler in the image based on the feature value of the identification feature.

In some embodiments, the identification feature may include a positioning feature and a matching feature. The positioning feature may be used to identify a preliminary region representing the ruler in the image. The preliminary region may be regarded as an approximate position of the ruler in the image. The matching feature may be used to identify the ruler (i.e., determine a precise location of the ruler) according to the preliminary region. For example, the precise location may be determined by matching a feature value of each point within or close to the preliminary region with the feature value of the matching feature.

In some embodiments, the positioning feature may include any feature of the at least one feature of the ruler, and the matching feature may include any feature other than the positioning feature of the at least one feature. Merely by way of example, the positioning feature may include the feature relating to the scale axis and the feature relating to the ruler width, and the matching feature may include the feature relating to the number(s). As another example, the positioning feature may include the form (or width) and the unit length of the scale line(s), and the matching feature may include another feature relating to the scale line(s) and the feature relating to the ruler width or the number(s).

In 1206, the processing device 140 (e.g., the removing module 908) may determine whether the identification of the ruler is valid based on the identified ruler and the feature value of the validation feature.

In some embodiments, the processing device 140 may determine a feature value of the validation feature of the identified ruler, and match the determined feature value with the known feature value of the validation feature obtained in 1202 to verify whether the identification of the ruler is valid. If a difference between the determined feature value and the known feature value is smaller than a threshold value, the determined feature value may be deemed as marching the known feature value and the processing device 140 may determine that the identification of the ruler is valid. In response to the determination that the identification is valid, the processing device 140 may proceed to 1208. If the difference is greater than the threshold value, the processing device 140 may determine that the identification of the ruler is invalid. Optionally, the processing device 140 may perform operations 1202 to 1206 again to re-identify the ruler in the image.

Figure 20B:
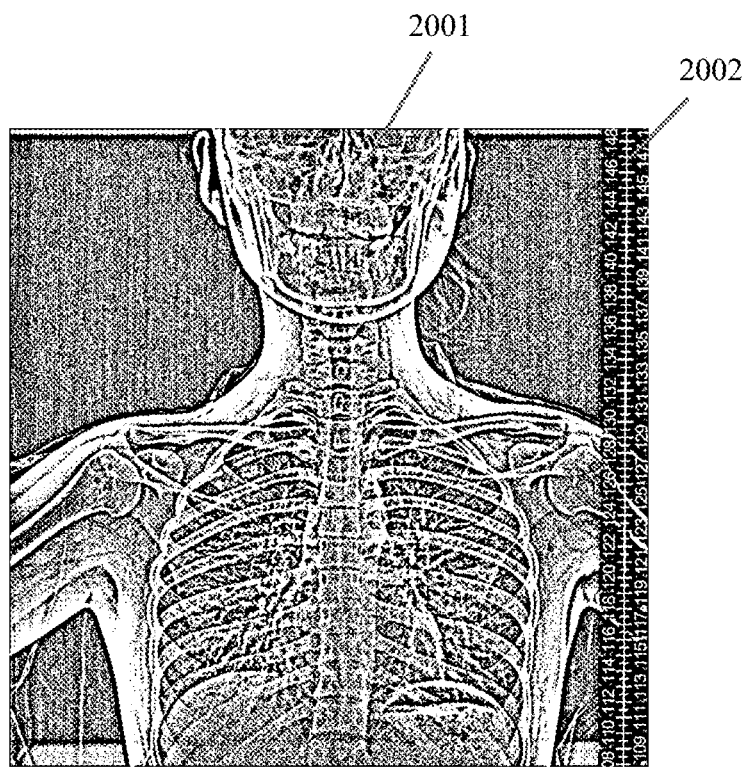
FIG. 20B illustrates an exemplary binary image of the image in FIG. 20A according to some embodiments of the present disclosure.
Figure 21B:
Figure 21C:
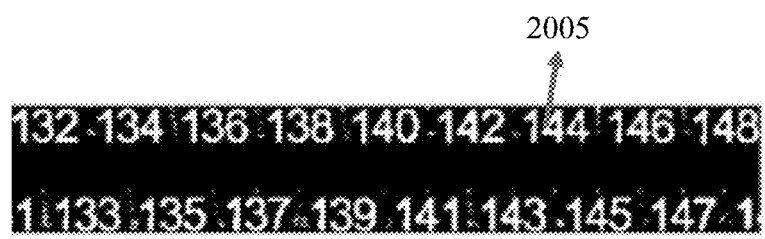

In some embodiments, the validation feature may include the feature relating to the scale line(s) and/or the feature relating to the number(s). For illustration purposes, a validation of the identification of the ruler 2002 illustrated in FIGS. 20A and 20B is described as an example. FIGS. 21A to 21C are schematic diagrams illustrating a process of validating the identification of the ruler 2002 according to some embodiments of the present disclosure. As shown in FIGS. 21A to 21C, the ruler 2002 includes a scale axis 2004, a plurality of numbers 2005, and a plurality of scale lines 2003. The scale axis 2004 extends along a direction that is parallel with the extension direction of the ruler 2002. The scale lines 2003 are arranged periodically and perpendicular to the scale axis 2004. The numbers 2005 are located on two sides of the scale axis 2004. For example, as shown in FIG. 21A, the processing device 140 may segment the identified ruler 2002 from a binary image 2010 of the image 2000. As shown in FIG. 21B, the processing device 140 may further segment the scale lines 2003 and the scale axis 2004 from the identified ruler 2002. For example, the scale lines 2003 and the scale axis 2004 may be segmented based on the position of the scale axis 2004 and a length of the scale lines 2003 along a direction perpendicular to the extension direction of the ruler 2002. As shown in FIG. 21C, a remaining portion including the numbers 2005 may be obtained after the scale lines 2003 and the scale axis 2004 are segmented.

In some embodiments, the processing device 140 may determine feature value(s) relating to the scale lines 2003 based on the image in FIG. 21B. Additionally or alternatively, the processing device 140 may determine feature value(s) relating to the numbers 2005 based on the image in FIG. 21C. The processing device 140 may verify whether the identification of the ruler 2002 is valid by matching the determined feature value(s) with known feature value(s) of the scale lines 2003 and/or the numbers 2005.

In 1208, the processing device 140 (e.g., the removing module 908) may remove the identified ruler in response to a determination that the identification of the ruler is valid. For example, the processing device 140 may remove the identified ruler by segmenting the identified ruler from the image.

Figure 13:
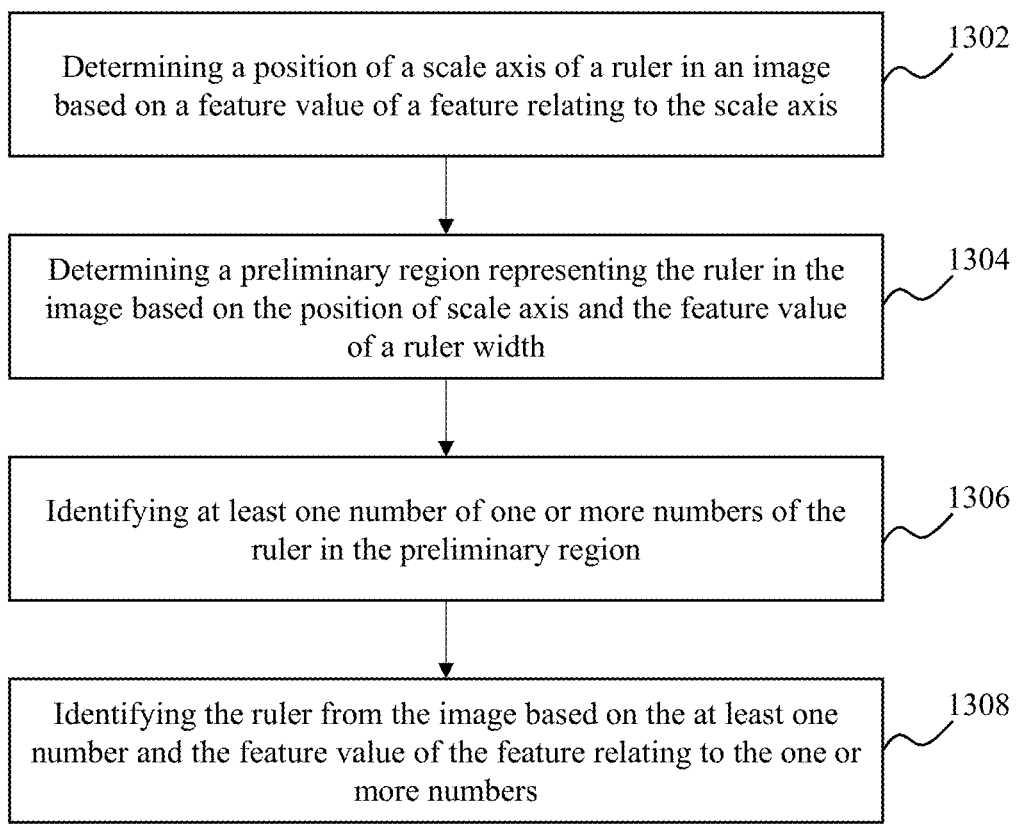
FIG. 13 is a flowchart illustrating an exemplary process for identifying a ruler from an image according to some embodiments of the present disclosure.

As described in connection with operation 1204, the ruler may be identified from the image based on the feature value of an identification feature. In some embodiments, the identification feature may include a positioning feature and a matching feature. The positioning feature may include the feature relating to the scale axis and the feature relating to the ruler width. The matching feature may include the feature relating to the number(s) of the ruler. The processing device 140 may perform an exemplary process 1300 illustrated in FIG. 13 to achieve operation 1204.

In 1302, the processing device 140 (e.g., the removing module 908) may determine a position of the scale axis of the ruler in the image based on the feature value of feature relating to the scale axis.

In some embodiments, the processing device 140 may transform the image into a binary image. In some embodiments, the binary image may be generated based on a local binarization algorithm. For example, the image may be divided into a plurality of cells. Each cell may have a corresponding pixel value threshold. In each cell, a pixel having a pixel value greater than the corresponding pixel threshold in the image may have a pixel value of 1 in the binary image, and a pixel having a pixel value smaller than the corresponding pixel threshold in the image may have a pixel value of 0 in the binary image. For illustration purposes, FIG. 20B illustrates an exemplary binary image 2010 of the image 2000 in FIG. 20A according to some embodiments of the present disclosure. The binary image 2010 may be generated by transforming the image 2000 using a localization binarization algorithm.

Then, the processing device 140 may identify one or more straight lines in the binary image using, for example, a Hough transformation algorithm. The processing device 140 may further determine the position of the scale axis based on the straight line(s). For example, if there is only one straight line, the position of the scale axis may be determined based on the straight line. As another example, if there is a plurality of straight lines, a straight line having a same or similar feature values (e.g., a tilt angle) as the scale axis may be identified, and the position of the scale axis may be determined based on the identified straight line.

In 1304, the processing device 140 (e.g., the removing module 908) may determine a preliminary region representing the ruler in the image based on the position of scale axis and the feature value of the ruler width.

For example, the processing device 140 may determine a rectangle or square region whose central point is the middle point of the identified scale axis and whose two sides are parallel with the scale axis. The height of the region may be equal to the height of the identified scale axis and the width of the region is equal to the ruler width. The processing device 140 may further designate the region as the preliminary region.

In 1306, the processing device 140 (e.g., the removing module 908) may identify at least one number of one or more numbers in the preliminary region. For example, the processing device 140 may identify one or more of numbers from 0 to 9 in the preliminary region.

In 1308, the processing device 140 (e.g., the removing module 908) may identify the ruler from the image based on the at least one number and the feature value of the feature relating to the one or more numbers.

In some embodiments, the processing device 140 may determine one or more feature values of one or more features, such as a font, a font size, a thickness, a tilt angle of an identified number. The processing device 140 may further match the determined feature value(s) of the identified number with the known feature value relating the number(s) of the ruler. If a difference between a determined feature value of the identified number and a known feature value of a certain known number is smaller than a threshold, the identified number may be deemed as matching the certain known number. The processing device 140 may further determine the position and/or the ruler width of the ruler based on the identified number that matches the certain known number. In some embodiments, the at least one identified number may include a plurality of identified numbers. The processing device 140 may identify the ruler based on all or a portion of the identified numbers.

It should be noted that the above descriptions regarding the process 1200 and the process 1300 are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 1200 and/or the process 1300 may be accomplished with one or more additional operations not described, and/or without one or more of the operations discussed may be omitted. For example, operation 1206 may be omitted, and operation 1208 may be performed to remove the identified ruler directly after operation 1204. In some embodiments, the ruler may be identified in the image based on one or more identification features other than those described in process 1300.

Figure 14:
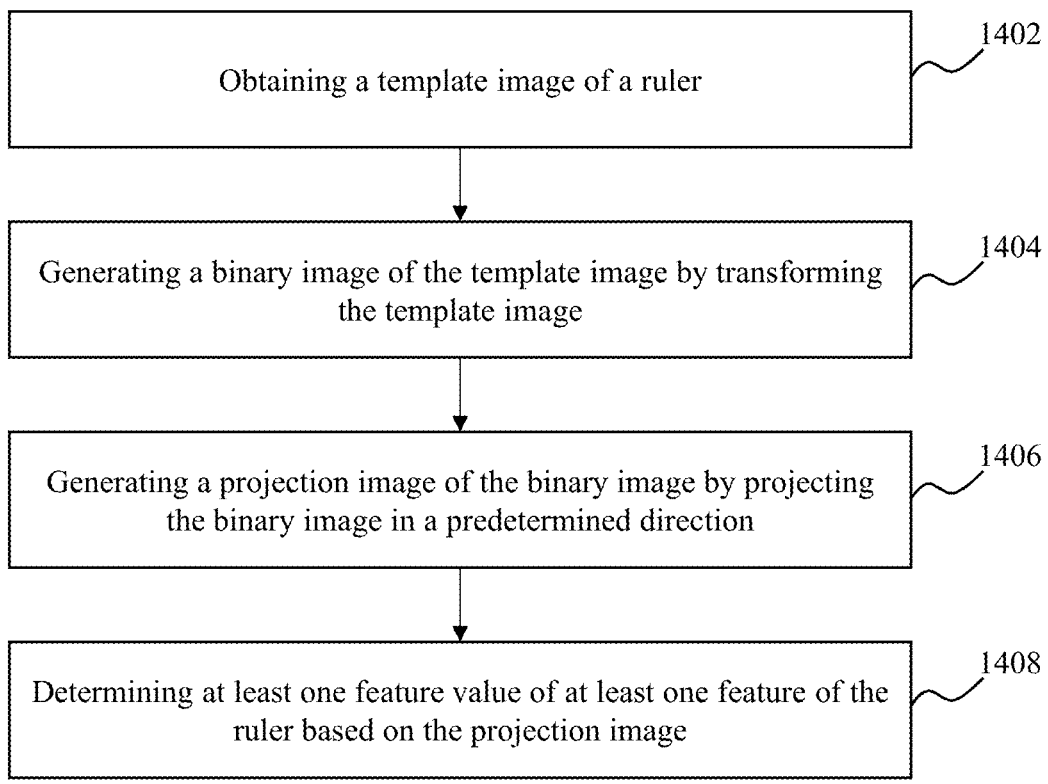
FIG. 14 is a flowchart illustrating an exemplary process for determining a plurality of feature values of a plurality of features of a ruler according to some embodiments of the present disclosure.

FIG. 14 is a flowchart illustrating an exemplary process for determining a plurality of feature values of a plurality of features of a ruler according to some embodiments of the present disclosure. In some embodiments, one or more operations of the process 1400 illustrated in FIG. 14 may be implemented in the imaging system 100 illustrated in FIG. 1. For example, the process 1400 illustrated in FIG. 14 may be stored in a storage device (e.g., the storage device 150, and/or the storage 220) of the imaging system 100 in the form of instructions, and invoked and/or executed by the processing device 140 (e.g., the processor 210 of the computing device 200 as illustrated in FIG. 2, the CPU 340 of the mobile device 300 as illustrated in FIG. 3, or one or more modules of the processing device 140 illustrated in FIG. 9).

In 1402, the processing device 140 (e.g., the determination module 904) may obtain a template image of the ruler.

Figures 22A, 22B:
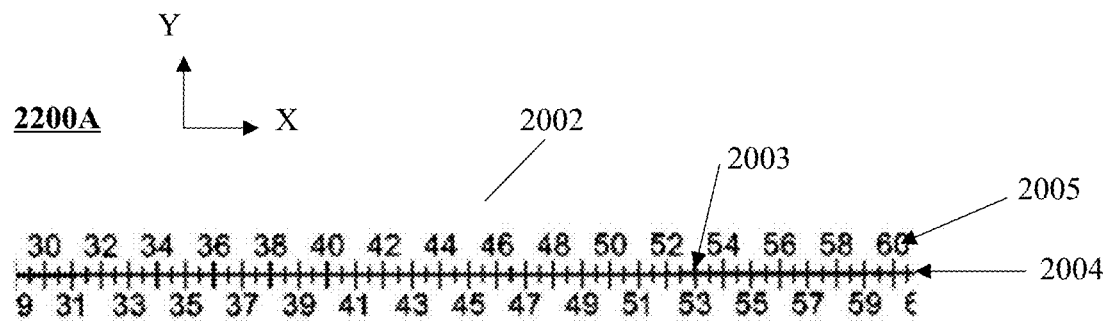
FIG. 22A illustrates an exemplary template image of a portion of the ruler in FIG. 20A according to some embodiments of the present disclosure.
FIG. 22B illustrates an exemplary binary template image of a portion of the ruler in FIG. 20A according to some embodiments of the present disclosure.

The template image of the ruler may refer to an image of the ruler that is used to determine feature values of the ruler. For illustration purposes, FIG. 22A illustrates an exemplary template image 2200A of a portion of the ruler 2002 in FIG. 20A according to some embodiments of the present disclosure. In some embodiments, the template image may be captured by an imaging device (e.g., the imaging device 110, a camera). Alternatively, the template image may be segmented from an image including the ruler and one or more other subjects. In some embodiments, template images of different rulers may be captured by an imaging device under a same condition or under different conditions (e.g., using different doses). In some embodiments, the template image may be obtained from, for example, a storage device (e.g., the storage device 150, the storage 220, or an external source), a terminal device (e.g., the terminal 130), or another source that stores the template image.

In 1404, the processing device 140 (e.g., the determination module 904) may generate a binary template image of the template image by transforming the template image.

In the binary template image, a pixel having a pixel value of 1 may be represented in white, and a pixel having a pixel value of 0 may be represented in black. In some embodiments, for each pixel in the template image, the processing device 140 may determine whether the pixel value of the pixel is greater than a threshold value. If the pixel value of the pixel is greater than the threshold value, the processing device 140150 may determine that the pixel value of the pixel in the binary template image is equal to 1. If the pixel value of the pixel is less than the threshold value, the processing device 140 may determine that the pixel value of the pixel in the binary template image is equal to 0. In some embodiments, the processing device 140 may generate the binary template image based on a local binarization algorithm. For illustration purposes, FIG. 22B illustrates an exemplary binary template image 2200B of a portion of the ruler 2002 in FIG. 20A according to some embodiments of the present disclosure.

In 1406, the processing device 140 (e.g., the determination module 904) may generate a projection image of the binary template image by projecting the binary template image in a predetermined direction.

In some embodiments, the projection image may be generated by summing pixel values of a set of pixels that are arranged side by side along the predetermined direction in the binary template image. For illustration purposes, an X-axis and a Y-axis are provided in FIG. 22A to present a horizontal direction and a vertical direction, respectively. In some embodiments, the binary template image may be placed horizontally or roughly horizontally as shown in FIG. 22B. The processing device 140 may generate a horizontal projection image by projecting the binary template image in the horizontal direction. The horizontal projection image may include a first axis representing coordinates along the vertical direction and a second axis representing a sum of pixel values of a set of pixels that have a certain coordinate on the first axis. As another example, the binary template image may be placed vertically or roughly vertically. The processing device 140 may generate a vertical projection image by projecting the binary template image in the vertical direction. The vertical projection image may include a first axis representing coordinates along the horizontal direction and a second axis representing a sum of pixel values of a set of pixels that have a certain coordinate on the first axis.

Figure 23A:
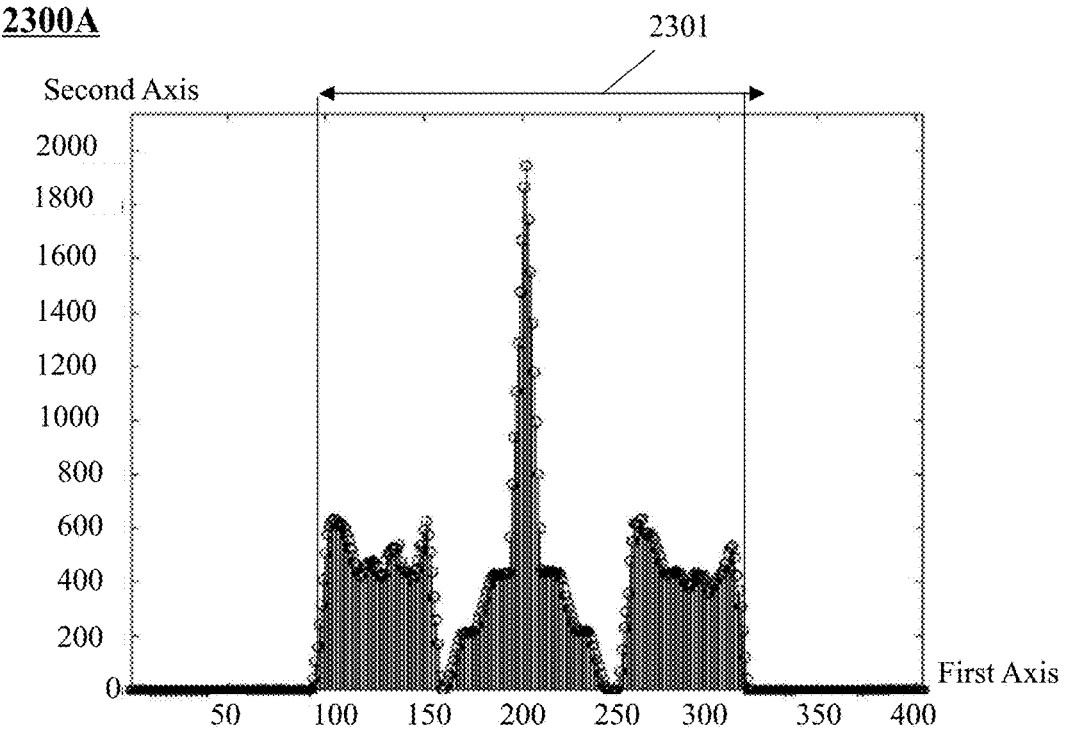
FIGS. 23A and 23B illustrate exemplary candidate horizontal projection images of the binary template image in FIG. 22B according to some embodiments of the present disclosure.
Figure 23B:
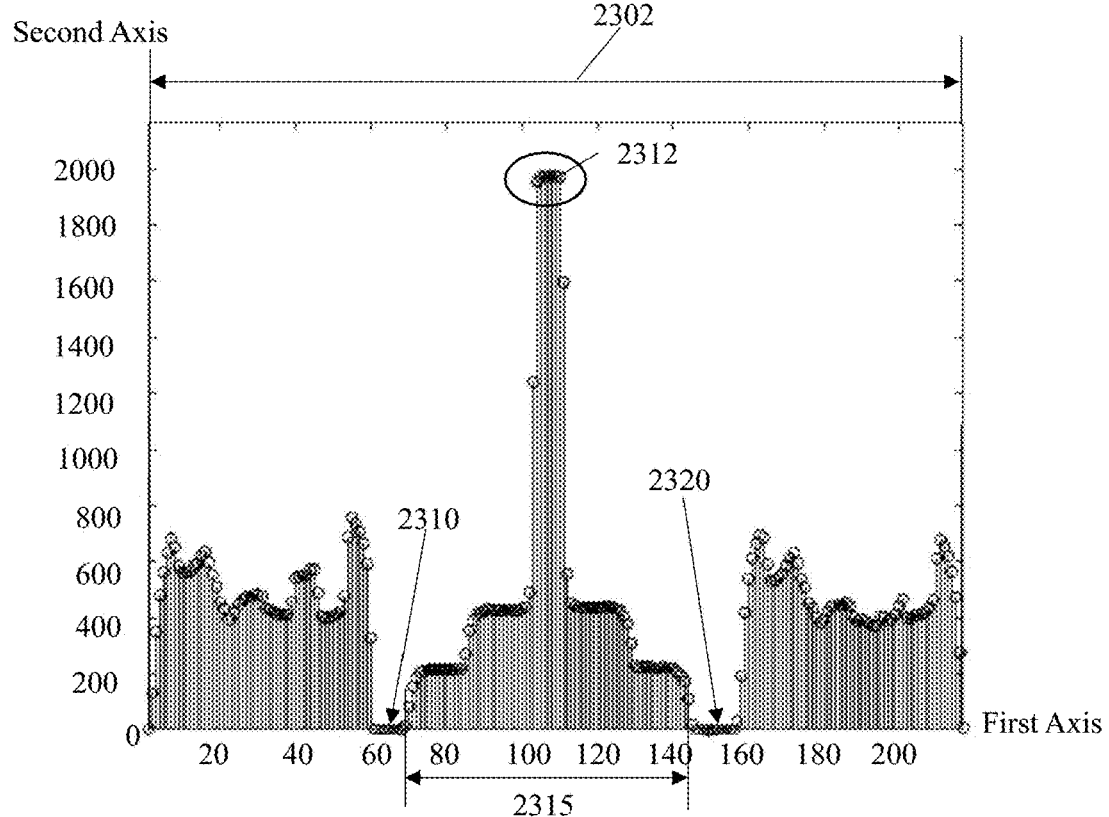

In some embodiments, the processing device 140 may generate a plurality of rotated binary template images. Each rotated binary template image may be generated by rotating the binary template image by a degree. For each of the rotated binary template images, the processing device 140 may determine a candidate projection image of the rotated binary template image by projecting the rotated binary template image in the predetermined direction. For example, for each rotated binary template image, the processing device 140 may generate a candidate horizontal projection image along the horizontal direction or a candidate vertical projection image along the vertical direction. Then, the processing device 140 may select the projection image from the candidate projection images. For illustration purposes, FIGS. 23A and 23B illustrate exemplary candidate horizontal projection images 2300A and 2300B of the binary template image 2200B, respectively, according to some embodiments of the present disclosure.

In some embodiments, the processing device 140 may determine a value range in each candidate projection image. A value range in a candidate projection image may refer to a coordinate difference between a first non-zero value and a last non-zero value in the first axis of the candidate projection image. For example, the candidate horizontal projection image 2300A has a value range 2301 as shown in FIG. 23A, and the candidate horizontal projection image 2300B has a value range 2302 as shown in FIG. 23B. The processing device 140 may further select a candidate projection image having the smallest value range as the projection image. For example, a candidate horizontal projection image having the smallest value range may be selected as the horizontal projection image. As another example, a candidate vertical projection image having the smallest value range may be selected as the vertical projection image.

In 1408, the processing device 140 (e.g., the determination module 904) may determine the feature values of the features of the ruler based on the projection image.

In some embodiments, the processing device 140 may determine a ruler width of the ruler according to the projection image. For example, the ruler width may be equal to the value range in the first axis of the projection image as described above.

In some embodiments, the processing device 140 may determine whether the ruler has a scale axis according to the projection image. For example, the processing device 140 may determine whether the projection image includes a sum of pixel values greater than a preset threshold (i.e., whether includes a point whose value in the second axis greater than the preset threshold). If the projection image includes a sum of pixel values greater than the preset threshold, it may be determined that the ruler has a scale axis. If the projection image does not include a sum of pixel values greater than the preset threshold, it may be determined that the ruler does not have the scale axis. Normally, the scale axis may have a length that is approximately the same as the ruler along the extension direction of the ruler. Thus, in some embodiments, the preset threshold may be equal to a product of a length of the ruler in the template image and a coefficient (e.g., 0.8, 0.9, or 0.95). Merely by way of example, the length the ruler in the template image may be equal to 2,000 pixels, and the preset threshold may be equal to 0.95*2,000.

Optionally, if the ruler includes a scale axis, the processing device 140 may further determine a width of the scale axis. For example, a plurality of points whose values in the second axis are greater than the preset threshold may be determined. The maximum difference between the coordinates of the points in the first axis may be determined as the width of the scale axis. Merely by way of example, it is assumed that the projection image is the candidate horizontal projection image 2300B as illustrated in FIG. 23B. A point set 2312 may include a plurality of points whose values in the second axis are greater than the preset threshold. The maximum difference between the coordinates of the points in the point set 2312 may be determined as the width of the scale axis.

In some embodiments, the ruler may include one or more scale lines and one or more numbers. The processing device 140 may determine a feature value relating to the scale line(s) and a feature value relating to the number(s). For example, the processing device 140 may segment the scale line(s) and number(s) from the binary template image according to the projection image. Normally, as shown in FIG. 22B, along the vertical direction, there may be a first gap between the number(s) and the scale line(s) in the upper portion of the ruler and a second gap between the number(s) and the scale line(s) in the lower portion of the ruler. In the projection image, the first and second gaps may be represented by points whose values in the second axis are equal to 0. For example, it is assumed that the candidate horizontal projection image is the projection image. As shown in FIG. 23B, an interval 2310 and an interval 2320 may represent the first gap and the second gap, respectively. A region in the projection image between the interval 2310 and the interval 2320 may represent the scale line(s). The processing device 140 may further determine the position and/or the width of the scale line(s) based on the region representing the scale line(s). Optionally, the processing device 140 may further segment the scale line(s) from the binary template image (or the template image), wherein the segmented region including the scale line(s) may be referred to as a scale line template and the remaining part including the number(s) be referred to as a number template.

Figure 24A:
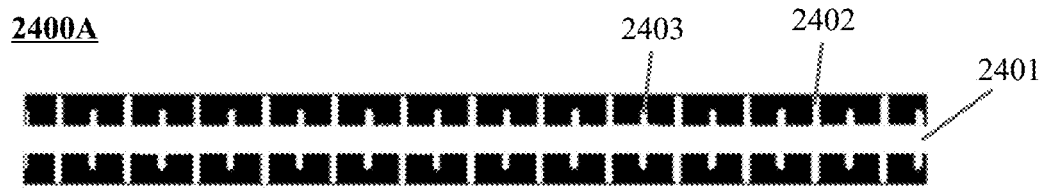
FIG. 24A illustrates an exemplary scale line template according to some embodiments of the present disclosure.
Figure 24B:
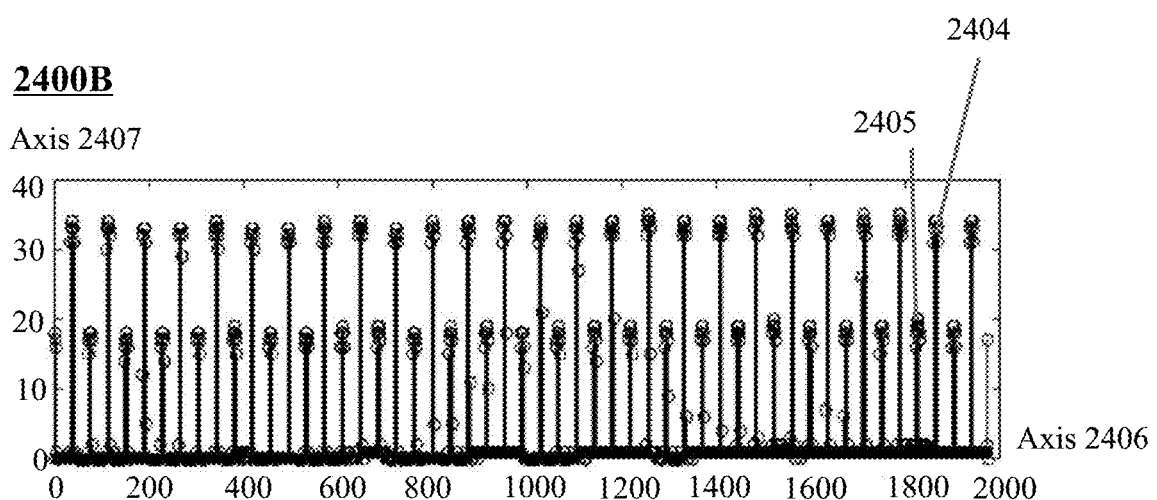
FIG. 24B illustrates a projection image of an upper portion of the scale line template in FIG. 24A according to some embodiments of the present disclosure.
Figure 24C:
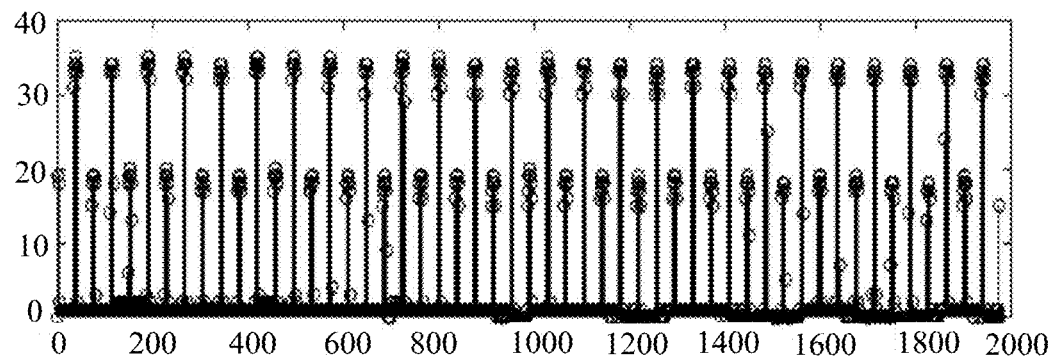
FIG. 24C illustrates a projection image of a lower portion of the scale line template in FIG. 24A according to some embodiments of the present disclosure.

In some embodiments, the processing device 140 may further project the scale line template to obtain a projection image of the scale line template. The processing device 140 may determine one or more feature values relating to the scale line(s) according to the projection image of the scale line template. For illustration purposes, FIG. 24A illustrates an exemplary scale line template 2400A according to some embodiments of the present disclosure. The scale line template 2400A may include a scale axis 2401, and a plurality of scale lines (e.g., a plurality of long scale lines 2402 and a plurality of short scale lines 2403). FIG. 24B illustrates a projection image 2400B of an upper portion of the scale line template 2400A according to some embodiments of the present disclosure. The projection image 2400B was generated by projecting the upper portion of the scale line template 2400A (which is arranged horizontally as shown in FIG. 24A) in the vertical direction. The projection image 2400B has an axis 2406 representing coordinates along the horizontal direction and an axis 2407 representing a sum of pixel values of pixels that have a same coordinate on the axis 2406. As shown in FIG. 24B, the projection image 2400B has a plurality of long columns 2404 and a plurality of short columns 2405. In some embodiments, the count of types of the scale lines in the upper portion of scale line template 2400A may be equal to the count of types of the columns in the projection image 2400B. For example, a long column 2404 may represent a long scale line 2402, and a short column 2405 may represent a short scale line 2403, indicating that the upper portion of the scale line template 2400A has two types of scale lines. A length of a scale line in the upper portion of the scale line template 2400A along the vertical direction may be equal to a value of a corresponding column along the axis 2407 in the projection image 2400B. A distance between two adjacent scale lines in the upper portion of scale line template 2400A may be equal to a coordinate difference between two adjacent columns along the axis 2406 in the projection image 2400B. A unit length of the scale lines in the upper portion of scale line template 2400A may be equal to a coordinate difference between two adjacent columns of the same type along the axis 2406 in the projection image 2400B. FIG. 24C illustrates a projection image 2400C of a lower portion of the scale line template 2400A according to some embodiments of the present disclosure. The feature values of the scale lines in the lower portion of the scale line template 2400A may be determined based on the projection image 2400C in a similar manner as those of the scale lines in the upper portion of the scale line template 2400A.

Figures 25A, 25B:
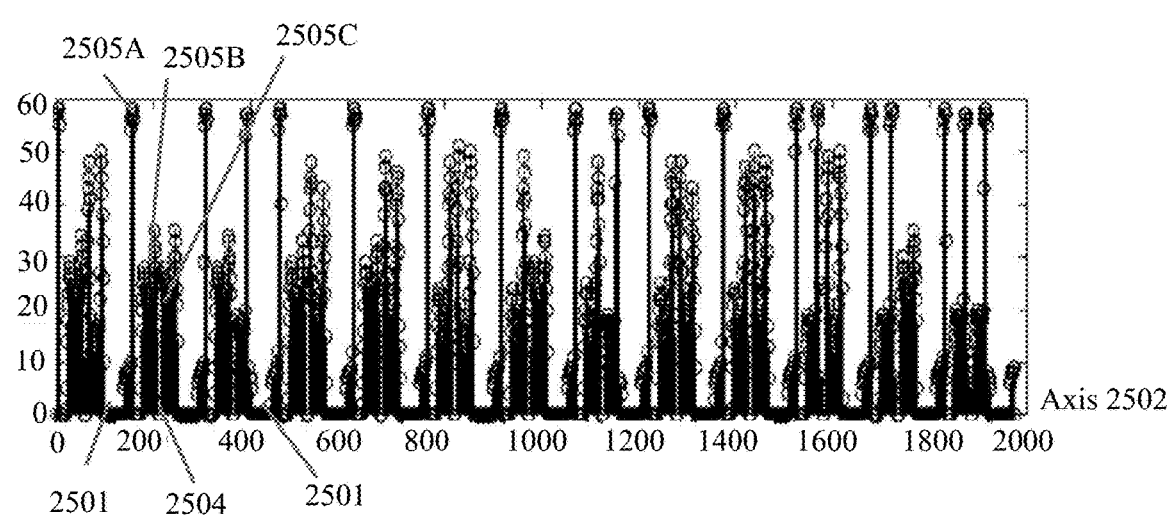
FIG. 25A illustrates a portion of an exemplary number template according to some embodiments of the present disclosure.
FIG. 25B illustrates a projection image of an upper portion of the number template in FIG. 25A according to some embodiments of the present disclosure.
Figure 25C:
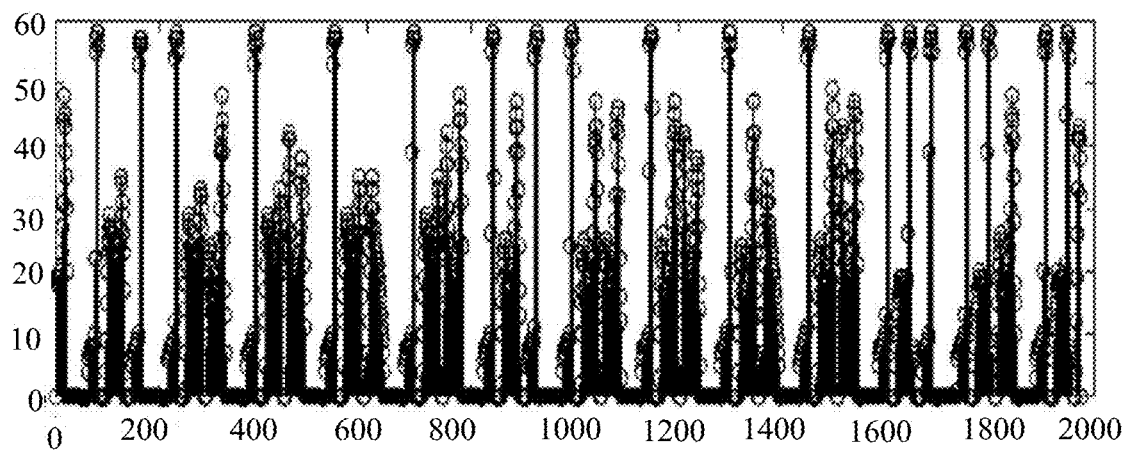
FIG. 25C illustrates a projection image 2500C of a lower portion of the number template in FIG. 25A according to some embodiments of the present disclosure.
Figure 25D:
FIG. 25D illustrates a plurality of numbers segmented from the number template in FIG. 25A according to some embodiments of the present disclosure.

Additionally or alternatively, the processing device 140 may further project the number template to obtain a projection image of the number template. The processing device 140 may determine one or more feature values relating to the number(s) according to the projection image of the number template. For illustration purposes, FIG. 25A illustrates a portion of an exemplary number template 2500A according to some embodiments of the present disclosure. FIG. 25B illustrates a projection image 2500B of an upper portion of the number template 2500A according to some embodiments of the present disclosure. The upper portion of the number template 2500A includes numbers "122," "123," . . . , and "144," wherein "122" to a portion of "133" are illustrated in FIG. 25A. The projection image 2500B was generated by projecting the upper portion of the number template 2500A (which is arranged horizontally as shown in FIG. 25A) in the vertical direction. The projection image 2500B has an axis 2502 representing coordinates along the horizontal direction and an axis 2503 representing a sum of pixel values of pixels that have a same coordinate on the axis 2502. As illustrated in FIG. 25B, the projection image 2500B includes a plurality of column groups separated by a plurality of large intervals 2501. Each column group includes three columns separated by a plurality of small intervals 2504. Each interval (2501 or 2504) includes points whose values on the axis 2503 are equal to 0. In some embodiments, the position of the numbers in the upper portion of the number template 2500A may be determined based on the intervals 2501 and 2504. For example, a column group between two adjacent large intervals 2501 in the projection image 2500B may represent a group of numbers in the upper portion of the number template 2500A. A column between two adjacent small intervals 2504 in the projection image 2500B may represent a single number in the upper portion of the number template 2500A. Merely by way of example, as shown in FIG. 25B, a column group representing a group of numbers "122" includes three columns 2505A, 2505B, and 2505C. The columns 2505A, 2505B, and 2505C represents number "1," "2," and "2," respectively. FIG. 25C illustrates a projection image 2500C of a lower portion of the number template 2500A according to some embodiments of the present disclosure. The feature values of the numbers in the lower portion of the number template 2500A may be determined based on the projection image 2500C in a similar manner as those of the upper portion of the number template 2500A. Optionally, the numbers in the number template image 2500A may be segmented based on the positions of the numbers. For example, FIG. 25D illustrates a plurality of numbers segmented from the number template 2500A according to some embodiments of the present disclosure.

Figure 15:
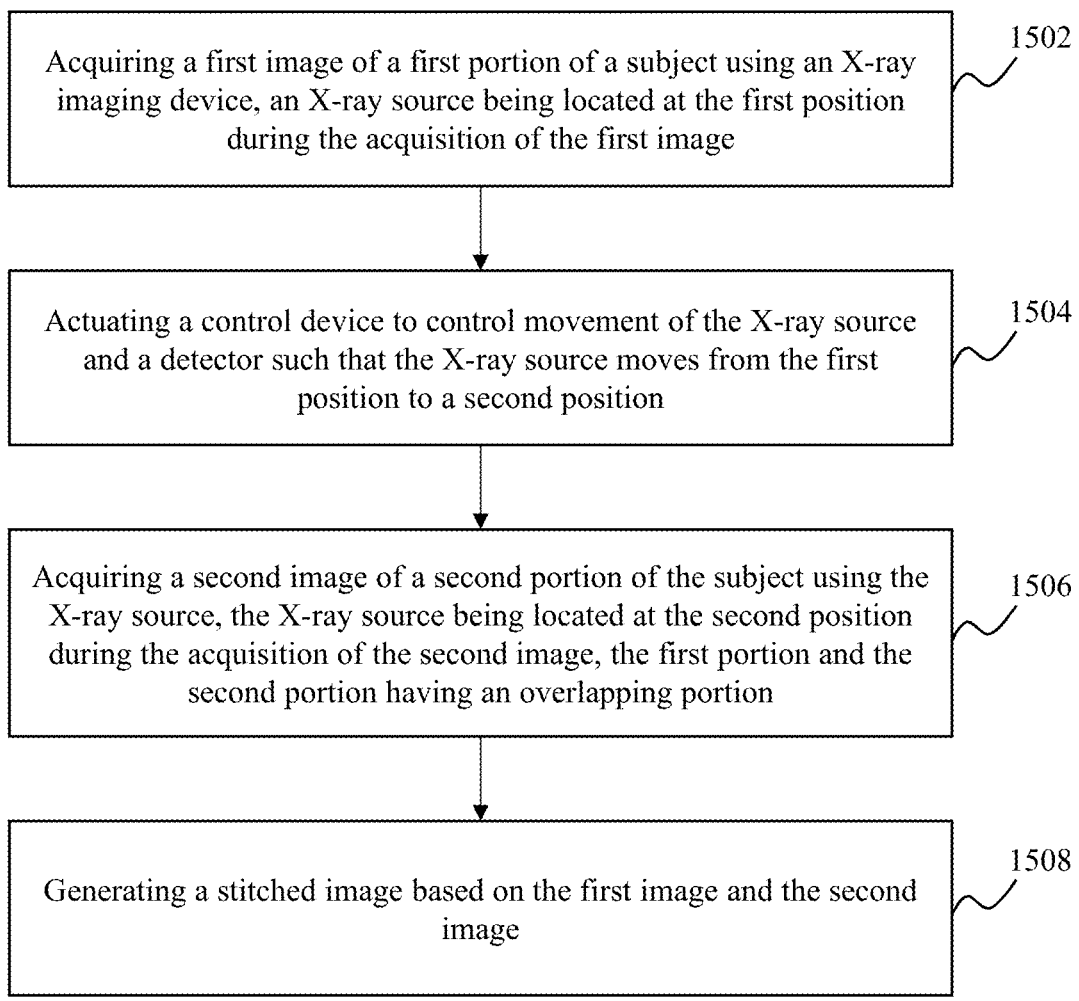
FIG. 15 is a flowchart illustrating an exemplary process for generating a stitched image according to some embodiments of the present disclosure.

FIG. 15 is a flowchart illustrating an exemplary process for generating a stitched image according to some embodiments of the present disclosure. In some embodiments, one or more operations of process 1500 illustrated in FIG. 15 may be implemented in the imaging system 100 illustrated in FIG. 1. For example, the process 1500 illustrated in FIG. 15 may be stored in a storage device (e.g., the storage device 150, and/or the storage 220) of the imaging system 100 in the form of instructions, and invoked and/or executed by the processing device 140 (e.g., the processor 210 of the computing device 200 as illustrated in FIG. 2, the CPU 340 of the mobile device 300 as illustrated in FIG. 3, or one or more modules of the processing device 140 illustrated in FIG. 9).

In some embodiments, the process 1500 may be implemented based on an X-ray imaging device. The X-ray imaging device may be a same or similar imaging device as any one of the X-ray imaging devices 400, 500, 600, 700, and 800 as described elsewhere in this disclosure (e.g., FIGS. 4 to 8D and the relevant descriptions). For illustration purposes, an X-ray imaging device 1600 is provided in FIGS. 16A and 16B as an example of the X-ray imaging device. The X-ray imaging device 1600 may include an X-ray source 113, a detector 112, and a control device (not shown in FIGS. 16A and 16B) configured to control the movement of the X-ray source 113 and the detector 112.

In 1502, the processing device 140 (e.g., the obtaining module 902) may obtain a first image of a first portion of a subject using the X-ray imaging device 1600.

Figure 16A:
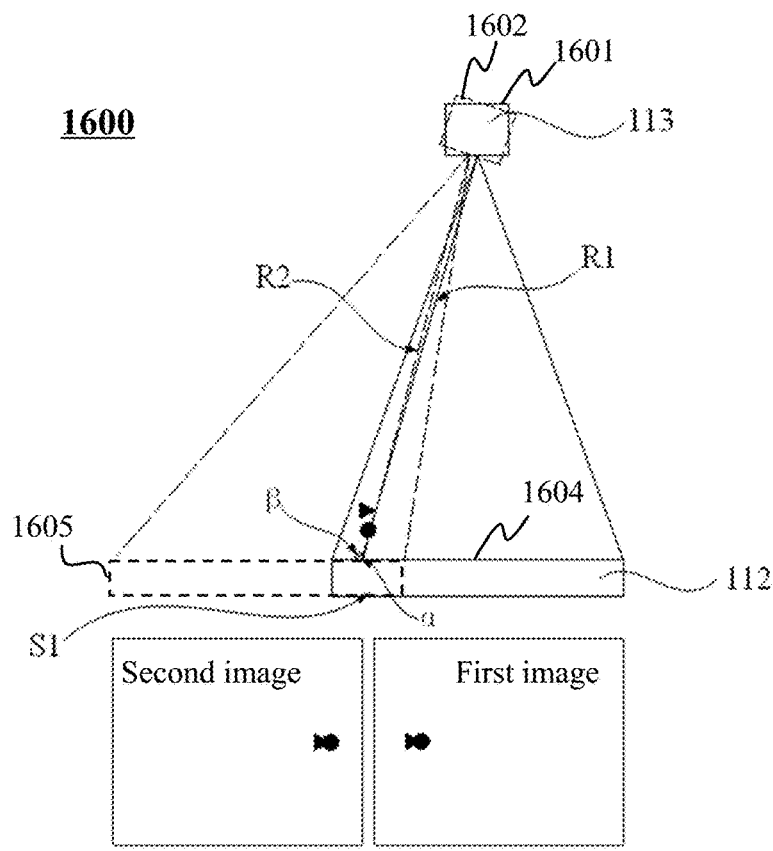
FIGS. 16A and 16B are schematic diagrams illustrating an exemplary imaging device according to some embodiments of the present disclosure.
Figure 16B:
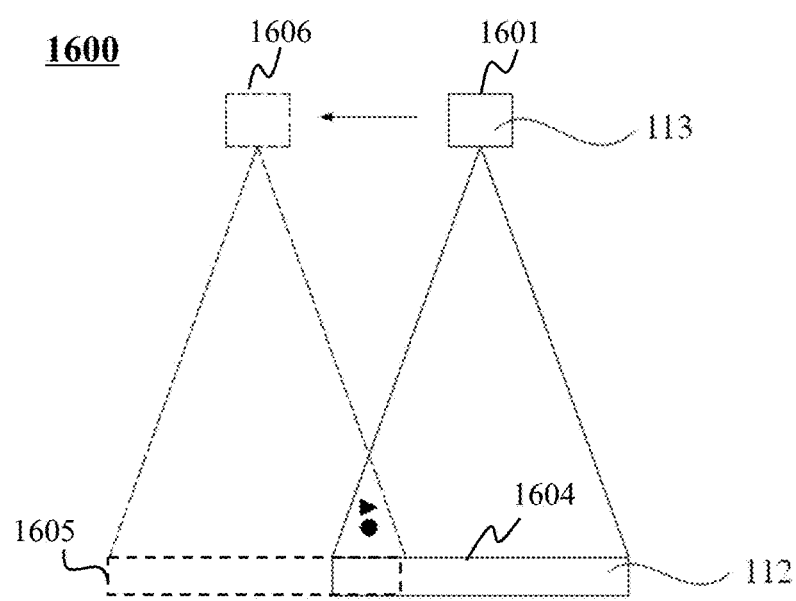

In some embodiments, the X-ray imaging device 1600 may be configured to perform a first scan on the first portion of the subject. During the first scan, the X-ray source 113 and the detector 112 may be located at a first position and a second position, respectively. For example, as shown in FIGS. 16A and 16B, the X-ray source 113 is located at a first position indicated by a solid box 1601, and the detector 112 may be located at a second position indicated by a solid box 1604. The X-ray source 113 may emit radiation rays (as indicated by solid lines emitted from the X-ray source 113 in FIGS. 16A and 116B) toward the first portion of the subject. The detector 112 may receive radiation rays that pass through the first portion of the subject. The first image may be generated by the X-ray imaging device 1600 or a computing device (e.g., the processing device 140) based on the radiation rays received by the detector 112 in the first scan.

In 1504, the processing device 140 (e.g., the actuation module 910) may direct the control device to control movement of the X-ray source 113 and the detector 112. Under the control of the control device, the X-ray source 113 may move from the first position to a third position and the detector 112 may move from the second position to a fourth position.

In some embodiments, the movements of the detector 112 may include a translation movement. For example, as shown in FIGS. 16A and 16B, the detector 112 may translate from the second position indicated by the solid box 1604 to a fourth position indicated a dotted box 1605. In some embodiments, the subject may lie on a table during the acquisition of the first image. The detector 112 may translate on a plane that is parallel with the table to move from the second position to the fourth position. In some embodiments, the translation direction may be associated with a region of interest to be imaged. For example, if the region of interest is the spine of the subject, the detector 112 may translate along a direction that is parallel with the extension direction of the spine (i.e., a direction from the head to the feet of the subject).

In some embodiments, the movement of the X-ray source 113 may include a rotation movement and/or a translation movement. For example, as shown in FIG. 16A, the X-ray source 113 may rotate from the first position indicated by the solid box 1601 to a third position indicated by a dotted box 1602. As another example, as shown in FIG. 16B, the X-ray source 113 may translate from the first position indicated by the solid box 1601 to a third position indicated by a dotted box 1606. In some embodiments, the subject may lie on the table during the acquisition of the first image. The X-ray source 113 may rotate around an axis parallel with the table and/or translate along the same translation direction as the detector 112 to move from the first position to the third position. In some embodiments, the X-ray imaging device 1600 may be regarded as operating in a tilting mode if during the image acquisition, the detector 112 has a translation movement and the X-ray source 113 has a rotation movement as shown in FIG. 16A. The X-ray imaging device 1600 may be regarded as operating in a stepping mode if during the image acquisition, the detector 112 and the X-ray source 113 both have a translation movement as shown in FIG. 16A. The X-ray imaging device 1600 may be regarded as operating in a combined mode of the tilting mode and the stepping mode if during the image acquisition, the detector 112 has a translation movement and the X-ray source 113 has a translation movement and also a rotation movement. Exemplary X-ray imaging device having a tilting mode may be found in U.S. patent application Ser. No. 6,898,269, titled "Methods and Apparatus for X-ray images" filed on Feb. 10, 2003. The entire contents of the above-referenced application are hereby incorporated by reference.

In some embodiments, the X-ray imaging device 1600 may further include a gantry (e.g., the gantry 111), a first arm (e.g., the first arm 430), and a second arm (e.g., the second arm 440). The first arm may have a first end mechanically connected to the gantry and a second end mechanically connected to the detector 112. The second arm may have a third end mechanically connected to the gantry and a fourth end mechanically connected to the X-ray source 113. The control device may control the movement of the detector 112 via the first arm. For example, the control device may drive the first arm to rotate and/or translate, and the rotation and/or the translation of the first arm may drive the translation of the detector 112. Additionally or alternatively, the control device may control the movement of the X-ray source 113 via the second arm. For example, the control device may drive the second arm to rotate and/or translate, and the rotation and/or the translation of the second arm may drive the movement of the X-ray source 113. In some embodiments, the X-ray imaging device 1600 may include one or more motion control devices, such as the first, second, third, fourth, and fifth motion control devices as described elsewhere in this disclosure (e.g., FIGS. 4 to 8D and the relevant descriptions). The control device may control the movement the detector 112 and/or the movement of the X-ray source 113 via the motion control device(s). More detailed description regarding the motion control device(s) may be found elsewhere. See, e.g., FIGS. 4 to 8D, and the description thereof.

In 1506, the processing device (e.g., the obtaining module 902) may acquire a second image of a second portion of the subject using the X-ray imaging device 1600.

In some embodiments, the X-ray imaging device 1600 may be configured to perform a second scan on the second portion of the subject. During the second scan, the X-ray source 113 and the detector 112 may be located at the third position and the fourth position, respectively. The X-ray source 113 may emit radiation rays (as indicated by dotted lines emitted from the X-ray source 113 in FIGS. 16A and 116B) toward the second portion of the subject. The detector 112 may receive radiation rays that pass through the second portion of the subject. The second image may be generated by the X-ray imaging device 1600 or a computing device (e.g., the processing device 140) based on the radiation rays received by the detector 112 in the second scan.

In some embodiments, the second portion and the first portion may have an overlapping portion. Accordingly, each of the first image and the second image may have an overlapping region representing the overlapping portion of the subject. For example, as illustrated in FIG. 16A, a portion S1 of the detector 112 may receive radiation rays from the overlapping portion of the subject in both the first scan and the second scan. The first image and the second image may both have an overlapping region that corresponds to the overlapping portion of the subject and the portion S1 of the detector 112.

In some embodiments, during the acquisition of the first image, a first set of radiation rays emitted by the X-ray source 113 may pass through the overlapping portion of the subject and received by the portion S1 of the detector 112. The radiation rays in the first set may have a first range of incidence angles with respect to the detector 112. An incidence angle of a radiation ray may refer to an angle formed by the radiation ray and a plane defined by the detector 112, such as an incidence angle $\alpha$ formed by a radiation ray R1 and the plane and an incidence angle $\beta$ formed by a radiation ray R2 and the plane as shown in FIG. 16A. During the acquisition of the second image, a second set of radiation rays emitted by the X-ray source 113 may pass through the overlapping portion of the subject and received by the portion S1 of the detector 112. The radiation rays in the second set may have a second range of incidence angles with respect to the detector 112. The first range and the second range may at least partially overlap with each other. In some embodiments, the first range and the second range may be the same or substantially the same with each other. For example, the first range and the second range may be denoted as [A, B] and [C, D], respectively. A and C may be equal to each other or a difference between A and C may the smaller than a threshold degree (e.g., 1 degree, 3 degrees, 5 degrees, etc.). B and D may be equal to each other or a difference between B and D may the smaller than the threshold degree. This may improve the similarity between the overlapping regions in the first and second images, thus improving the precision and quality of image stitching performed based on the first and second images.

In 1508, the processing device 140 (e.g., the generation module 906) may generate a stitched image based on the first image and the second image.

In some embodiments, the processing device 140 may generate the stitched image by fusing the first image and the second image according to an image fusion algorithm. In some embodiments, the processing device 140 may perform a method for image stitching disclosed in the present disclosure to generate the stitched image. For example, the first image may be designated as a reference image and the second image may be designated as a target image. The processing device 140 may perform the process 1000 as described in connection with FIG. 10 to stitch the reference image and the target image. As another example, each of the first and second images may include at least a portion of a ruler. For each of the first and second images, the processing device 140 may process the image by removing the ruler in the image, for example, by performing the process 1200 on the image. The processed first image and the processed second image may be designated as the reference image and the target image, respectively. The processing device 140 may further stitch the reference image and the target image, for example, by performing the process 1000.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A non-transitory computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system for image stitching, comprising:
   at least one storage device including a set of instructions; and
   at least one processor configured to communicate with the at least one storage device, wherein when executing the set of instructions, the at least one processor is configured to direct the system to perform operations including:
   obtaining a reference image of a first portion of a subject and a target image of a second portion of the subject, the first portion and the second portion at least partially overlapping with each other;
   determining, based on a preliminary registration accuracy, at least one pair of feature points, each pair including a reference feature point in the reference image and a target feature point in the target image that matches the reference feature point;
   for each of the at least one pair, determining, based on a superior registration accuracy and a neighboring region of the target feature point of the pair, an updated pair of feature points, the updated pair including the reference feature point of the pair and an updated target feature point in the target image, the superior registration accuracy being higher than the preliminary registration accuracy; and
   generating, based on the at least one updated pair, a stitched image of the reference image and the target image.

2. The system of claim 1, wherein the preliminary registration accuracy is a pixel-level accuracy, and the superior registration accuracy is a subpixel-level accuracy.

3. The system of claim 1, wherein to determine an updated pair of feature points for a pair of feature points, the at least one processor is further configured to direct the system to perform additional operations including:
   performing one or more iterations, each current iteration of the one or more iteration comprising:
      determining a plurality of interpolation points in a neighboring region of the target feature point in the current iteration;
      for each of the plurality of interpolation points, determining a similarity degree between the interpolation point and the reference feature point of the pair;
      selecting, among the plurality of interpolation points, an interpolation point that has the highest similarity degree with the reference feature point;
      determining whether the selected interpolation point satisfies a termination condition corresponding to the current iteration, the termination condition including that the selected interpolation point achieves the superior registration accuracy corresponding to the current iteration; and
      in response to a determination that the selected interpolation point satisfies the termination condition in the current iteration, designating the selected interpolation point as the updated target feature point.

4. The system of claim 3, wherein the termination condition in the current iteration further includes that a similarity degree between the selected interpolation point and the reference feature point is within a similarity range corresponding to the current iteration.

5. The system of claim 3, wherein in response to a determination that the selected interpolation point does not satisfy the termination condition corresponding to the current iteration, the at least one processor is further configured to direct the system to perform additional operations including:
   designating the selected interpolation point as a target feature point in a next iteration.

6. The system of claim 5, wherein in response to a determination that the selected interpolation point does not satisfy the termination condition corresponding to the current iteration, the at least one processor is further configured to direct the system to perform additional operations including:
   updating the termination condition, the updated termination condition including an updated superior registration accuracy higher than the superior registration accuracy corresponding to the current iteration; and
   designating the updated termination condition as a termination condition corresponding to the next iteration.

7. The system of claim 3, wherein each current iteration further comprises:
   determining, based on the superior registration accuracy corresponding to the current iteration, the neighboring region of the target feature point in the current iteration.

8. The system of claim 1, wherein to generate a stitched image of the reference image and target image, the at least one processor is further configured to direct the system to perform additional operations including:
   generating a preliminary stitched image by combining the target image and the reference image based on the at least one updated pair, the preliminary stitched image including a seam; and
   generating the stitched image by removing the seam from the preliminary stitched image.

9. The system of claim 1, wherein the at least one processor is further configured to direct the system to perform additional operations including:
   obtaining a preliminary reference image of the first portion of the subject and a preliminary target image of the second portion of the subject, each of the preliminary reference image and the preliminary target image including at least a portion of a ruler;
   for each image of the preliminary reference image and the preliminary target image, processing the image by removing the ruler from the image;
   designating the processed preliminary reference image as the reference image; and
   designating the processed preliminary target image as the target image.

10. The system of claim 9, wherein for each image of the preliminary reference image and the preliminary target image, to process the image by removing the ruler from the image, the at least one processor is further configured to direct the system to perform additional operations including:
    obtaining at least one feature value of at least one feature of the ruler, the at least one feature including at least an identification feature;
    identifying, based on the feature value of the identification feature, the ruler in the image; and
    processing the image by removing the identified ruler from the image.

11. The system of claim 10, wherein the identification feature includes a positioning feature and a matching feature, and
    to identify the ruler in the image, the at least one processor is further configured to direct the system to perform additional operations including:

determining, based on the feature value of the positioning feature, a preliminary region representing the ruler in the image; and identifying, based on the preliminary region and the feature value of the matching feature, the ruler in the image.

12. The system of claim 11, wherein the ruler has a scale axis, the positioning feature includes a ruler width of the ruler and a feature relating to the scale axis, and to determine a preliminary region representing the ruler in the image, the at least one processor is further configured to direct the system to perform additional operations including:

determining, based on the feature value of the feature relating to the scale axis, a position of the scale axis in the image; and determining, based on the position of the scale axis and the feature value of the ruler width, the preliminary region representing the ruler in the image.

13. The system of claim 12, wherein to determine a position of the scale axis in the image, the at least one processor is further configured to direct the system to perform additional operations including:

transforming the image into a binary image;

identifying one or more straight lines in the binary image; and determining, based on the one or more straight lines and the feature value of the feature relating to the scale axis, the position of the scale axis in the image.

14. The system of claim 11, wherein the ruler includes one or more numbers, the matching feature includes a feature relating to the one or more numbers, and to identify, based on the preliminary region and the feature value of the matching feature, the ruler in the image, the at least one processor is further configured to direct the system to perform additional operations including:

identifying at least one number of the one or more numbers in the preliminary region; and identifying, based on the at least one number and the feature value of the feature relating to the one or more numbers, the ruler in the image.

15. The system of claim 10, wherein the at least one feature further includes a validation feature different from the identification feature, and to process the image by removing the identified ruler from the image, the at least one processor is further configured to direct the system to perform additional operations including:

determining, based on the identified ruler and the feature value of the validation feature, whether the identification of the ruler is valid; and in response to a determination that the identification of the ruler is valid, removing the identified ruler.

16. The system of claim 15, wherein the ruler includes one or more scale lines, the validation feature includes a feature relating to the one or more scale lines, and to determine whether the identification of the ruler is valid, the at least one processor is further configured to direct the system to perform additional operations including:

identifying, from the image, at least one scale line; and determining, based on the identified at least one scale line and the feature value of the feature relating to the one or more scale lines, whether the identification of the ruler is valid.

17. The system of claim 10, wherein to obtain at least one feature value of at least one feature of the ruler, the at least one processor is further configured to direct the system to perform additional operations including:

obtaining a template image of the ruler;

generating a binary template image of the template image by transforming the template image;

generating a projection image of the binary template image by projecting the binary template image in a predetermined direction; and determining, based on the projection image, the at least one feature value of the at least one feature of the ruler.

18. The system of claim 17, wherein to generate a projection image of the binary template image in a predetermined direction, the at least one processor is further configured to direct the system to perform additional operations including:

generating a plurality of rotated binary template images, each rotated binary template image being generated by rotating the binary template image by a degree;

for each of the plurality of rotated binary template images, generating a candidate projection image of the rotated binary template image by projecting the rotated binary template image in the predetermined direction; and selecting, from the candidate projection images, the projection image.

19. A method implemented on a computing device having at least one processor and at least one storage device for image stitching, the method comprising:

obtaining a reference image of a first portion of a subject and a target image of a second portion of the subject, the first portion and the second portion at least partially overlapping with each other;

determining, based on a preliminary registration accuracy, at least one pair of feature points, each pair including a reference feature point in the reference image and a target feature point in the target image that matches the reference feature point;

for each of the at least one pair, determining, based on a superior registration accuracy and a neighboring region of the target feature point of the pair, an updated pair of feature points, the updated pair including the reference feature point of the pair and an updated target feature point in the target image, the superior registration accuracy being higher than the preliminary registration accuracy; and generating, based on the at least one updated pair, a stitched image of the reference image and the target image.

* * * * *